United States Patent
Gregory et al.

(10) Patent No.: US 9,505,773 B2
(45) Date of Patent: Nov. 29, 2016

(54) RAPAMYCIN ANALOGUES AND THEIR PHARMACEUTICAL USE

(71) Applicant: Isomerase Therapeutics Limited, Cambridge (GB)

(72) Inventors: Matthew Alan Gregory, Cambridge (GB); Steven Gary Kendrew, Cambridge (GB); Steven James Moss, Cambridge (GB); Barrie Wilkinson, Cambridge (GB)

(73) Assignee: Isomerase Therapeutics Ltd., Cambridge (GB)

( * ) Notice: Subject to any disclaimer, the term of this patent is extended or adjusted under 35 U.S.C. 154(b) by 0 days.

(21) Appl. No.: 14/902,998

(22) PCT Filed: Jul. 9, 2014

(86) PCT No.: PCT/GB2014/052091
§ 371 (c)(1),
(2) Date: Jan. 5, 2016

(87) PCT Pub. No.: WO2015/004455
PCT Pub. Date: Jan. 15, 2015

(65) Prior Publication Data
US 2016/0176893 A1 Jun. 23, 2016

(30) Foreign Application Priority Data
Jul. 9, 2013 (GB) ................... 1312318.7

(51) Int. Cl.
| | | |
|---|---|---|
| A61K 31/453 | (2006.01) | |
| C07D 491/052 | (2006.01) | |
| C07D 498/18 | (2006.01) | |
| C12P 17/18 | (2006.01) | |
| A01N 43/90 | (2006.01) | |
| A01N 43/40 | (2006.01) | |
| C12P 17/16 | (2006.01) | |
| A61K 31/436 | (2006.01) | |
| A61K 45/06 | (2006.01) | |
| C07D 405/06 | (2006.01) | |

(52) U.S. Cl.
CPC ........... *C07D 491/052* (2013.01); *A01N 43/40* (2013.01); *A01N 43/90* (2013.01); *A61K 31/436* (2013.01); *A61K 31/453* (2013.01); *A61K 45/06* (2013.01); *C07D 405/06* (2013.01); *C07D 498/18* (2013.01); *C12P 17/16* (2013.01); *C12P 17/188* (2013.01)

(58) Field of Classification Search
USPC ...................... 514/291, 300, 321
See application file for complete search history.

(56) References Cited

FOREIGN PATENT DOCUMENTS

| | | | |
|---|---|---|---|
| WO | 98/27203 | 6/1998 | |
| WO | 98/49315 | 11/1998 | |
| WO | 00/09109 | 2/2000 | |
| WO | WO00/09109 | * 2/2000 | ............ A61K 31/00 |
| WO | 01/34816 | 5/2001 | |
| WO | 2004/007709 | 1/2004 | |
| WO | 2006/016167 | 2/2006 | |
| WO | 2015/004458 | 1/2015 | |

OTHER PUBLICATIONS

Nelson (Manipulation of the C(22)-C(27) region of rapamycin: stability issues and biological implications), Bioorganic and Medicinal Chemistry Letters, 1999, 18;9(2):295-300.*
Chemieret al., Evolution of Efficient Modular Polyketide Synthases by Homologous Recombination, J Am Chem Soc. 2015, 137(33):10603-9.
Chung et al., Deletion of rapQONML from the rapamycin gene cluster of Streptomyces hygroscopicus gives production of the 16-O-desmethyl-27-desmethoxy analog, J Antibiot (Tokyo), 2001, 54(3):250-6.
Jenke-Kodama et al., Natural biocombinatorics in the polyketide synthase genes of the actinobacterium Streptomyces avermitilis, PLoS Comput Biol, 2006, 2(10):e132.
Menzella et al., Combinatorial polyketide biosynthesis by de novo design and rearrangement of modular polyketide synthase genes, Nat Biotechnol, 2005, 23(9):1171-6.
Reeves et al., Genetic engineering to produce polyketide analogues, Methods Enzymol., 2009, 459:295-318.
Staunton et al., Polyketide biosynthesis: a millennium review., Nat Prod Rep. 2001, 18(4):380-416.
Staunton et al., Combinatorial biosynthesis of polyketides and nonribosomal peptides, Curr Opin Chem Biol. 2001, 5(2):159-64.
Nelson et al., Manipulation of the C(22)-C(27) region of rapamycin: stability issues and biological implications, Bioorg Med Chem Lett., 1999, 18;9(2):295-300.
Nelson et al., A novel ring contraction of rapamycin, Tetrahedron Letters, 1994, 34(41): 7557-7560.
Holt et al., Structure-activity studies of nonmacrocyclic rapamacin derivatives, Bioorganic & Medicinal Chemistry Letters, 1993, 3(10):1977-1980.
Skotnicki et al., Ring expanded rapamycin derivatives, Tetrahedron Letters, 1994, 35(2):201-202.
Xue et al., A multiplasmid approach to preparing large libraries of polyketides, Proc Natl Acad Sci U S A., 1999, 96 (21): 11740-11745.
Kittendorf et al., Developing tools for engineering hybrid polyketide synthetic pathways, Curr Opin Biotechnol., 2006, (6):597-605.
Kim et al., An efficient method for creation and functional analysis of libraries of hybrid type I polyketide synthases, Protein Eng Des Sel., 2004, 17(3):277-84.

(Continued)

Primary Examiner — Pancham Bakshi
(74) Attorney, Agent, or Firm — Robert C. Netter, Jr.; Dann, Dorfman, Herrell & Skillman

(57) ABSTRACT

Novel rapamycin analogues and methods for their production with FKBP and/or MIP inhibitory activity with reduced mTOR inhibitory activity with therapeutic potential e.g. as bacterial virulence inhibitors.

19 Claims, 8 Drawing Sheets

(56) References Cited

OTHER PUBLICATIONS

De Boer et al., Recent efforts in engineering microbial cells to produce new chemical compounds, Curr Opin Chem Biol., 2003, 7(2):273-8.
Cropp et al., Recent developments in the production of novel polyketides by combinatorial biosynthesis, Biotechnol Genet Eng Rev., 2002, 19:159-72.
Kendrew et al., Recombinant strains for the enhanced production of bioengineered rapalogs, Metab Eng., 2013 15:167-73.
Jung et al. Heterologous expression of tylosin polyketide synthase and production of a hybrid bioactive macrolide in Streptomyces venezuelae, Appl Microbiol Biotechnol., 2006, 72(4):763-9.
Yoon et al., Generation of multiple bioactive macrolides by hybrid modular polyketide synthases in Streptomyces venezuelae, Chem Biol. 2002, 9(2):203-14.
Menzella et al., Rational design and assembly of synthetic trimodular polyketide synthases, Chem Biol. 2007, (2):143-51.
Starcevic et al., Recombinatorial biosynthesis of polyketides, J Ind Microbiol Biotechnol., 2012, 39(3):503-11.

* cited by examiner

A: Typical organisation of a PKS module

B: Typical organisation of a NRPS module

Structure of rapamycin:

SEQUENCE LISTING

```
<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
cgacgaattc catcgcgccc cggcccgcca gg                                      32

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
ttgtccggcc gggtgtcgta cgtcttcgg                                          29

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ccagggacga ggagcacgcc gtgtccatcg                                         30

<210> SEQ ID NO 4
<211> LENGTH: 37
<212> TYPE: DNA
<213> ORGANISM: Artificial Sequence
<220> FEATURE:
<223> OTHER INFORMATION: Primer

<400> SEQUENCE: 4
ggggtgtaga ggctagccgc cctggcaccg gccgagc                                 37

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
gtatctagaa agatctagta cccgggttgt ggcggtgccg agg                          43

<210> SEQ ID NO 6
<211> LENGTH: 38
<212> TYPE: DNA
```

```
<213> ORGANISM: Artificial Sequence
<220> FEATURE:
<223> OTHER INFORMATION: Primer

<400> SEQUENCE: 6
tcaggccgcc tcgggcgtgt cggttgtcat caagatgg                              38

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
gacggctcat ccacgtgcag ggtgcgggga acc                                   33

<210> SEQ ID NO 8
<211> LENGTH: 37
<212> TYPE: DNA
<213> ORGANISM: Artificial Sequence
<220> FEATURE:
<223> OTHER INFORMATION: Primer

<400> SEQUENCE: 8
gtctaagctt tccccaccga ccgtggctgg gacgtcg                               37

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
cgcgaattcg gagaaaccgg caccgtccgc actgtccgc                             39

<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10
cgtaaagctt ggagacgaca ccgtcaccgg caccgctgtg                            40
```

RAPAMYCIN ANALOGUES AND THEIR PHARMACEUTICAL USE

This application is a §371 application of PCT/GB2014/052091, filed Jul. 9, 2014, which in turn claims priority to GB Application 1312318.7, filed Jul. 9, 2013. The entire disclosure of each of the foregoing applications is incorporated by reference herein.

BACKGROUND OF THE INVENTION

Rapamycin and its analogues bind tightly to the FK506-binding protein (FKBP) family of immunophilins (Cao & Konsolaki, 2011; Gerard et al., 2011). The FKBP family consists of proteins with a variety of protein-protein interaction domains and versatile cellular functions (Kang et al., 2008). All FKBPs contain a domain with prolyl cis/trans isomerase (PPIase) activity. Binding of rapamycin or analogues to this domain inhibits their PPIase activity while mediating immune suppression through inhibition of mTOR. The larger members, FKBP51 and FKBP52, interact with Hsp90 and exhibit chaperone activity that is shown to regulate steroid hormone signalling. From these studies it is clear that FKBP proteins are expressed ubiquitously but show relatively high levels of expression in the nervous system. Consistent with this expression, FKBPs have been implicated with both neuroprotection and neurodegeneration (Cao & Konsolaki, 2011; Gerard et al., 2011; Bove et al., 2011; Kang et al., 2008). Rapamycin is a nM inhibitor of the PPIase activity of several neurophilins including FKBP12 and FKBP52, and binding to these proteins has been shown to contribute to their neuroprotective effects (Ruan et al, 2008). FKBP52 binds Tau, and Tau protein overexpression is linked to inhibition of neurite outgrowth and neuroprotection (Chambraud et al., 2010). FKBP52 controls chemotropic guidance of neural growth cones via regulation of TRPC1 channel opening (Shim et al., 2009). These data provide a link for the neurite outgrowth promoting, axonal regeneration and neuroprotective effects observed for FKBP52 knockdown/inhibition. FKBP12 has been proposed many times as the major mediator of the neuroprotective effects of immunophilins, for example FK506 protection against oxygen-glucose deprivation induced damage was not present when an anti-FKBP12 antibody was added (Labrande et al., 2006), expression of FKBP12 is increased in the brain of patients with Parkinson's Disease, Alzheimer's disease and some forms of dementia (Avramut et al., 2002). It has also been implicated as the most potent enhancer of α-synuclein aggregation (Gerard et al., 2010, Deleersnijder et al., 2011).

Macrophage infectivity potentiators (MIPs) are close homologues of human FKBPs and have been shown to be important for virulence in some bacteria, such as *Burkholderia* sp., and inhibition of these MIPs by rapamycin has been shown (Norville et al, 2011). Other bacteria containing MIPs include *Neisseria* sp. (Leuzzi et al. 2005), *Legionella* sp., *Pseudomonas* sp., *Xanthomonas* sp. (Zang et al., 2007), *Acetinobacter* sp., *Chlamydia* sp., *Salmonella* sp. and *Klebsiella* sp. They are also important in certain parasites, including *Trypanosoma* sp. (Moro et al. 1995). Inhibition of bacterial virulence factors is potentially an antimicrobial strategy that is nondestructive to the bacteria. It has been proposed that virulence inhibitors could constitute a new class of antibiotics (Travis et al. 2000). By affecting virulence mechanisms without challenging bacterial viability directly, these antibiotic agents would potentially place little or no pressure on the bacterial cell for the emergence of resistant strains (Crunkhorn 2008). However, rapamycin also inhibits the mTOR pathway, leading to potent immunosuppressive activity. This is obviously an undesirable side-effect for an FKBP- or MIP-inhibiting compound.

One object of the invention is therefore to identify rapamycin analogues which are potent FKBP (including but not limited to FKBP12, FKBP38, FKBP51 and FKBP52 or FKBP11, FKBP14, FKBP1, FKBP8, FKBP4, FKBP5, FKBP10, FKBP9, FKBP6, FKBP7, FKBP10, FKBP3 or FKBP2) and/or MIP inhibitors, but with reduced or modulated mTOR inhibitory activity, such as shown by reduced activity in a t-cell proliferation assay (e.g. a PLP t-cell proliferation assay or MLR assay) or an increased ratio of this assay to FKBP inhibition (e.g. PLP $IC_{50}$/FKBP $IC_{50}$) as compared to rapamycin or known rapamycin analogues.

In particular, reduction of mTOR inhibition with maintenance or increase in inhibition of bacterial MIPs could enable broad spectrum virulence inhibition, with activity against bacterial strains resistant to many current antibiotics, where there is a dire need for new therapies (especially *Klebsiella* sp., *Acetinobacter* sp., *Neisseria* sp., *Legionella* sp. and *Pseudomonas* sp.).

SUMMARY OF THE INVENTION

In one aspect, the present invention provides analogues of rapamycin which are coded for by a PKS expanded or contracted in module number. These analogues may therefore have expanded or contracted ring sizes, or be linear variants due to altered or lack of cyclisation.

Thus in one aspect of the invention there is provided a rapamycin analogue of formula (I) or a pharmaceutically acceptable salt thereof.

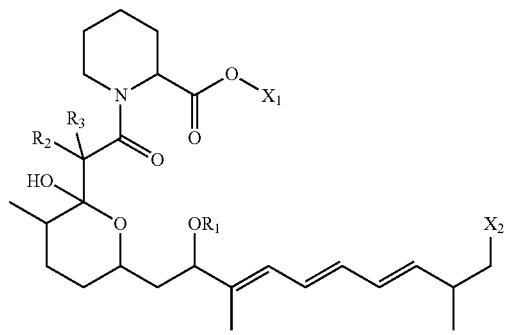

(I)

wherein:
$R_1$ represents Me or H;
$R_2$ and $R_3$ represent H or $R_2$ and $R_3$ taken together represent keto;
$X_1$ and $X_2$ are connected by a moiety selected from:

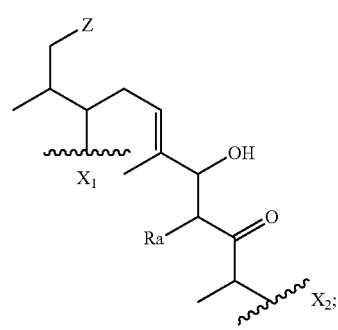

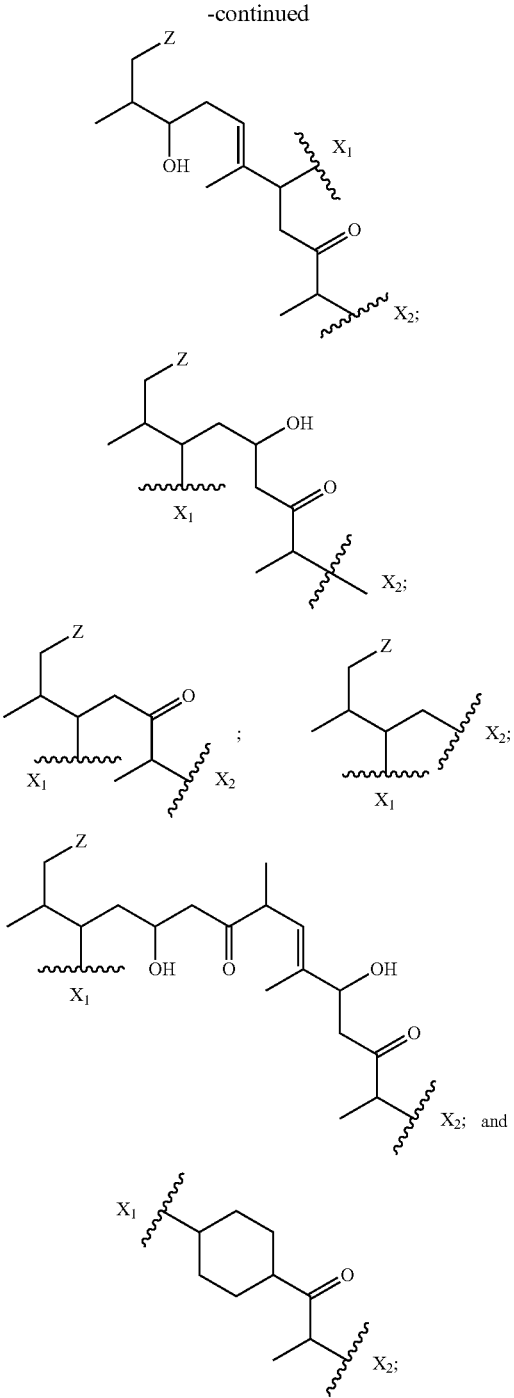

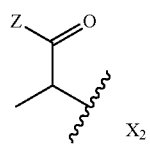

and $X_1$ is H;
or X1 and X2 are connected as follows:

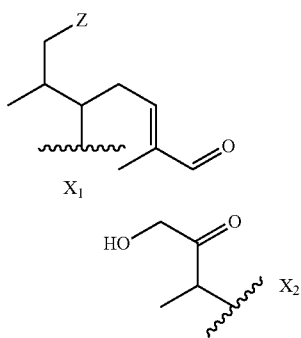

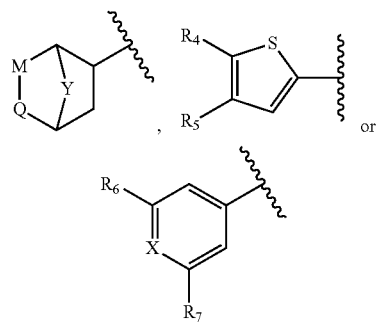

or $X_1$ represents H and $X_2$ represents Z;
$R_a$ is selected from H, OH and OMe;
Z represents

[structures shown]

Y represents methylene or is absent;
M is selected from bond, $CH_2$, CHMe, CHF, CHOH, $CH_2CH_2CH(OMe)$, $CMe_2$, CHEt and $CF_2$;
Q is selected from bond, $CH_2$, CHMe, CHF, CHOH, $CH_2CH_2$, O, S, $CHCH_2OH$, C(OH)Me and CH(OMe);
provided that:
(i) when Q is not O or S then one of M or Q must represent CHOH $CHCH_2OH$ or C(OH)Me; and
(ii) if Q is O or S, then M does not represent CHF, $CF_2$, CHOMe, CHOH; and
(iii) M and Q do not both represent bond;
either $R_4$ represents $CH_2OH$ and $R_5$ represents H or $R_4$ represents H and $R_5$ represents $CH_2OH$; and
either $R_6$ represents OH, $R_7$ represents $NH_2$ or H and X represents CH; or $R_6$ represents H, $R_7$ represents H and X represents N.

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "strain(s)" refers to bacterial strains including, but not limited to, *Streptomyces rapamycinicus* NRRL 5491 and its derivatives.

As used herein the term "Polyketide synthase" or "PKS" refers to a protein with modular enzymatic activities which can lead to production of a polyketide under certain conditions.

As used herein the term "Non-ribosomal peptide synthetase" or "NRPS" refers to a protein with modular enzymatic activities which can lead to production of a non-ribosomal peptide under certain conditions.

As used herein the term "Module" refers to a section of a polyketide synthase or non-ribosomal peptide synthetase protein containing one or more domains, involved in at least one round (typically one round) of chain extension or chain transfer (more commonly chain extension), including but not limited to a ketosynthase, ketoreductase, dehydratase, enoyl reductase, acyl carrier protein, acyl transferase, thioesterase, condensation, thiolation, peptidyl carrier protein, methylation or adenylation domain. See FIG. 1 for the organisation of a typical PKS and NRPS module and FIGS. 6 and 7 for organisation of modules within a typical PKS and NRPS.

As used herein the term "Domain" refers to a section of a polyketide synthase or non-ribosomal peptide synthetase protein containing a single enzymatic activity, including but not limited to a ketosynthase, ketoreductase, dehydratase, enoyl reductase, acyl carrier protein, acyl transferase, thioesterase, condensation, thiolation, peptidyl carrier protein, methylation or adenylation domain. See FIG. 1 for the organisation of domains within a typical PKS and NRPS module and FIGS. 6 and 7 for organisation of domains within a typical PKS and NRPS.

Percentage identity determinations can be performed for nucleic acids using BLASTN or standard nucleotide BLAST using default settings (Match/Mismatch scores 1, −2) Gap costs linear, Expect threshold 10, Word size 28 and match matches in a query range 0) and for proteins using BLAST using default settings (Expect threshold 10, Word size 3, Max matches in a query range 0, Matrix Blosum62, Gap costs Existence 11, extension 1 and conditional compositional score matrix adjustment).

As used herein the term "Co-linear" refers to open reading frames coding for one or more modules of PKS or NRPS which are transcribed in the same direction.

As used herein the term "Virulence inhibition" refers to inhibition of the pathogenicity of bacteria. This may include, but is not limited to, reduction in cytotoxicity of bacteria, improvements in activity of co-dosed antibiotics, especially against resistant bacteria, reduction in bacterial adhesion, reduction in bacterial colonization, reduction in production of bacterial factors affecting host immune responses, reduction in bacterial invasion and reduction in production of bacterial toxins.

As used herein the term "Virulence inhibitor" refers to a compound of the invention which when exposed to bacteria can lead to virulence inhibition.

DETAILED DESCRIPTION OF THE INVENTION

Figure 1:
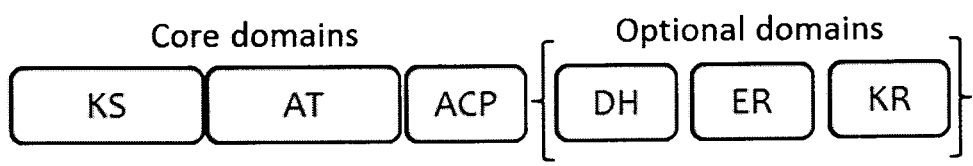
FIG. 1: A: Pictorial representation of a typical PKS module with core Ketosynthase (KS), Acyl Transferase (AT), Acyl Carrier Protein (ACP) domains and optional Ketoreductase (KR), Enoyl Transferase (ER) and Dehydratase (DH) domains. B: Pictorial representation of a typical NRPS module with core Condensation (C), Adenylation (A), Thiolation or Peptidyl Carrier Protein (T) domains and optional Epimerization (E) and Methylation (M) domains.
Figure 1:
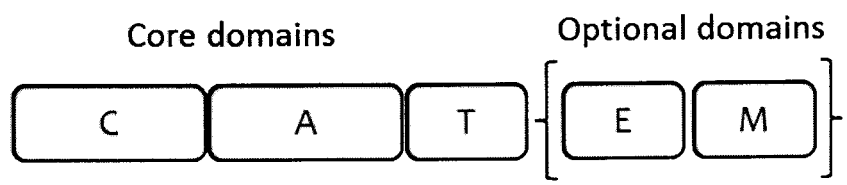
Figure 2:
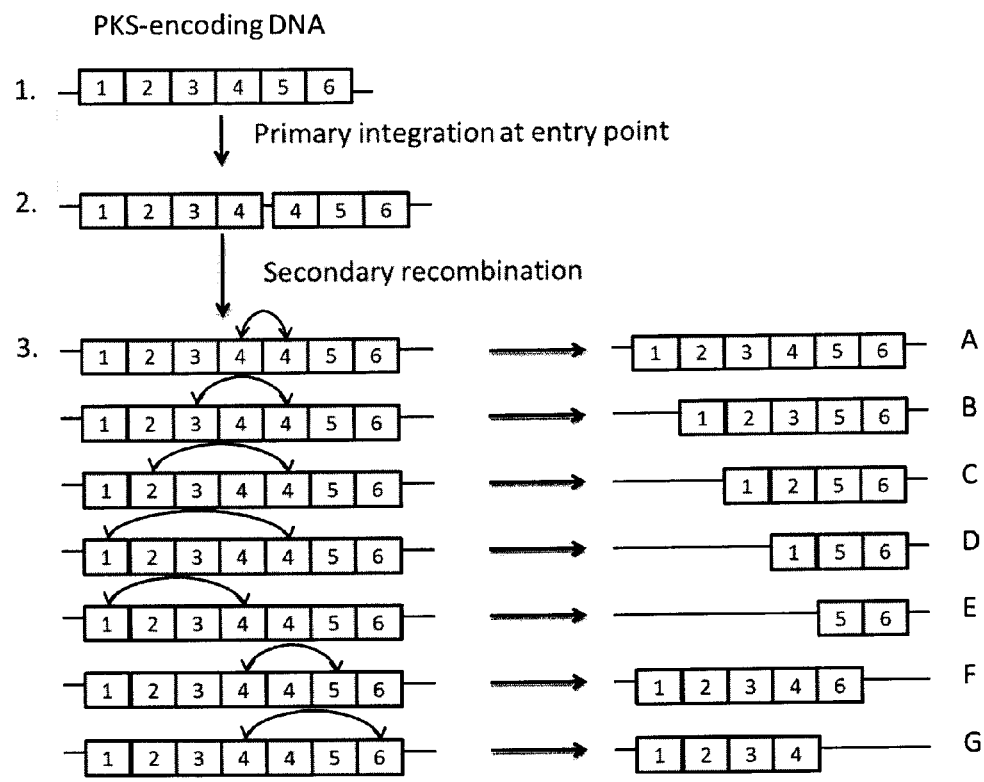
FIG. 2: Pictorial representation of recombineering process with primary integration using entry point DNA (1) in DNA encoding module 4 of the PKS, followed by representation of a series of different potential secondary recombination outputs: wild type (a) and removal of 1 (B, F) 2 (C, G), 3 (D) and 4 (E) modules.
Figure 3:
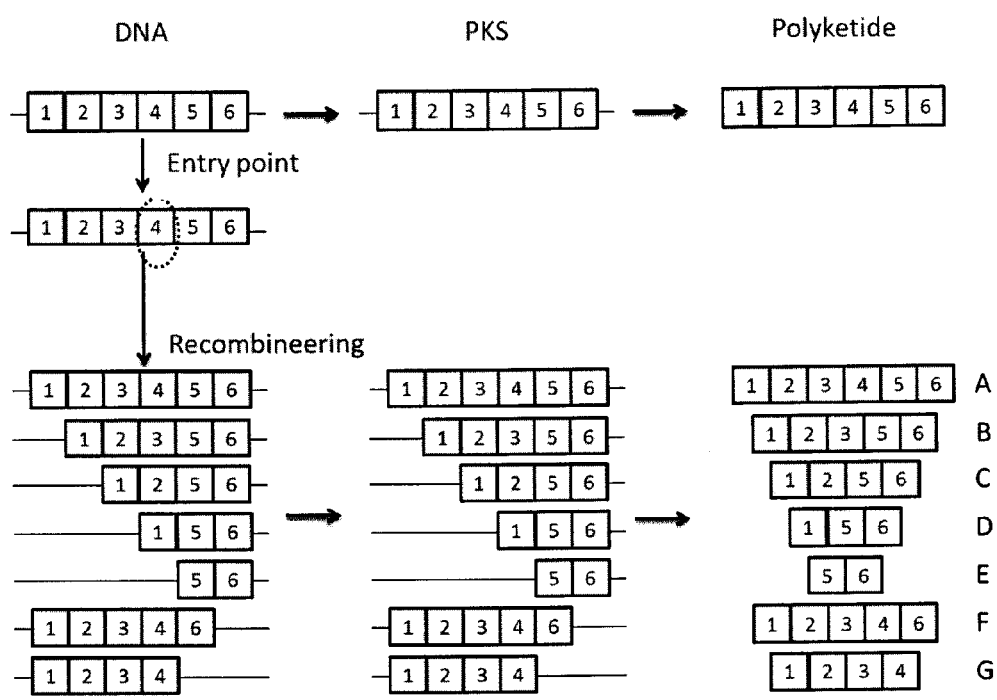
FIG. 3: Pictorial representation of recombineering process and one to one correspondence of DNA, PKS modules and the final polyketide, following a series of different potential secondary recombination outputs: wild type (a) and removal of 1 (B, F) 2 (C, G), 3 (D) and 4 (E) modules.
Figure 4:
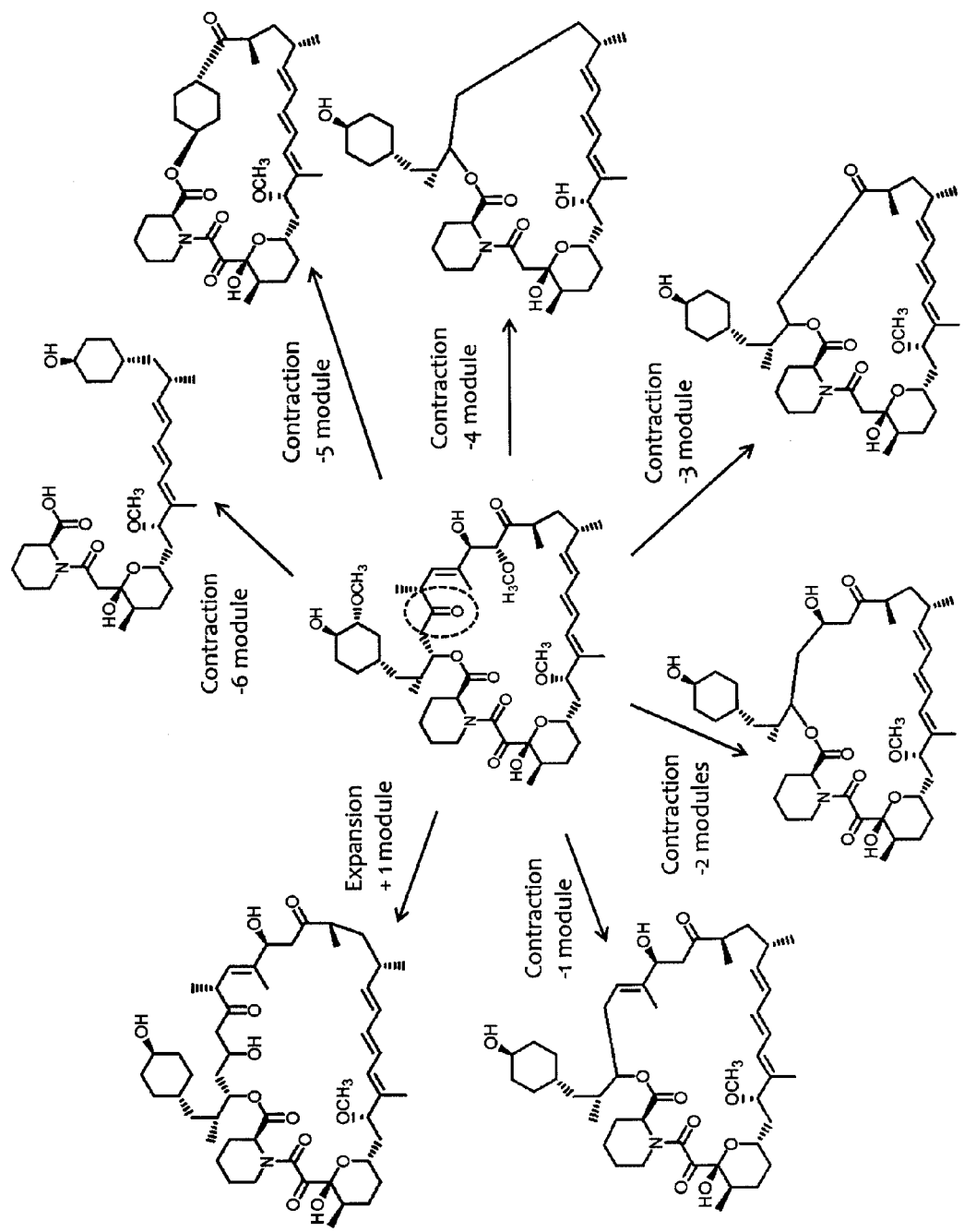
FIG. 4: Representation of the outputs from recombineering on the rapamycin PKS following initial recombination into DNA encoding module 3 of the rapamycin PKS.
Figure 5:
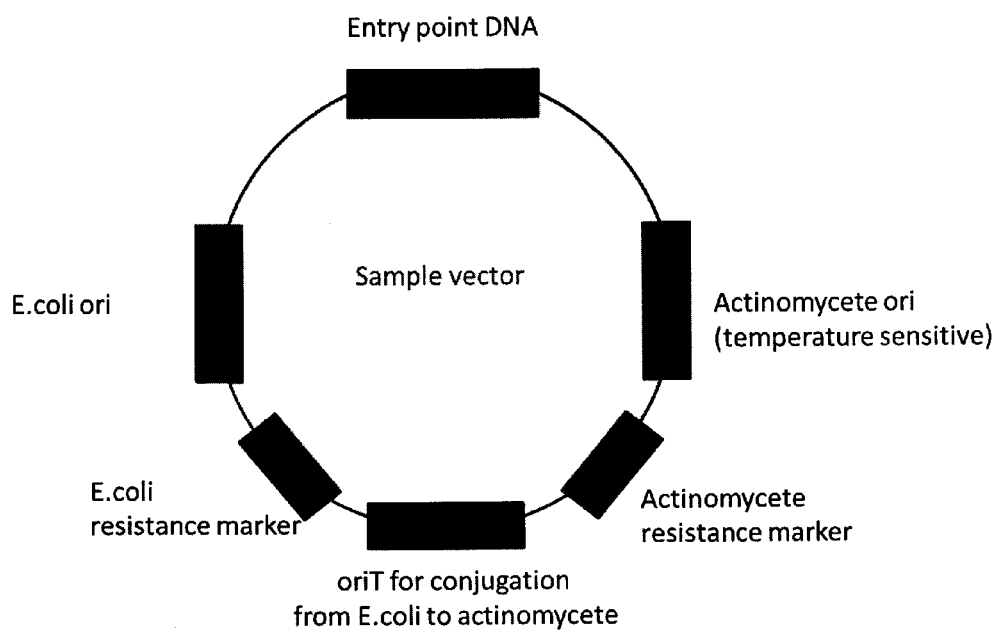
FIG. 5: Representation of a sample vector to carry out recombineering in an actinomycete host containing a PKS or NRPS cluster, with conjugation from E. coli to the actinomycete.
Figure 6:
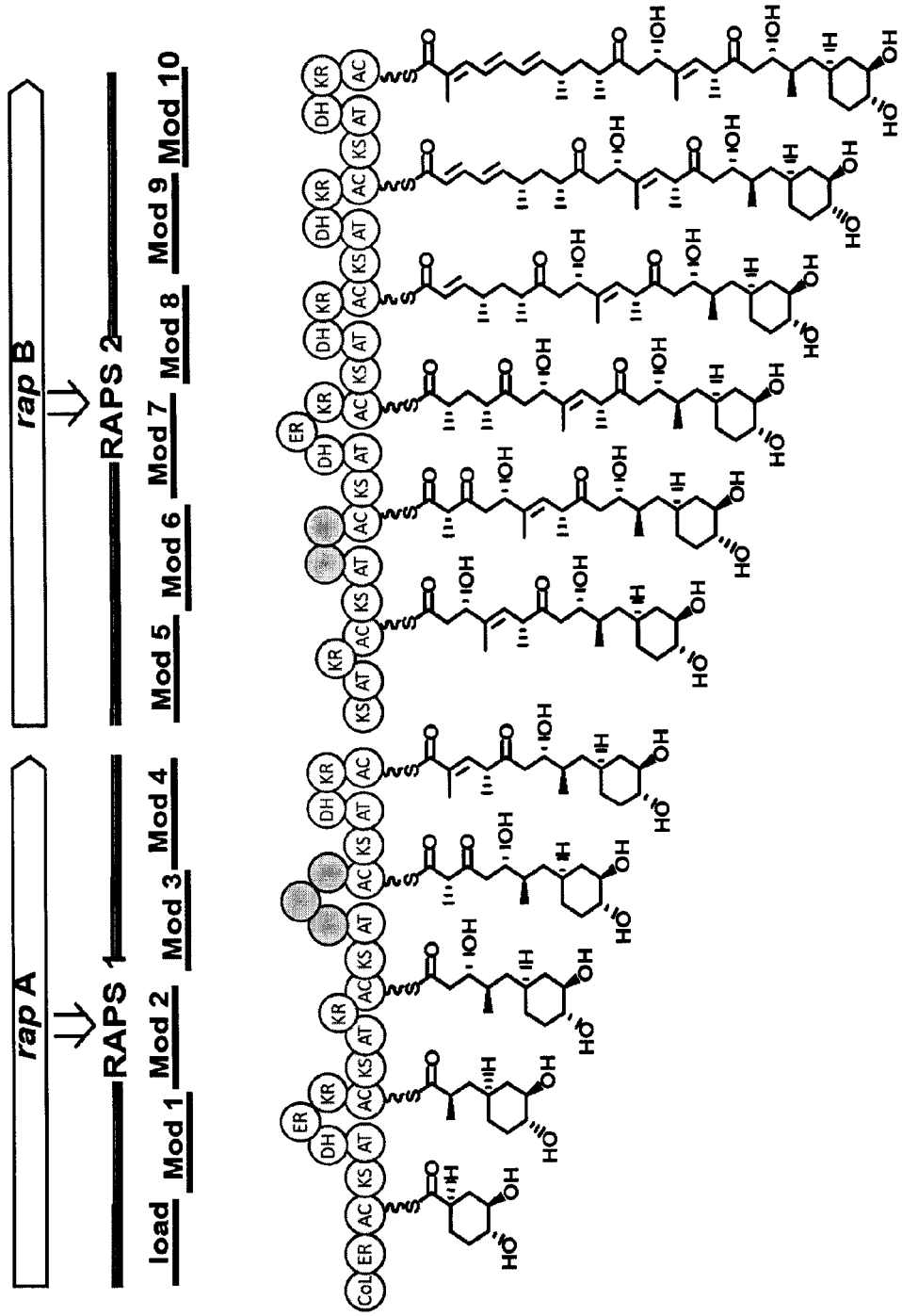
FIG. 6: Representation of the rapamycin PKS, showing modular arrangement of KS, AT, ACP (abbreviated as 'AC'), DH, ER, KR and Thioesterase (TE) domains, together with the structure of rapamycin
Figure 6:
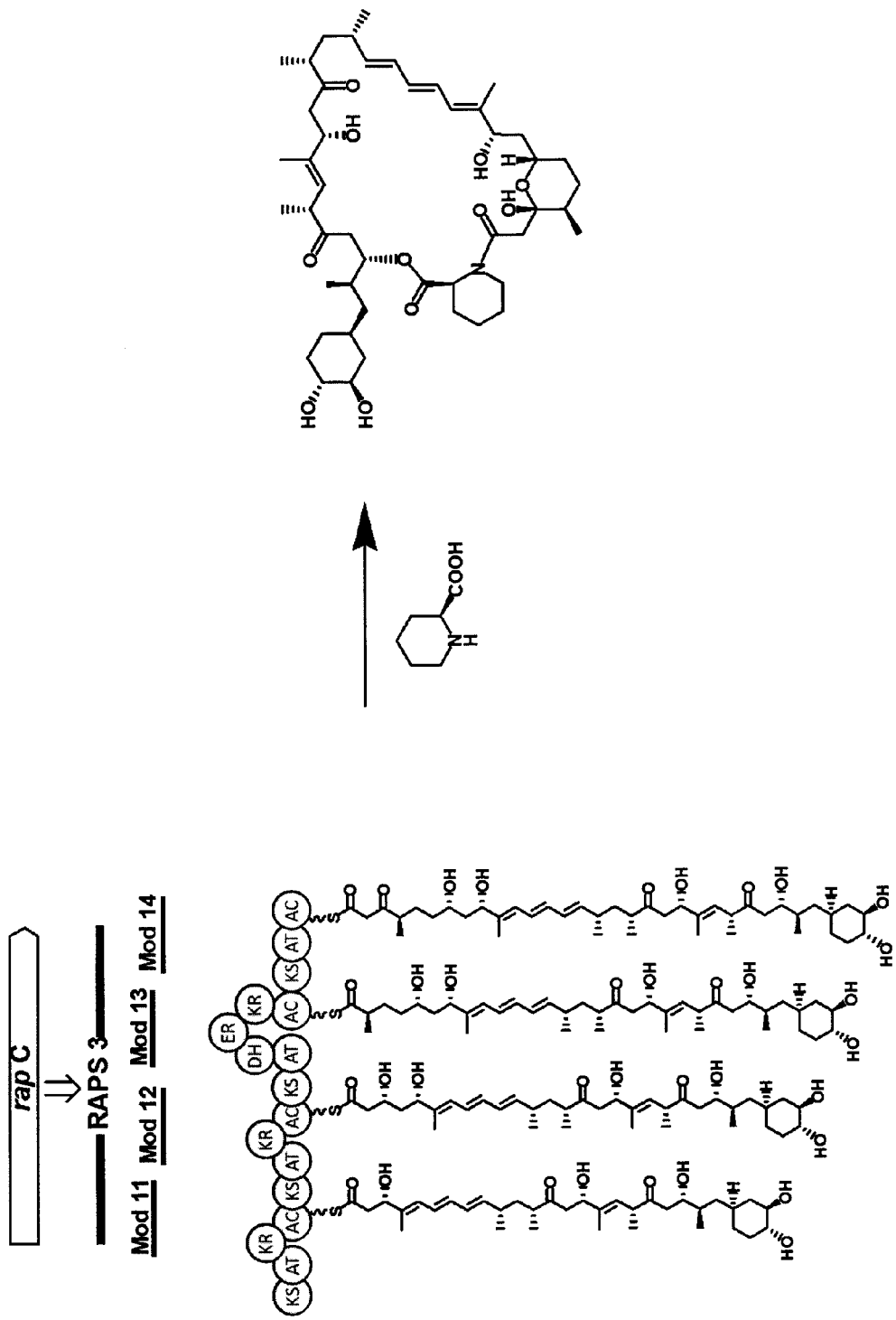
Figure 6:
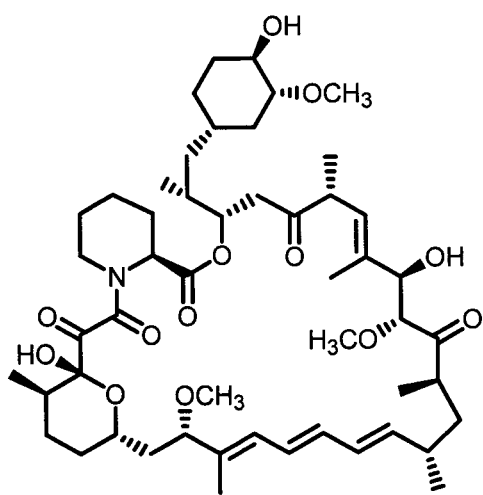

Novel or newly isolated compounds (polyketides or non-ribosomal peptides) produced by cells and strains described herein ("compounds of the invention" or "rapamycin analogues of the invention") are of interest. Thus compounds of formula (I) as described above are an aspect of the invention.

$R_1$ preferably represents methyl.

$R_2$ and $R_3$ preferably together represent keto.

In one particularly suitable embodiment, $X_1$ and $X_2$ are connected as follows:

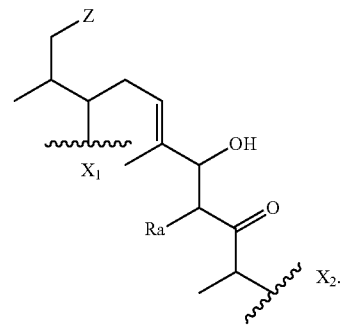

In another suitable embodiment, $X_1$ and $X_2$ are connected as follows:

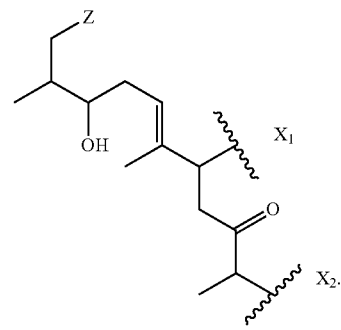

In another particularly suitable embodiment, $X_1$ and $X_2$ are connected as follows:

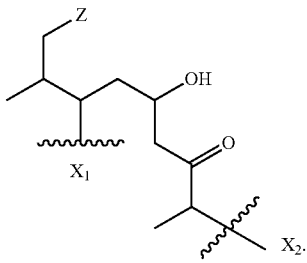

In another particularly suitable embodiment, $X_1$ and $X_2$ are connected as follows:

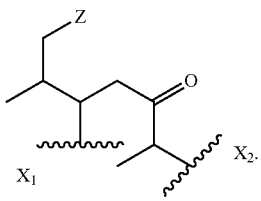

In another suitable embodiment, $X_1$ and $X_2$ are connected as follows:

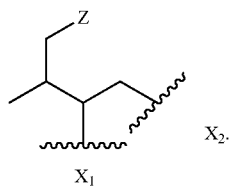

In another suitable embodiment, $X_1$ and $X_2$ are connected as follows:

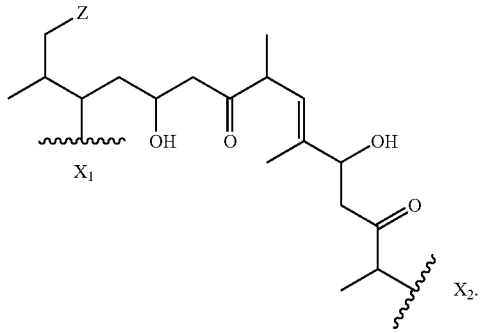

In another suitable embodiment, $X_1$ and $X_2$ are connected as follows:

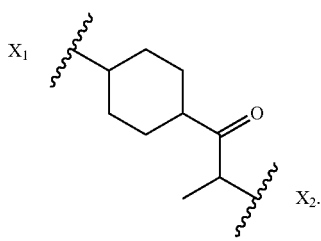

In another suitable embodiment, $X_2$ is connected as follows:

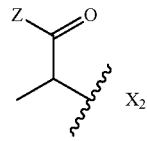

and $X_1$ is H.

In another suitable embodiment, $X_1$ and $X_2$ are connected as follows:

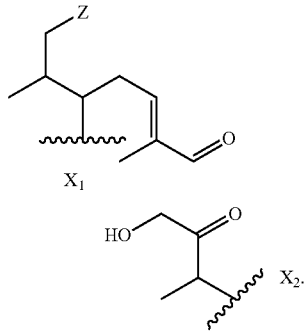

In another suitable embodiment, $X_1$ represents H and $X_2$ represents Z.

In a suitable embodiment, Z represents

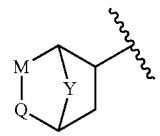

e.g. is selected from 4-hydroxycyclohexane, 3-methoxy-4-hydroxy-cyclohexane and 3,4-dihydroxycyclohexane.

In a suitable embodiment, Z represents

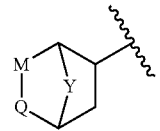

and

Y represents methylene or is absent, M represents $CH_2$ and Q represents CHOH; or Y is absent; M represents CHOMe and Q represents CHOH; or Y is absent, M represents CHF and Q represents CHOH.

In other suitable embodiments, Z represents

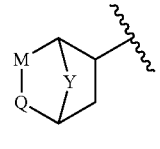

and

Y is absent, M represents CHOH and Q represents $CH_2$; or

Y is absent, M represents $CH_2$ and Q represents C(OH)Me; or

Y is absent, M=bond; Q=CHOH; or

Y is absent, M=$CH_2CH_2$; Q=CHOH; or

Y represents methylene, M represents $CH_2CH_2$, Q represents CHOH; or

Y is absent, M represents $CH_2$, Q represents O; or
Y is absent, M represents $CH_2$, Q represents S; or
Y represents methylene, M represents $CMe_2$, Q represents CHOH; or
Y is absent, M represents CHOH; Q represents CHOH; or
Y is absent, M represents CHMe; Q represents CHOH; or
Y is absent, M represents $CF_2$; Q represents CHOH; or
Y is absent, M represents CHEt; Q represents CHOH.

In other suitable embodiments, Z represents

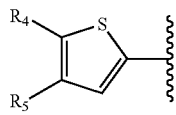

and
$R_4$ represents $CH_2OH$ and $R_5$ represents H; or
$R_4$ represents H and $R_5$ represents $CH_2OH$.

In other suitable embodiments, Z represents

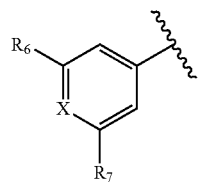

and
$R_6$ represents OH, X represents CH and $R_7$ represents H; or
$R_6$ represents OH, X represents CH and $R_7$ represents $NH_2$; or
$R_6$ represents H, $R_7$ represents H and X represents N.

In an embodiment, Z represents the moiety Za where Za is defined by the moiety derived from incorporation of an acid Za-COON listed as Feed code A, B, C, D, E, F, G, H, I, J, K, L, M, N, O, P, Q, R, S, T, U, V, W, X, A1, B1, C1, E1 or G1 in Table 1. For instance, in relation to Feed code A of Table 1, Z represents a moiety derived from incorporation of cyclohexanecarboxylic acid e.g. Z represents 4-hydroxycyclohexanyl.

In an embodiment, Z represents the moiety Zb where Zb is defined by the moiety of an ester Zb-COOMe listed as Feed code D1 or F1 in Table 1.

In an embodiment, Z represents one of the aforementioned Za or Zb groups in hydroxylated form i.e. substituted by one or two (e.g. one) hydroxyl groups.

Rapamycin analogues of the invention can be prepared as described in the Examples. Thus, in general, BIOT-4827 or an isolated strain thereof can be fed a suitable starter acid (see e.g. Table 1 for a non-limiting list of acids) and cultured under suitable conditions which will be well known to a person skilled in the art such that rapamycin analogues are generated. The rapamycin analogues may be isolated and purified by conventional means.

Rapamycin analogues of the invention are expected to be useful as pharmaceuticals.

The aforementioned compounds of the invention or a formulation thereof may be administered by any conventional method for example but without limitation they may be administered parenterally (including intravenous administration), orally, topically (including buccal, sublingual or transdermal), via a medical device (e.g. a stent), by inhalation, or via injection (subcutaneous or intramuscular). The treatment may consist of a single dose or a plurality of doses over a period of time.

Whilst it is possible for a compound of the invention to be administered alone, it is preferable to present it as a pharmaceutical formulation, together with one or more acceptable carriers. Thus there is provided a pharmaceutical composition comprising a compound of the invention (suitable in a therapeutically effective amount) together with one or more pharmaceutically acceptable diluents or carriers. The diluents(s) or carrier(s) must be "acceptable" in the sense of being compatible with the compound of the invention and not deleterious to the recipients thereof. Examples of suitable carriers are described in more detail below.

The compounds of the invention may be administered alone or in combination with other therapeutic agents. Co-administration of two (or more) agents may allow for significantly lower doses of each to be used, thereby reducing the side effects seen. It might also allow re-sensitisation of a disease, such as cancer, to the effects of a prior therapy to which the disease has become resistant. It might also reduce the chance of developing resistance to an infectious agent, such as in viral diseases. There is also provided a pharmaceutical composition comprising a compound of the invention and a further therapeutic agent together with one or more pharmaceutically acceptable diluents or carriers.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatine and acacia. Additionally, lubricating agents such as magnesium stearate, stearic acid, glyceryl behenate and talc may be included.

Solid compositions of a similar type may also be employed as fillers in gelatine capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerine, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatine, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatine and glycerine, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compounds of the invention may also be administered using medical devices known in the art. For example, in one embodiment, a pharmaceutical composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art. The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Rapamycin analogues disclosed herein are expected to be useful inter alia in the treatment or prevention of human or animal diseases caused by infection with a pathogenic microbe (especially gram negative bacteria) selected from *Burkholderia* sp. (especially *Burkholderia pseudomallei*), *Legionella* sp., *Chlamydia* sp., *Pseudomonas* sp. (especially *Pseudomonas aeruginosa*), *Klebsiella* sp., (especially *Klebsiella pneumoniae*) and *Neisseria* sp. (especially *Neisseria gonorrhoeae*). Rapamycin analogues disclosed herein are expected to be useful inter alia in the treatment or prevention of human or animal diseases caused by infection with *Actinobacter* sp. and *Coxiella* sp. Rapamycin analogues disclosed herein are expected to be useful inter alia in the treatment or prevention of human or animal diseases caused by infection with *Trypanosoma* sp. (especially *Trypanosoma cruzi*) and in the treatment of plant diseases caused by *Xanthomonas* sp. (especially *Xanthomonas campestris*). Thus the invention embraces a method of treatment or prevention of a human or animal disease caused by infection by a pathogenic microbe (especially one of the aforementioned microbes) comprising administering to a human or animal subject in need thereof a therapeutically effective amount of a rapamycin analogue of the present invention. There is also provided a rapamycin analogue of the present invention for use in treating or preventing a disease caused by infection by a pathogenic microbe (especially one of the aforementioned microbes). There is also provided us of a rapamycin analogue of the present invention in the manufacture of a medicament for the treatment or prevention of a disease caused by infection by a pathogenic microbe (especially one of the aforementioned microbes). There is also provided use of a rapamycin analogue of the present invention for treating or preventing plant diseases caused by *Xanthomonas* sp. (especially *Xanthomonas campestris*). There is also provided a method of treatment or prevention of a plant disease caused by infection caused by *Xanthomonas* sp. (especially *Xanthomonas campestris*) comprising administering to a plant in need thereof an effective amount of a rapamycin analogue of the present invention. The invention also provides a pharmaceutical composition comprising a compound according to the invention together with a pharmaceutically acceptable diluent or carrier further comprising a second or subsequent active ingredient, especially an active ingredient indicated for the treatment of microbial (e.g. bacterial) infections such as *Burkholderia* sp. (especially *Burkholderia pseudomallei*), *Legionella* sp., *Chlamydia* sp., *Pseudomonas* sp. (especially *Pseudomonas aeruginosa*), *Klebsiella* sp., (especially *Klebsiella pneumoniae*), *Neisseria* sp. (especially *Neisseria gonorrhoeae*), *Acetinobacter* sp., and *Coxiella* sp.; and also *Trypanosoma* sp. (especially *Trypanosoma cruzi*). The invention also provides a rapamycin analogue according to the invention for use as a pharmaceutical in combination (for simultaneous or separate administration) with a second or subsequent active ingredient, especially an active ingredient indicated for the treatment of microbial (e.g. bacterial) infections such as *Burkholderia* sp. (especially *Burkholderia pseudomallei*), *Legionella* sp., *Chlamydia* sp., *Pseudomonas* sp. (especially *Pseudomonas aeruginosa*), *Klebsiella* sp., (especially *Klebsiella pneumoniae*), *Neisseria* sp. (especially *Neisseria gonorrhoeae*), *Acetinobacter* sp., and *Coxiella* sp.; and also *Trypanosoma* sp. (especially *Trypanosoma cruzi*). Example second or subsequent active ingredients include antibiotics such as amikacin, gentamicin, kanamycin, neomycin, netilmicin, tobramycin, paromomicin, streptomycin, spectinomycin, ertapenem, doripenem, imipenem, meropenem, doxycycline, demeclocycline, minocycline, oxytetracycline, tetracycline, cefepime, teicoplanin, vancomycin, telavancin, cefexime, cefdinir, cefditoren, cefoperazone, cefotaxime, cefpodoxime, ceftazidime, ceftibuten, ceftizoxime, ceftriaxone, aztreonam, amoxyxillin, ampicillin, azlocillin, carbenicillin, cloxacillin, dicloxacillin, flucloxacillin, mezlocillin, methicillin, nafcillin, oxacillin, penicillin, temocillin and ticarcillin.

When rapamycin analogues of the invention are intended for use in treatment of plant diseases, the active ingredient may be presented in a composition (e.g. an aqueous spray composition) together with one or more diluents or carriers.

Compounds of the invention may have one or more of the following merits or advantages:

good inhibitory activity against FKBPs (e.g. FKBP12, FKBP38, FKBP51 or FKBP52 or FKBP11, FKBP14, FKBP1, FKBP8, FKBP4, FKBP5, FKBP10, FKBP9, FKBP6, FKBP7, FKBP10, FKBP3 or FKBP2) (e.g. as measured in a PPlase assay);

good inhibitory activity against MIPs (e.g. as measured in the MIP Inhibition Assay);

low or no inhibitory activity against mTOR (e.g. as measured in a PLP assay);

good activity as a virulence inhibitor (e.g. as measured in the Cytotoxicity Reduction Assay or the Antibiotic Combination Assay);

improved therapeutic index e.g. as measured by increased ratio of PLP $IC_{50}$/FKBP $IC_{50}$) as compared to rapamycin or known rapamycin analogues.

EXAMPLES

General Methods

Media

Water used for preparing media was prepared using Millipore Elix Analytical Grade Water purification System 2×TY

| Yeast extract | 10 g/L |
|---|---|
| Tryptone | 16 g/L |
| Sodium Chloride | 5 g/L |

R6 Conjugation Media.

| For 700 ml | |
|---|---|
| Sucrose | 200 g |
| Dextrin | 10 g |
| Casamino acids | 1 g |
| $MgSO_4 \cdot 7H_2O$ | 0.05 g |
| $K_2SO_4$ | 0.1 g |
| Trace Elements | 1 mL (1 g/L each of $FeSO_4 \cdot 7H_2O$, $MnCl_2 \cdot 4H_2O$, $ZnSO_4 \cdot 7H_2O$, sterilized by filter and stored at room temperature). |
| Agar | 20 g |
| Autoclaved at 121 C., 20 minutes. | |
| Sterile additions (added to 700 mL of well-tempered mixture prepared as above) | |
| 0.65M L-glutamic acid, mono sodium salt | 100 mL (filter sterilised) |
| 0.48M $CaCl_2 \cdot 2H2O$ | 100 mL |
| 0.1M MOPS pH 7.2 | 100 mL |

Plates are poured (~30 mL) and dried extensively in a laminar flow hood before use ISP3 Agar

| | |
|---|---|
| Oatmeal | 20 g/L |
| Bacto Agar | 18 g/L |
| Trace element solution | 1 mL/L (1 g/L each of FeSO$_4$•7H$_2$O, MnCl$_2$•4H$_2$O, ZnSO$_4$•7H$_2$O, sterilized by filter and stored at room temperature). |

Oatmeal is cooked/steamed in the water for 20 min, strained through a muslin and more water added to replace lost volume. Trace elements solution is added and pH adjusted to 7.2 with NaOH. Agar is added before autoclaving at 121° C., 15 minutes.

MMAM Agar

| | |
|---|---|
| Wheat Starch | 10 g/L |
| Corn steep powder | 2.5 g/L |
| Yeast extract | 3 g/L |
| CaCO$_3$ | 3 g/L |
| FeSO$_4$ | 0.3 g/L |
| Adjust to pH 5.8 if needed before sterilisation | |
| Agar | 20 g/L |

RapV7

| | |
|---|---|
| Corn steep solids | 4.0 g/L |
| Nutrisoy | 5.0 g/l |
| Dextrin | 35 g/L |
| Ammonium sulphate | 2.0 g/L, |
| Lactic acid | 1.6 mL/L, |
| Calcium carbonate | 7.0 g/L |
| Adjust to pH 7.5 and Autoclave 121° C., 1 bar, 20 minutes | |
| Add 25 mL/L 40% w/v sterile glucose post sterilisation | |

MD6

| | |
|---|---|
| Nutrisoy | 30 g/L |
| Corn starch | 30 g/L |
| Dextrin | 19 g/L |
| Yeast (whole Allinson) | 3 g/L |
| Corn steep powder | 1 g/L |
| KH$_2$PO$_4$ | 2.5 g/L |
| K$_2$HPO$_4$ | 2.5 g/L |
| Ammonium sulphate | 10 g/L |
| Sodium chloride | 5 g/L |
| Calcium carbonate | 10 g/L |
| MnCl$_2$•4H$_2$O | 10 mg/L |
| MgSO$_4$•7H$_2$O | 2.5 mg/L |
| FeSO$_4$•7H$_2$O | 120 mg/L |
| ZnSO$_4$•7H$_2$O | 50 mg/L |
| MES | 21.2 g/L |

Adjust to pH6.0 and add α-amylase 0.4 mL/L prior to sterilisation (121° C., 1 bar, 20 minutes). Add 50 ml/L 40% w/v sterile fructose and 14 mL/L 14% L-lysine (filter sterilised)

MD6/5-1

| | |
|---|---|
| Nutrisoy | 15 g/L |
| Dextrin | 50 g/L |
| Yeast (whole Allinson) | 3 g/L |
| Corn steep powder | 1 g/L |
| KH$_2$PO$_4$ | 2.5 g/L |
| K$_2$HPO$_4$ | 2.5 g/L |
| Ammonium sulphate | 10 g/L |
| Sodium chloride | 13 g/L |
| Calcium carbonate | 10 g/L |
| MnCl$_2$•4H$_2$O | 3.5 mg/L |
| MgSO$_4$•7H$_2$O | 15 mg/L |
| FeSO$_4$•7H$_2$O | 150 mg/L |
| ZnSO$_4$•7H$_2$O | 60 mg/L |
| SAG471 | 0.5 ml/L |
| Add 15 g/L (28.1% w/v sterile) fructose and 0.5 ml/L sterile 3.75% L-lysine after sterilisation | |

Materials

All molecular biology enzymes and reagents were from commercial sources.

Bacterial Strains and Growth Conditions

*Escherichia coli* DH10B (GibcoBRL) was grown in 2×TY medium or 2×TY agar media as described by Sambrook et al. (1989) and *E. coli* ET12567 (pUZ8002) as described in Paget et al. (1999) in 2×TY medium with kanamycin (25 μg/ml) and chloramphenicol (10 μg/ml). The vector pUC19 was obtained from New England Biolabs. Vector pKC1139 is described in (Bierman et al., 1992). *E. coli* transformants were typically selected for with either 100 μg/mL ampicillin or 50 μg/mL apramycin depending on resistance marker

*Streptomyces rapamycinicus* BIOT-4010 (*Streptomyces rapamycinicus* NRRL5491 in which the rapK gene has been deleted using methodology as described in WO2004/00709 and as described in Kendrew et al., 2013) and its derivatives were maintained on ISP3 agar plates or MAM agar plates at 28° C. Where necessary for selection apramycin was used at 50 μg/mL. Spore stocks of these strains were prepared by growth on ISP3 agar medium for approximately 14-21 days and preserved in 20% w/v glycerol in distilled water at −80° C.

Listing of Phenotypes in BIOT-4827

The following phenotypes are for when grown as described below with the addition of feed A1.

Phenotype A—produces metabolites including one with molecular formula $C_{51}H_{79}NO_{12}$ Phenotype B—produces metabolites including one with molecular formula $C_{46}H_{71}NO_{10}$ Phenotype C—produces metabolites including one with molecular formula $C_{43}H_{67}NO_{10}$ Phenotype D—produces metabolites including one with molecular formula $C_{41}H_{65}NO_{8}$ Phenotype E—produces metabolites including one with molecular formula $C_{37}H_{59}NO_{7}$ Phenotype F—produces metabolites including one with molecular formula $C_{36}H_{53}NO_{8}$ Phenotype G—produces metabolites including one with molecular formula $C_{33}H_{53}NO_{7}$ BIOT-4827, a mixture of strains, has been submitted to the NCIMB strain collection and has deposit number NCIMB 42152. A method for splitting the constituent strains, should it be required, is taught as follows:

*S. rapamvcinicus* BIOT-4827 Separation Method

1) Streak Out the Strain to Obtain Single Colonies.

The spore suspension is streaked out on ISP3 agar at 28° C. for 7-14 days to reveal single colonies. Single colonies are then patched onto fresh ISP3 agar at 28° C. for 7-14 days to achieve good sporulation.

2) Grow Individual Colonies to Prepare to Assess Phenotype

Take a number of individual colonies, prepared as in step 1 and use the fresh spores to inoculate 7 ml seed medium RapV7 (50 mL polypropylene centrifuge tubes (falcon tubes) (cat no. 227261, purchased from Greiner Bio-One Ltd, Stonehouse, Gloucestershire, UK)) closed with foam plugs by transferring an agar plug (5 mm diameter). The inoculated seed medium is incubated with shaking at 300 rpm, 2.5 cm throw at 28° C. for 48 hours. This seed culture (0.5 ml) is transferred to the fermentation medium MD6 (7 mL in falcon tube as before) using a wide bore tip and incubated with shaking at 300 rpm, 2.5 cm throw at 26° C. After 24 hours feed A1 (0.05 ml of stock solution, prepared as described below) is added to the growing cultures. The cultures are incubated with shaking at 300 rpm, 2.5 cm throw at 26° C. for a further 5 days (i.e. a total of 6 days). The broth is then extracted by aliquoting 0.9 ml into a 2 ml eppendorf tube and adding methanol (0.9 ml). The eppendorf is then shaken on a vibrax bed for 30 minutes before the cell debris is removed by centrifugation (13,200 rpm, 10 minutes). An aliquot of the supernatant is then transferred to an LC-vial for LC-MS analysis by the methods described below.

3) Phenotype Analysis

The strain extracts may be analysed by HPLC or LC-MS.

The HPLC system comprises an Agilent HP1100 equipped with a Hyperclone 3 micron BDS C18 130A column 150 mm×4.6 mm (Phenomenex) heated to 50° C. The gradient elution is from 55% mobile phase B to 95% mobile phase B over 10 minutes followed by an isocratic hold at 95% mobile phase B for 2 minutes with a flow rate of 1 mL/min. Mobile phase A is 10% acetonitrile:90% water, containing 10 mM ammonium acetate and 0.1% trifluoroacetic acid, mobile phase B is 90% acetonitrile:10% water, containing 10 mM ammonium acetate and 0.1% trifluoroacetic acid.

LC-MS system comprised an Agilent HP1100 equipped with a Hyperclone 3 micron BDS C18 130A column 150 mm×4.6 mm (Phenomenex) heated to 50° C. coupled to a Bruker Daltonics Esquire 3000 electrospray mass spectrometer. The gradient elution was from 50% mobile phase B to 100% mobile phase B over 10 minutes followed by an isocratic hold at 100% mobile phase B for 3 minutes with a flow rate of 1 mL/min. Mobile phase A was water containing 0.1% formic acid, mobile phase B was acetonitrile containing 0.1% formic acid. Positive negative switching was used over a scan range of 500 to 1000 Dalton.

Isolatable strains may be annotated as follows:

Phenotype A—produces metabolites including one with molecular formula $C_{51}H_{79}NO_{12}$ Phenotype B—produces metabolites including one with molecular formula $C_{46}H_{71}NO_{10}$ Phenotype C—produces metabolites including one with molecular formula $C_{43}H_{71}NO_{10}$ Phenotype D—produces metabolites including one with molecular formula $C_{41}H_{65}NO_8$ Phenotype E—produces metabolites including one with molecular formula $C_{37}H_{59}NO_7$ Phenotype F—produces metabolites including one with molecular formula $C_{36}H_{53}NO_8$ Phenotype G—produces metabolites including one with molecular formula $C_{33}H_{53}NO_7$ Alternatively, the BIOT-4827 mixture could be grown and separate metabolites isolated from a single mixed culture broth, using standard methods.

DNA Manipulation and Sequencing

DNA manipulations, PCR and electroporation procedures were carried out as described in Sambrook et al. (1989). Automated DNA sequencing was carried out at a contract service provider.

Conjugation of *Streptomyces rapamycinicus*

*Escherichia coli* ET12567, harbouring the plasmid pUZ8002 was transformed with the desired plasmid by electroporation to generate the *E. coli* donor strain for conjugation. This strain was used to transform *Streptomyces rapamycinicus* by spore conjugation as described below.

Fresh spores were harvested in water or 20% glycerol from plates of *Streptomyces rapamycinicus*. Alternatively frozen spore stocks were used. These spores were washed in 2TY and then resuspended in 0.25 ml 2T×Y and were heat-shocked at 50° C. for 10 minutes in a water bath. These were then mixed with the *E. coli* donor strain which had been grown (with appropriate antibiotics) to an optical density of approximately 0.4 and washed twice with 2TY before resuspending in 0.25 ml 2T×Y. The mixture of strains wasplated onto R6 medium and incubated at 37° C. (for plasmids with pKC1139 background). After 2-3 hours the plates were overlaid with nalidixic acid (final in-plate concentration 25 µg/mL) and after a further 18 hours with apramycin sulphate (final in-plate concentration 50 µg/mL). For conjugation of plasmids to an attachment site conjugation plates were incubated at 28° C. overnight before and overlaying sequentially with first nalidixic acid (final in-plate concentration 25 µg/mL) and apramycin sulphate (final in-plate concentration 50 µg/mL)

FKBP12 PPlase Assay

The assay was conducted at 10° C. in 50 mM Tris buffer at pH8.0, 50 µM DTT, 100 mM NaCl, 0.005% NP40 with 6 nM FKBP12 and 60 µM substrate (SUC-ALPF-pNA, diluted from 20 mg/ml stock in 0.5M LiCl/TFE). The $K_m$ for the substrate was determined to be approximately 188 µM. The first order rate equation was fitted to the absorbance data to obtain a rate constant. A catalytic rate ($K_{enz}$) was calculated from the enzymatic rate minus the background rate. $K_{enz}$ v inhibitor concentration was plotted to obtain the Ki value.

Murine PLP T Cell Proliferation Assay

Activity of mTOR inhibitors was measured in two different antigen-specific murine T cell proliferation assays (as described in Young et al., 2000). In the first assay, lymph nodes obtained from SJL/J mice immunized with PLP 139-151 encephalitogenic peptide, are re-stimulated in culture and assayed for a secondary proliferation response to the same peptide. In a second type of assay, lymph nodes obtained from PLP TCR transgenic mice are simulated with PLP peptide in culture in a primary stimulation assay.

MIP Inhibition Assay

To test for inhibition of MIPs from one or more species by compounds of the invention, a protease-couple PPlase assay may be used, as described in Norville et al., 2001 or Norville et al., 2013. Briefly, 10 nM recombinant MIP protein is incubated for 6 min at 10° C. in 1.2 ml 35 mM HEPES buffer (pH 7.8) with succinyl-Ala-Phe-Pro-Phe-p-nitroanilide (10 mg/ml; Bachem). Chymotrypsin (Sigma) is added to the cuvette at a final concentration of 0.8 mg/ml and mixed. Hydrolysis of the substrate is measured at 390 nm using a Shimadzu 1800 UV/visible spectrophotometer at 1-s intervals until there is no further change in absorbance. For inhibition measurements, recombinant MIP protein is pre-incubated with various concentrations of test article from 30 nM to 1 nM for 6 min prior to the addition of substrate. At least three independent readings are taken at each data point. All data fitting and statistical analyses are performed using SPSS v16.0 (IBM).

In this assay, compounds of the invention were tested and showed potent inhibition of the MIPs from *B. pseudomallei* and *C. burnetii*.

Cytotoxicity Reduction Assay

To test for virulence inhibition in one or more of the species containing MIPs by compounds of the invention, TABLE 1-continued Starting materials

| Feed code | Name | structure | Source |
|---|---|---|---|
| J | (1R*,2S*,4S*)-bicyclo[2.2.1]heptane-2-carboxylic acid | 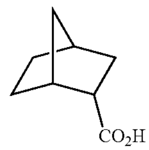 | Alfa Aesar (32482) |
| K | (1S*,2R*,5R*,6S*)-2-hydroxybicyclo[3.2.1]octane-6-carboxylic acid | 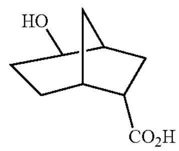 [SMILES: O=C(O)C1CC2CC1CCC2O] | Fisher (BTBG00035DA) |
| L | tetrahydro-2H-pyran-4-carboxylic acid | 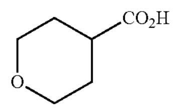 | Parkway Scientific (BX-103) |
| M | tetrahydro-2H-thiopyran-4-carboxylic acid | 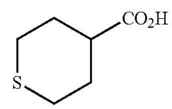 | Synthesis as per Strässler et al. 1997 |
| N | 3-hydroxybenzoic acid | 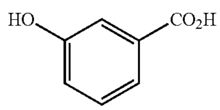 | Sigma (H20008) |
| O | 4-methylthiophene-2-carboxylic acid | 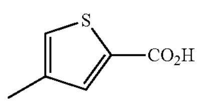 | Sigma (633550) |
| P | 3-amino-5-hydroxybenzoic acid | 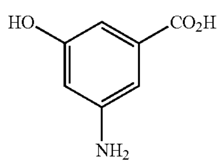 | Synthesised as per Becker and Rickards, 1984 |
| Q | 4-hydroxy-3,3-dimethylcyclohexanecarboxylic acid | 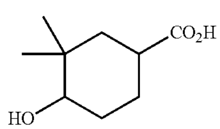 | Synthesised as described below |
| R | 4-methylenecyclohexanecarboxylic acid | 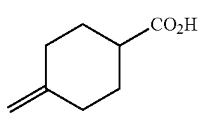 | Synthesised as described below |
| S | 4-methylcyclohex-3-enecarboxylic acid | 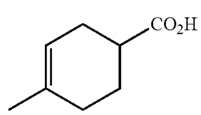 | Synthesised as described below |
| T | (1S*,4S*)-4-methylcyclohexanecarboxylic acid | 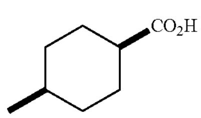 | Synthesised as described below |
| U | (1S*,3S*,4S*)-3,4-dihydroxycyclohexanecarboxylic acid | 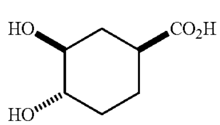 [SMILES: O=C(O)[C@H]1CC[C@H](O)[C@@H](O)C1] | Synthesised as described below |

TABLE 1-continued

| Starting materials | | | |
|---|---|---|---|
| Feed code | Name | structure | Source |
| V | 3-methylcyclohexanecarboxylic acid | | Sigma (330612) |
| W | isonicotinic acid | | Sigma (I17508) |
| X | 5-methylthiophene-2-carboxylic acid | | Sigma (M84429) |
| A1 | (1R*,4R*)-4-hydroxycyclohexanecarboxylic acid | | TCI (UK) Ltd (H1175) |
| B1 | (2S*)-bicyclo[2.2.1]heptane-2-carboxylic acid | | Synthesised as described below |
| C1 | (1S*,3S*)-3-hydroxycyclohexanecarboxylic acid | | Synthesised as described below |
| D1 | (1S*,3R*,4S*)-methyl 3-fluoro-4-hydroxycyclohexanecarboxylate | | Synthesised as described below |
| E1 | (1S*,3R*,4S*)-3-ethyl-4-hydroxycyclohexanecarboxylic acid | | Synthesised as described below |
| F1 | methyl 3,3-difluoro-4-hydroxycyclohexanecarboxylate | | Synthesised as described below |
| G1 | (1S*,3R*)-3-hydroxycyclohexanecarboxylic acid | | Synthesised as described below |

5-hydroxycyclohex-3-enecarboxylic acid—feed E

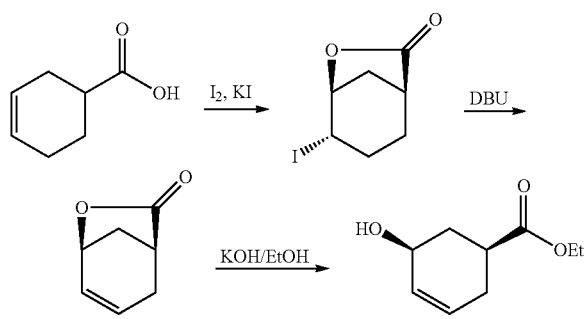

The title compound was prepared, in racemic form, by generating (1R*, 3R*, 4R*)-4-iodocyclohexane-1,3-carbolactone from cyclohex-3-ene carboxylic acid, which was then treated with the base DBU (1,8-diazabicyclo[5.4.0]undec-7-ene) to eliminate HI. The resultant (1R*, 5S*)-cyclohex-3-ene-1,5-carbolactone was then treated with potassium hydroxide dissolved in ethanol to yield the title compound (Marshall, J. A., and Shiping, X., 1995)

4-hydroxy-3,3-dimethylcyclohexanecarboxylic acid—feed Q

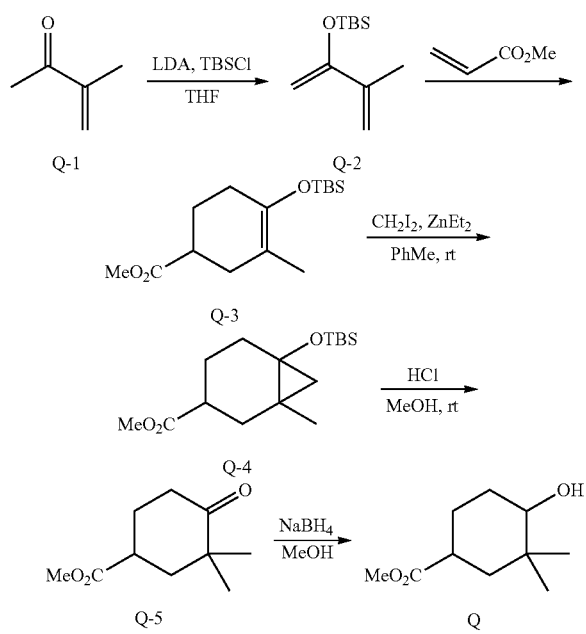

Synthesis of Q-2:

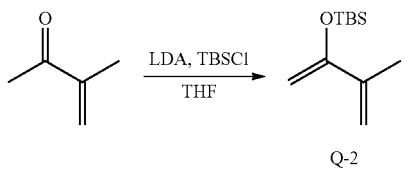

| Chemicals/Reagents & Solvents | moles | Eq. | Qty. |
| --- | --- | --- | --- |
| 3-Methyl-3-butene-2-one | 0.0595 | 1.0 | 5.00 g |
| n-Butyl Lithium | 0.0654 | 1.1 | 40.5 mL, 4.1 g |
| Diisopropyl amine | 0.0654 | 1.1 | 9.25 mL, 6.66 g |
| HMPA | 0.0119 | 0.2 | 2.13 mL |
| TBDMSCl | 0.0654 |  | 9.85 g |
| THF |  |  | (50 + 25) mL |

Brief procedure: n-BuLi was added to a solution of diisopropyl amine in tetrahydrofuran at −78° C. over a period of 15 minutes and stirred for 1 h at same temperature and at 0° C. for 30 minutes. The reaction mixture was cooled to −78° C., 3-methyl-3-butene-2-one in 25 mL of THF was added and stirring continued at −78° C. for 30 minutes. HMPA followed by TBDMSCl were added and stirring continued at same temperature for 2 h.

Work up: Reaction mixture was quenched with 100 mL of water and extracted with ethyl acetate, dried over $Na_2SO_4$, concentrated under reduced pressure to give crude product Purification: This compound was purified by distillation (87° C.-90° C.)

TLC system: 10% ethyl acetate in Hexane

Nature of the compound: Yellowish Brown solid, Yield: 3.99 g

Synthesis of Q-3:

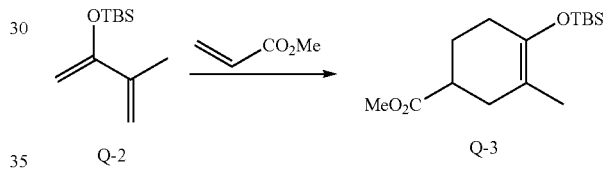

| Chemicals/Reagents & Solvents | moles | Eq. | Qty. |
| --- | --- | --- | --- |
| Q-2 | 0.040 | 1.0 | 8.0 g |
| Methyl acrylate | 0.032 | 0.8 | 2.752 g |
| Toluene |  |  | 240 mL |

Brief procedure: A mixture of Q-2 and methyl acrylate in toluene was heated (120° C.) with stirring in a sealed tube for 48-72 h.

Work up: Reaction mixture was extract with ethyl acetate, washed with 100 mL of water and dried over sodium sulfate. Solvent evaporation under reduced pressure afforded crude product.

Purification: The crude compound was purified by column chromatography using ethyl acetate in hexane to give pure product.

TLC system: 10% ethyl acetate in Hexane, $R_f$ Value: 0.8

Nature of the compound: Yellowish Brown solid, Yield: 3.19 g

Synthesis of Q-4:

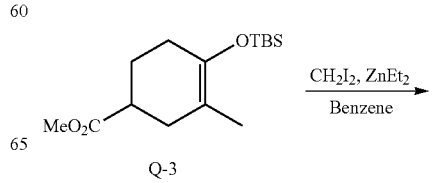

Synthesis of Q:

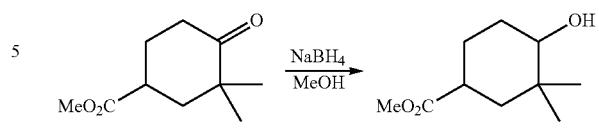

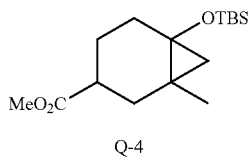

| Chemicals/Reagents & Solvents | Moles | Eq. | Qty. |
|---|---|---|---|
| Q-3 | 0.7 mmol | 1.0 | 0.2 g |
| ZnEt$_2$ | 10.5 mmol | 15 | 1.29 g |
| CH$_2$I$_2$ | 10.5 mmol | 15 | 2.81 g |
| dry Benzene | | | 20.0 mL |

Brief procedure: Q-3 was taken in dry benzene and to which were added diethyl zinc and diiodomethane simultaneously. The reaction mixture was stirred at 65° C. for 16 h under nitrogen atmosphere.

Work up: The reaction mixture was quenched with NH$_4$Cl (aqueous) and extracted into ethyl acetate. Solvent evaporated under reduced pressure afforded desired product as yellowish brown solid.

Purification: This crude was directly used for next step without further purification.

TLC system: 10% ethyl acetate in Hexane, R$_f$ value: 0.8

Nature of the compound: Yellowish Brown solid, Yield: 0.31 g (crude)

Synthesis of Q-5:

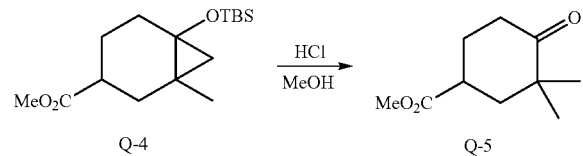

| Chemicals/Reagents & Solvents | moles | Eq. | Qty. |
|---|---|---|---|
| Q-4 | 0.0026 | 1.0 | 0.8 g |
| methanol | — | | 8 mL |
| HCl in ether | — | | 8 mL |

Brief procedure: HCl in ether (saturated) was added to a solution of Q-4 in dry methanol and the reaction mixture was stirred at room temperature for 30 min.

Work up: Reaction mixture was neutralised with NaHCO$_3$ (to pH 7) and extracted with ethyl acetate (three times). Combined organic layer was washed with brine and dried over Na$_2$SO$_4$. Solvent evaporated under reduced pressure afforded crude product.

Purification: The crude compound was purified by column chromatography over silica gel using ethyl acetate in hexane as solvent to yield pure desired product.

TLC system: 20% ethyl acetate in Hexane R$_f$ value: 0.5

Nature of the compound: Yellowish Brown solid Yield: 0.27 g

| Chemicals/Reagents & Solvents | mmol | Eq. | Qty. |
|---|---|---|---|
| Q-5 | 0.5 | 1.0 | 0.1 g |
| NaBH$_4$ | 0.5 | | 0.0189 g |
| Methanol | | | 1.0 mL |

Brief procedure: Q-5 was taken in methanol and was added sodium borohydride. The reaction mixture was stirred at −15° C. for 30 min.

Work up: Reaction mixture was quenched with 0.1 mL Acetic acid and extracted into ethyl acetate. Organic layer was washed with brine, dried over Na$_2$SO$_4$ and concentrated under reduced pressure to give crude product.

Purification: The compound was purified by column chromatography over silica gel using ethyl acetate in hexane as eluent to give desired product.

TLC system: 20% ethyl acetate in Hexane R$_f$ value: 0.3

Nature of the compound: Yellowish Brown solid Yield: 0.072 g 4-methylenecyclohexanecarboxylic acid—feed R

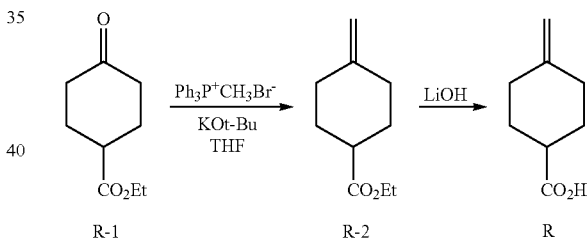

Synthesis of R-2:

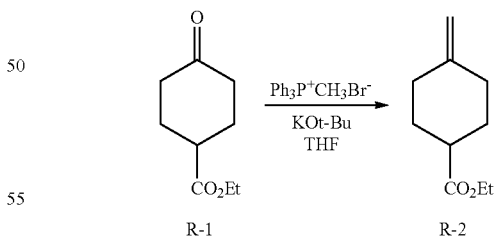

Brief

| Chemicals/Reagents & Solvents | Wt./Vol. | mmol | Eq. |
|---|---|---|---|
| ethyl 4-oxocyclohexane carboxylate | 5 g | 29.37 | 1 |
| methyltriphenylphosphonium bromide | 16.8 g | 47.02 | 1.6 |
| potassium tert-butoxide | 4.95 g | 44.08 | 1.5 |
| THF | 90 mL | — | — | procedure: KO-tBu was added to a solution of methyltriphenylphosponium bromide at 0° C. under nitrogen atmosphere and stirred for 30 min. To the above yellow colored reaction, a solution of ethyl 4-oxocyclohexane carboxylate in THF was added dropwise and the resulting mixture was stirred at the same temperature for 16 h.

Work up: The reaction mixture was quenched with water and extracted with diethyl ether. The combined ethereal extract was dried and concentrated under reduced pressure.

Purification: The crude residue was purified by silica gel (100-200 mesh) column chromatography by gradual elution from 5% to 10% EtOAc-petroleum ether.

TLC system: 20% Ethyl acetate-petroleum ether, $R_f$ value: 0.6

Nature of the compound: Colorless liquid, Yield: 3.5 g

Synthesis of R:

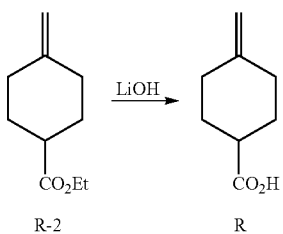

| Chemicals/Reagents & Solvents | Wt./Vol. | mmol | Eq. |
|---|---|---|---|
| R-2 | 6.7 g | 39.88 | 1 |
| LiOH•H$_2$O | 3.35 g | 79.76 | 2 |
| H$_2$O | 100 mL | — | — |
| THF | 100 mL | — | — |

Brief procedure: An aqueous solution of LiOH was added to R-2 in THF at room temperature and resulting mixture stirred at room temperature for 12 h.

Work up: The reaction mixture was diluted with pentane. The phases were separated and the aqueous layer was acidified with 4 N HCl at ice bath temperature and extracted with diethyl ether. The combined organic extract was dried and concentrated under reduced pressure to furnish the compound R as a solid.

Purification: No purification done.

TLC system: 30% Ethyl acetate-petroleum ether, $R_f$ value: 0.3

Nature of the compound: White solid, Yield: 3.9 g 4-methylcyclohex-3-enecarboxylic acid—feed S

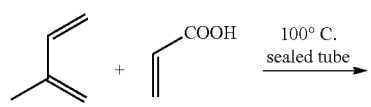

| Chemicals/Reagents & Solvents | Wt. | mmol. | Eq. |
|---|---|---|---|
| Isoprene | 6 g | 88.07 | 1.0 |
| Acrylic acid | 6.3 g | 88.07 | 1.0 |

Brief procedure: A mixture of isoprene and acrylic acid was taken in a 50 mL sealed tube and heated to 110° C. for 15 h.

Work up: The reaction mass was dissolved in ether and basified with saturated NaHCO$_3$ solution. The organic layer was discarded and the aqueous layer was washed with diethyl ether (3×50 mL) to remove polymeric material. The aqueous layer was then acidified with 20% HCl and extracted with DCM. The combined organic extract was dried over NaSO$_4$ and concentrated.

Purification: The product was repeatedly recrystallized from hexane at 0° C.

TLC system: 20% EtOAc in pet ether, $R_f$ value: 0.51

Nature of the compound: White solid, Yield: 1.1 g (1S*,4S*)-4-methylcyclohexanecarboxylic acid—feed T

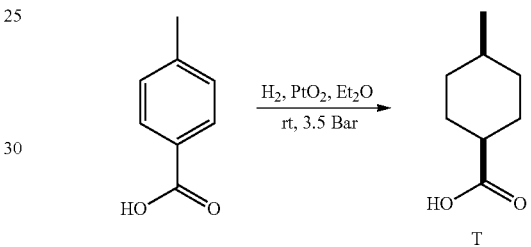

| Chemicals/Reagents & Solvents | Wt | mol | Eq. |
|---|---|---|---|
| p-Toluic acid | 10 g | 0.0734 | 1 |
| Platinum oxide | 3.31 g | 0.014 | 0.2 |
| Diethyl ether | 100 mL | — | — |

Brief procedure: A mixture of p-Toluic acid and PtO$_2$ in ether was placed in a 250 mL Parr hydrogenation apparatus overnight under 60 psi hydrogen pressure at room temperature.

Work-up: The reaction mixture was then filtered and concentrated under reduced pressure.

Purification: WG-433 was obtained as cis & trans isomers (84% & 15% respectively), the mixture was purified by column chromatography.

TLC system: 50% Diethyl ether/Hexane, $R_f$ value: 0.54

Nature of the compound: Light yellow color liquid, Yield: 5.0 g (1S*,3S*,4S*)-3,4-dihydroxycyclohexanecarboxylic acid—feed U

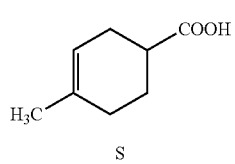

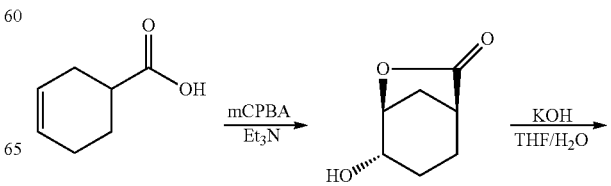

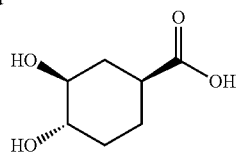

Racemic 3-cis,4-trans-dihydroxycyclohexane carboxylic acid was readily attainable from commercially available racemic 3-cyclohexene carboxylic acid. This acid was epoxidised through treatment with meta-chloroperbenzoic acid and converted to the lactone in situ by the addition of base (triethylamine), thus setting up the relative stereochemistries. This lactone was then hydrolysed by the action of aqueous potassium hydroxide, and the final product purified over ion exchange resin (see PAS Lowden Thesis 1997, Corey, E. J. and Huang, H., 1989).

(2S)-bicyclo[2.2.1]heptane-2-carboxylic acid—feed B1

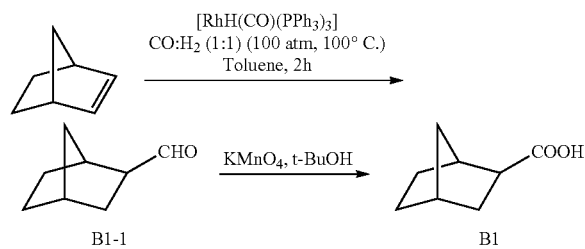

Synthesis of B1-1:

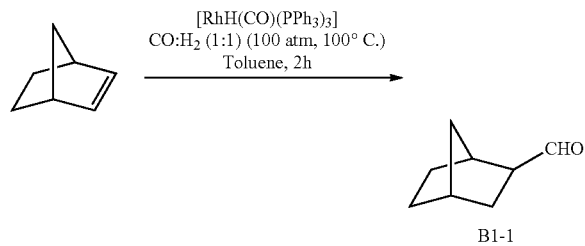

| Chemicals/Reagents & Solvents | Wt./Vol. | mmol | Eq. |
|---|---|---|---|
| Norbornene | 50.0 g | 531.06 | 1.0 |
| Carbonyltris(triphenyl phosphine)-rhodium(I) hydride | 0.49 g | 0.531 | 0.001 |
| Toluene | 625.0 mL | — | — |

Procedure: Norbornene was placed in a 2L stainless steel autoclave together with toluene and carbonyl tris (triphenyl phosphine)-rhodium (I) hydride. The reactor was pressurized to 1250 Psi with synthesis gas ($CO/H_2=1:1$) and heated to 100° C.

Work up: The reactor was cooled to room temperature; the residual gases removed by purging $N_2$ gas for 15-20 min and the solvent was concentrated under reduced pressure to give the crude B1-1.

Purification: B1-1 was purified by column chromatography using 60-120 mesh silica (eluent: 15% DCM-petroleum ether).

Nature of the compound: Pale yellow liquid Yield: 25 g (37.9%)

Synthesis of B1:

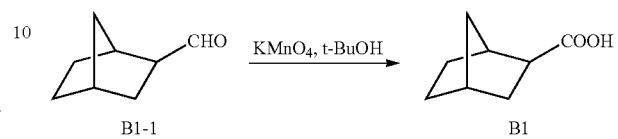

| Chemicals/Reagents & Solvents | Wt./Vol. | mmol | Eq. |
|---|---|---|---|
| B1-1 | 125.0 g | 1006.6 | 1.0 |
| Potassium permanganate | 154.0 g | 1006.6 | 1.0 |
| t-Butanol | 125.0 mL | — | — |
| Water | 125.0 mL | — | — |

Reaction time: 1 min Reaction temperature: rt

Brief procedure: To a solution of B1-1 in t-butanol was added water. To the resulting mixture an aq $KMnO_4$ solution was added with vigorous stirring at room temperature.

Work up: The reaction mixture was quenched by the addition of a saturated solution of sodium sulfite and the pH of the resulting mixture was adjusted to 3 with cold dilute HCl to dissolve the colloidal $MnO_2$. The reaction mixture was extracted with ethyl acetate, washed with water, dried over anhydrous $Na_2SO_4$ and concentrated under reduced pressure to yield crude B1.

Purification The crude B1 was purified by column chromatography using 100-200 mesh silica (eluent: 3% EtOAc-petroleum ether).

TLC system: 10% EtOAc-petroleum ether, $R_f$ value: 0.1

Nature of the compound: White crystalline solid, Yield: 100 g (1S*,3S*)-3-hydroxycyclohexanecarboxylic acid—feed C1

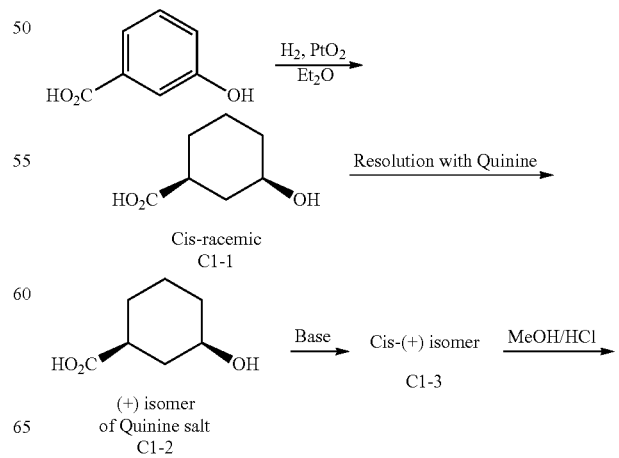

-continued

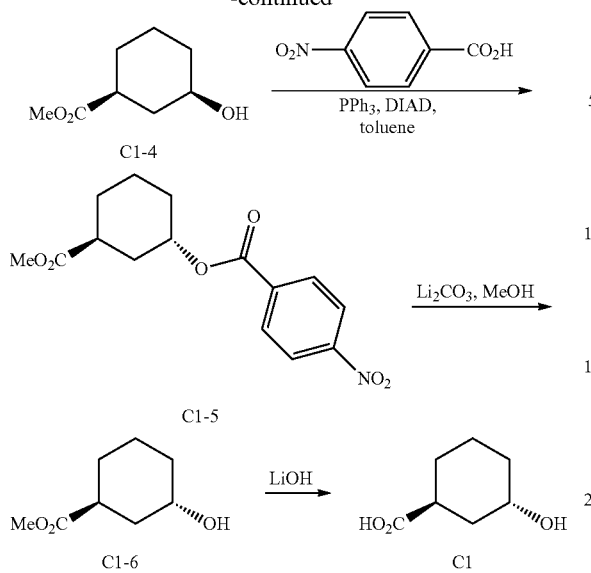

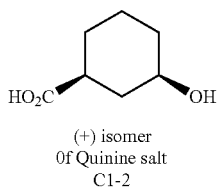

(+) isomer
Of Quinine salt
C1-2

| Chemicals/Reagents & Solvents | Wt./Vol. | mol | Eq. |
|---|---|---|---|
| C1-1 | 26 g | 0.18 | 1 |
| Quinine trihydrate | 35 g | 1.08 | 0.6 |
| Methanol | 500 mL | — | |

Brief procedure: Quinine trihydrate was dissolved in warm methanol, to this solution C1-1 in methanol was added portion wise. The combined solution was placed in a water bath at 50° C. and allowed to cool slowly to room temperature and then placed in ice bath for 3 h. The resulting mixture was filtered.

Purification: Recrystallisation from ethanol.

Nature of the compound: Off white solid, Yield: 40 g

Synthesis of C1-3:

Synthesis of C1-1:

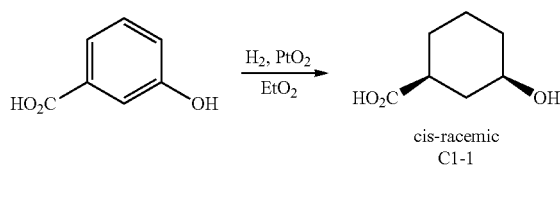 [SMILES: O=C(O)c1cccc(O)c1 ; O=C(O)[C@H]1CCC[C@@H](O)C1]

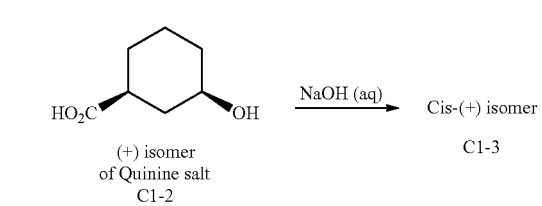

| Chemicals/Reagents & Solvents | Wt./Vol. | mol | Eq. |
|---|---|---|---|
| 3-Hydroxybenzoic acid | 100 g | 0.724 | 1 |
| Platinum oxide | 10 g | — | 10 |
| Diethyl ether | 500 mL | — | |

| Chemicals/Reagents & Solvents | Wt./Vol. | mol | Eq. |
|---|---|---|---|
| C1-2 | 40 g | 0.085 | 1 |
| NaOH | 3.4 g | 0.085 | 1 |
| water | 200 mL | — | |

Brief procedure: A solution of 3-hydroxybenzoic acid in diethyl ether was hydrogenated at 60 Psi with platinum oxide for 10 days.

Work up: After completion of the reaction, the catalyst was removed by filtration and washed with methanol under nitrogen; the organic layer was distilled under reduced pressure.

Purification: The residue was washed with petroleum ether (3×100 mL), the mixture on recrystallization four times with ethyl acetate gave pure compound.

TLC system: 10% MeOH/DCM, $R_f$ value: 0.12

Nature of the compound: Off white solid, Yield: 26 g

Synthesis of C1-2:

Brief procedure: Quinine salt was suspended in a stirred solution of NaOH in water. The mixture was stirred at 80° C. for 2 h.

Work up: Water was added and washed with chloroform. The aq layer was acidified with $H_2SO_4$ and extracted with ethyl acetate. Combined ethyl acetate layer was dried and concentrated.

Purification: Recrystallization from ethyl acetate.

TLC system: 10% MeOH/DCM $R_f$ value: 0.12

Nature of the compound: Off white solid. Yield: 9.1 g

Synthesis of C1-4:

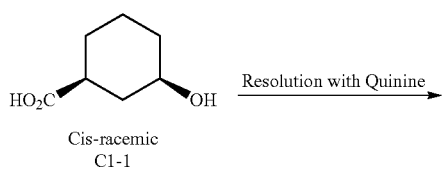

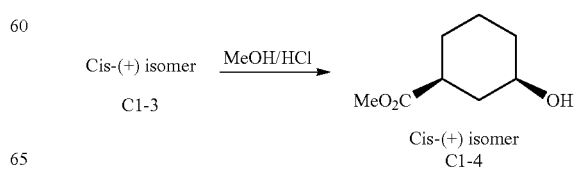

| Chemicals/Reagents & Solvents | Wt./Vol. | mol | Eq. |
|---|---|---|---|
| C1-3 | 1.2 g | 0.0083 | 1 |
| Methanolic HCl | 30 mL | — | — |

Brief procedure: A solution of C1-3 in methanolic HCl was heated under refluxed overnight.

Work up: After completion of the reaction, organic layer was removed under reduced pressure.

Purification: The residue was extracted with ethyl acetate, washed with water, brine, dried over $Na_2SO_4$ and concentrated to yield light yellow oil.

TLC system: 10% MeOH/DCM, $R_f$ value: 0.4

Nature of the compound: Light yellow oil, Yield: 1.2 g

Synthesis of C1-5:

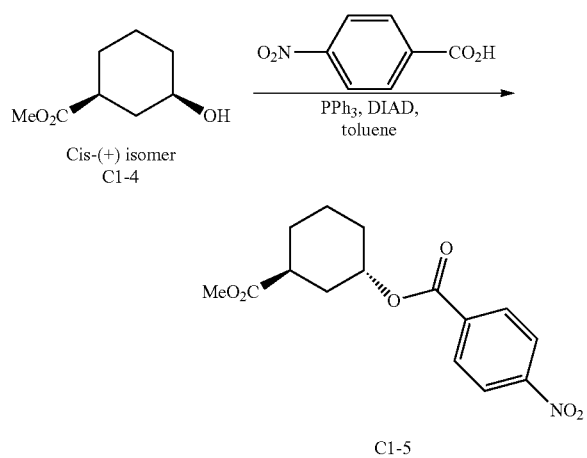

| Chemicals/Reagents & Solvents | Wt./Vol. | mol | Eq. |
|---|---|---|---|
| C1-4 | 1.2 g | 0.0076 | 1 |
| 4-Nitrobenzoic acid | 1.39 g | 0.0083 | 1.1 |
| DIAD | 3.07 g | 0.0152 | 2 |
| TPP | 3.98 g | 0.0152 | 2 |
| Toluene | 12 mL | — | — |

Reaction time: 2 days Temperature conditions: r.t

Brief procedure: A solution of C1-4, 4-nitrobenzoic acid, TPP in Toluene was cooled to −78° C. then DIAD was added at 50° C. and stirred at r.t for 2 days.

Work up: After completion of the reaction, the reaction mixture was concentrated.

Purification: The residue on purification by column chromatography using hexane/ethyl acetate (10% to 40% ethyl acetate gradient) gave off white solid.

TLC system: 30% ethyl acetate/petroleum ether, $R_f$ value: 0.7

Nature of the compound: Off white solid, Yield: 700 mg

Synthesis of C1-6:

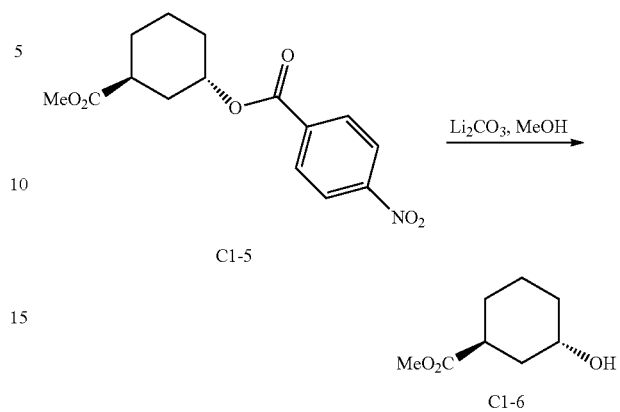

| Chemicals/Reagents & Solvents | Wt./Vol. | mol | Eq. |
|---|---|---|---|
| C1-5 | 1 g | 0.0032 | 1 |
| $Li_2CO_3$ | 0.84 g | 0.0128 | 4 |
| MeOH | 10 mL | — | — |

Reaction time: Overnight Temperature conditions: r.t

Brief procedure: A solution of C1-5 and $Li_2CO_3$ in MeOH was stirred overnight at r.t.

Work up: After completion of the reaction, organic layer was distilled under reduced pressure, extracted with ethyl acetate, washed with water, brine, dried over $Na_2SO_4$. and concentrated to yield light yellow oil.

Purification: The residue was washed with petroleum ether (3×100 mL), recrystallized four times with ethyl acetate to obtain pure compound.

TLC system: 30% ethyl acetate/petroleum ether, $R_f$ value: 0.3 Nature of the compound: Light yellow oil, Yield: 330 mg Synthesis of C1:

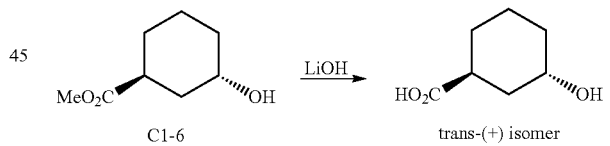

| Chemicals/Reagents & Solvents | Wt./Vol. | mol | Eq. |
|---|---|---|---|
| Compd 6 | 350 g | 0.0022 | 1 |
| LiOH | 0.16 g | 0.0066 | 3 |
| THF:Water (4:1) | 20 mL | — | — |

Brief procedure: A solution of C1-6 and LiOH in THF: Water (4:1) was stirred for overnight.

Work up: After completion of the reaction, the organic layer was distilled under reduced pressure, extracted with ethyl acetate, washed with water, brine, dried over $Na_2SO_4$ and concentrated to afford light yellow oil.

Purification: Crude on Recrystallisation with ethyl acetate afforded pure compound.

TLC system: 10% MeOH/DCM, $R_f$ value: 0.25

Nature of the compound: Off white solid, Yield: 300 mg

(1S*,3R*,4S*)-methyl 3-fluoro-4-hydroxycyclohexanecarboxylate—feed D1

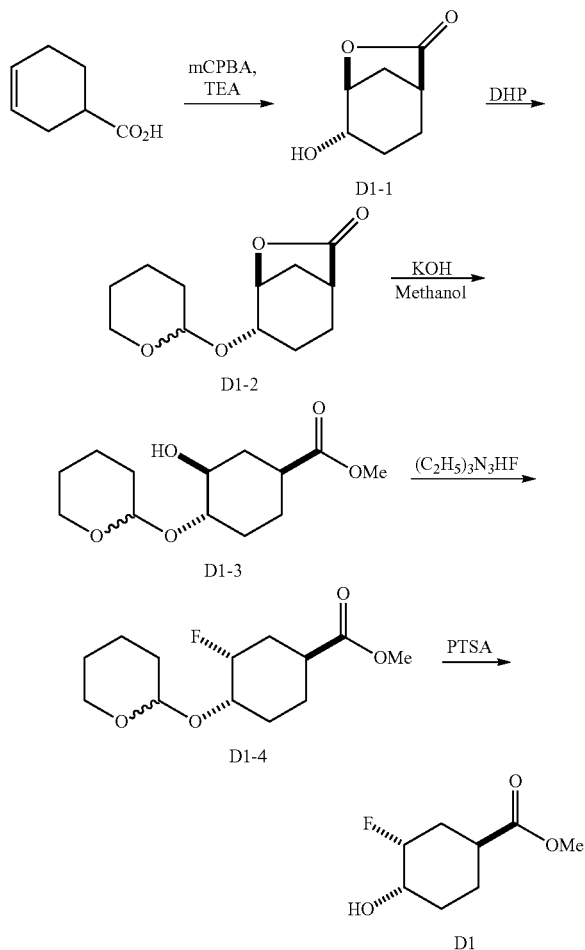

Synthesis of D1-1:

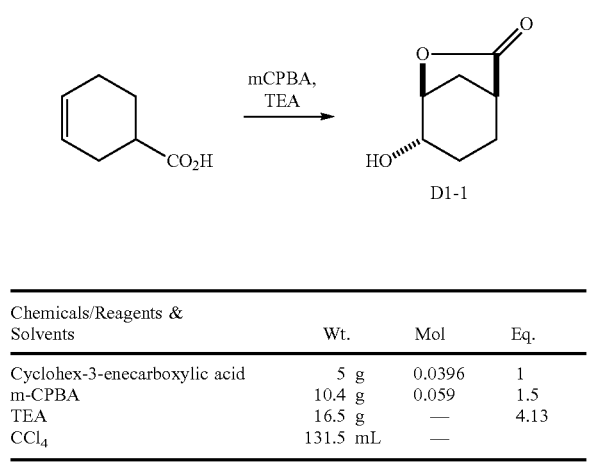

| Chemicals/Reagents & Solvents | Wt. | Mol | Eq. |
|---|---|---|---|
| Cyclohex-3-enecarboxylic acid | 5 g | 0.0396 | 1 |
| m-CPBA | 10.4 g | 0.059 | 1.5 |
| TEA | 16.5 g | — | 4.13 |
| CCl$_4$ | 131.5 mL | — | |

Reaction time: 8 h, Reaction temperature: 65° C.

Procedure: m-CPBA was added to a solution of cyclohex-3-enecarboxylic acid in CCl$_4$ and the reaction mixture was stirred for 4 h. Triethyl amine was added and the resulting reaction mixture was stirred at 65° C. for 4 h.

Work up: The reaction mixture was concentrated under reduced pressure to get crude residue.

Purification: The crude product was purified by flash column chromatography using ethyl acetate and petroleum ether as eluents.

TLC system: 50% Ethyl acetate in pet ether, R$_f$ value: 0.3

Nature of the compound: Light brown color solid, Yield: 50%

Synthesis of D1-2:

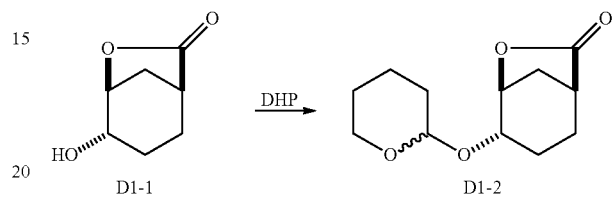

| Chemicals/Reagents & Solvents | Wt. | Mol | Eq. |
|---|---|---|---|
| D1-1 | 3.5 g | 0.024 | 1 |
| DHP | 5.57 g | 0.066 | 2.69 |
| Pyridinium p-toluene sulfonate | 0.123 g | 0.0004 | 0.02 |
| DCM | 42 mL | — | |

Reaction time: 2 h Reaction temperature: RT

Procedure: To a solution of D1-1 in DCM, was added dihydropyran followed by pyridinium p-toluene sulfonate. The resulting reaction mixture was stirred for 2 h at room temperature.

Work up: The reaction mixture was cooled to 0° C., quenched with aqueous 5% NaHCO$_3$ solution. Organic layer separated, aqueous layer re-extracted with dichloromethane and combined organic layer was washed with brine. Finally, organic layer was dried over sodium sulfate and concentrated under reduced pressure to give crude product.

Purification: The compound was directly taken for next step without further purification.

TLC system: 50% Ethyl acetate in pet ether, R$_f$ value: 0.8

Nature of the compound: Brown color liquid, Yield: 77%

Synthesis of D1-3:

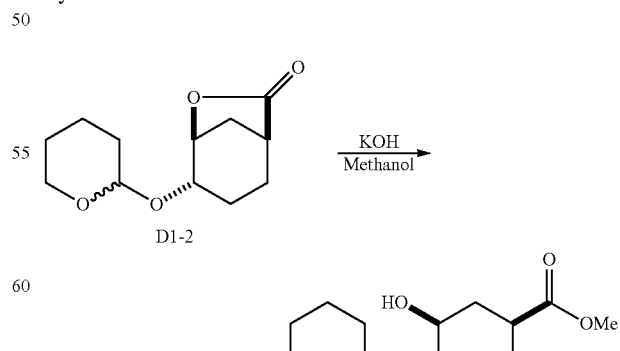

| Chemicals/Reagents & Solvents | Wt. | Mol | Eq. |
|---|---|---|---|
| D1-2 | 6.3 g | 0.176 | 1 |
| KOH in methanol | 0.012 g + 0.315 mL | 0.0002 | 0.0012 |
| Methanol | 12.6 mL | — | |

Reaction time: 1 h Reaction temperature: RT

Procedure: KOH in methanol was added to a solution of D1-2 in methanol and the resulting reaction mixture stirred at room temperature over a period of 1 h.

Work up: The reaction mixture was diluted with chloroform and water, organic layer separated and aqueous layer was re-extracted with chloroform. The combined organic layer was washed with saturated NH$_4$Cl solution and brine, dried over sodium sulfate and solvent evaporated under reduced pressure.

Purification: The crude product was directly used in next step without further purification.

TLC system: 50% Ethyl acetate in pet ether, R$_f$ value: 0.4

Nature of the compound: Yellow color liquid, Yield: 70%

Synthesis of D1-4

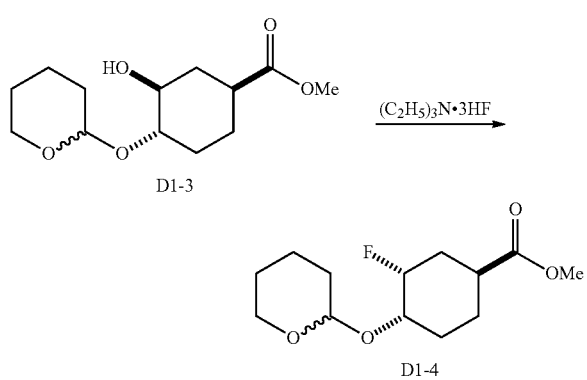

D1-3

D1-4

| Chemicals/Reagents & Solvents | Wt. | Mol | Eq. |
|---|---|---|---|
| D1-3 | 1 g | 0.0038 | 1 |
| Perfluorobutane sulfonylfluoride | 2.341 g | 0.0077 | 2 |
| Triethylamine tri hydrofluoride | 1.24 g | 0.0077 | 2 |
| TEA | 3.28 mL | 0.023 | 6 |
| THF | 6.2 mL | — | |

Reaction time: 12 h, Reaction temperature: RT

Procedure: D1-3 was dissolved in THF and were added perfluorobutanesulfonylfluoride, triethyl amine and triethylamine-trihydrofluoride. The resulting reaction mixture was stirred overnight under nitrogen atmosphere.

Work up: The reaction mixture was filtered, solid washed with ethyl acetate-hexane (1:3) and solvent evaporated under reduced pressure.

Purification: The crude product was purified by flash column chromatography using ethyl acetate and petroleum ether as eluents.

TLC system: 50% Ethyl acetate in petroleum ether, R$_f$ value: 0.8 Nature of the compound: Brown color liquid, Yield: 69%.

Synthesis of D1

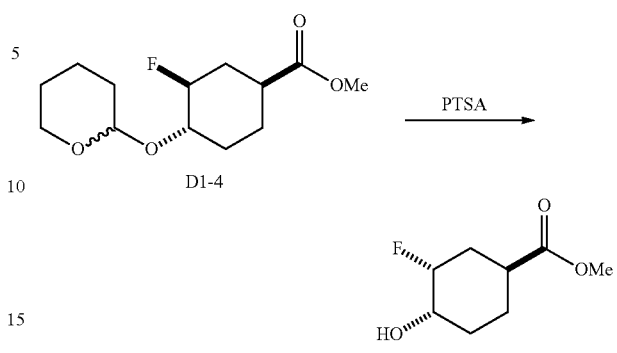

D1-4

D1

| Chemicals/Reagents & Solvents | Wt. | Mol | Eq. |
|---|---|---|---|
| D1-4 | 0.050 g | 0.192 mmol | 1 |
| Polymerbound PTSA | 0.002 g + 0.001 g | 2 mmol/1 g | — |
| Methanol | 0.1 mL | — | |

Reaction time: 3 h, Reaction temperature: 50° C.

Procedure: Polymerbound PTSA was added to a solution of D1-4 in methanol and the resulting suspension was stirred at 50° C. over a period of 2 h. Another portion of polymerbound PTSA was added and stirring continued for another 1 h at same temperature.

Work up: The reaction mixture was filtered through a sintered funnel and solvent removed under reduced pressure.

Purification: The crude product was purified by flash column chromatography using ethyl acetate and petroleum ether as eluents.

TLC system: 50% Ethyl acetate in pet ether, R$_f$ value: 0.3

Nature of the compound: Yellow color liquid, Yield: 60%

(1S*,3R*,4S*)-3-ethyl-4-hydroxycyclohexanecarboxylic acid—feed E1

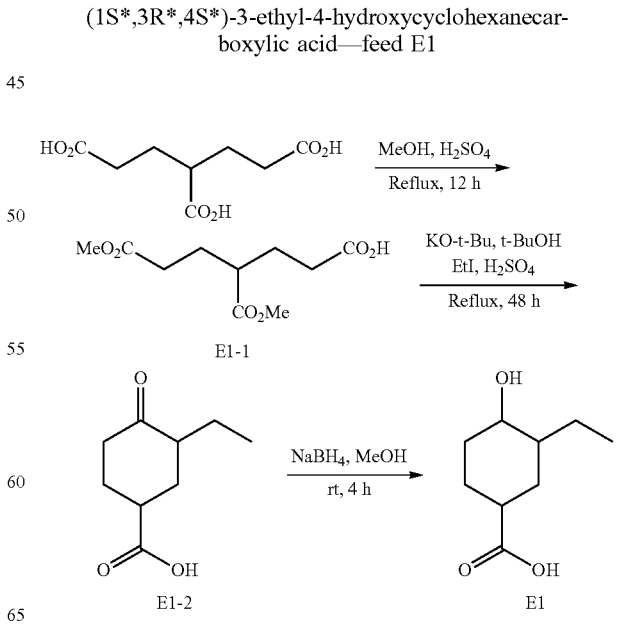

Synthesis of E1-1

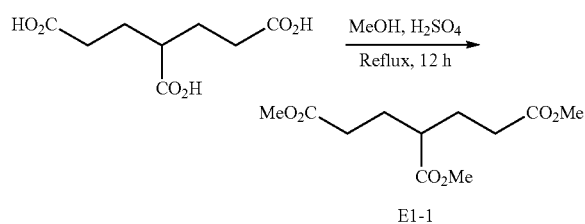

| Chemicals/Reagents & Solvents | Wt. | mol | Eq. |
|---|---|---|---|
| pentane-1,3,5-tricarboxylic acid | 100 g | 490 | 1.0 |
| $H_2SO_4$ | 20 mL | 245 | 0.5 |
| Methanol | 1500 mL | — | 15 V |

Reaction time: 12 h, Reaction temperature: reflux

Brief procedure: A mixture of pentane-1,3,5-tricarboxylic acid in dry methanol and sulfuric acid was heated under refluxed for 12 h.

Work up: The reaction mixture was concentrated in vacuo, diluted with ethyl acetate and washed repeatedly with water followed by 10% $NaHCO_3$. The combined organic extract was dried, filtered and concentrated under reduced pressure to give a residue.

Purification: The crude residue was purified by silica gel (60-100 mesh) column chromatography using 15% ethyl acetate-petroleum ether as eluent.

TLC system: 30% Ethyl acetate-petroleum ether, $R_f$ value: 0.8 Nature of the compound: Colorless sticky liquid, Yield: 110 g (95%)

Synthesis of E1-2:

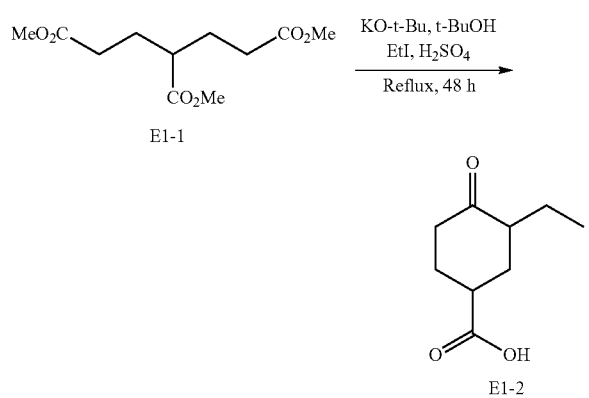

| Chemicals/Reagents & Solvents | Wt. | mol | Eq. |
|---|---|---|---|
| E1-1 | 110.0 g | 447.1 | 1.0 |
| Potassium t-butoxide | 150.28 g | 1341 | 3.0 |
| ethyl iodide | 288 mL | 3577 | 8.0 |
| t-Butyl alcohol | 770 mL | — | — |
| 10% sulfuric acid | 288 mL | — | — |

Brief procedure: To a solution of potassium t-butoxide in dry t-butyl alcohol, under argon atmosphere was added in one portion a solution of E1-1 to afford a viscous orange solution. The reaction mixture was heated at reflux for 3 h, then cooled to RT and ethyl iodide was added with stirring. The reaction mixture was stirred at reflux for 10 h, and then t-butyl alcohol was removed in vacuo. To the residue was mixed with 10% sulfuric acid and the mixture was refluxed for further 48 h.

Work up: The reaction mixture extracted with three portions of diethyl ether, the combined extract was washed successively with water and saturated ammonium sulfate, dried over $Na_2SO_4$, filtered and concentrated in vacuo to give the crude product.

Purification: The crude residue was purified by silica gel (100-200 mesh) column chromatography using 30% ethyl acetate-petroleum ether as eluent.

TLC system: 30% Ethyl acetate-petroleum ether, $R_f$ value: 0.14

Nature of the compound: Colorless sticky liquid, Yield: 50 g

Synthesis of E1:

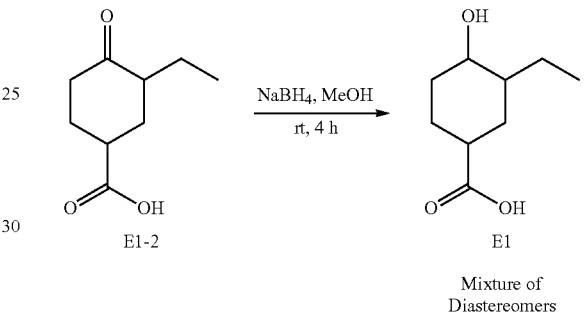

| Chemicals/Reagents & Solvents | Wt. | M. Mol | Eq. |
|---|---|---|---|
| E1-2 | 30 g | 176.47 | 1.0 |
| $NaBH_4$ | 10.1 g | 264.7 | 1.5 |
| Methanol | 300 mL | — | |

Brief procedure: $NaBH_4$ was added portion-wise to a stirred solution of E1-2 in methanol at 0° C. and further stirred at room temperature for 4 h.

Work up: The reaction mixture was concentrated in vacuo to give the crude product.

Purification: The crude residue was purified by silica gel (100-200 mesh) column chromatography using 28% ethyl acetate-petroleum ether as eluent.

TLC system: 90% Ethyl acetate-petroleum ether, $R_f$ value: 0.6

Nature of the compound: Light yellow viscous liquid, Yield: 15 g methyl 3,3-difluoro-4-hydroxycyclohexanecarboxylate—feed F1

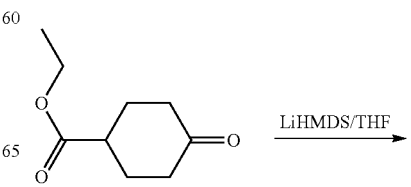

-continued

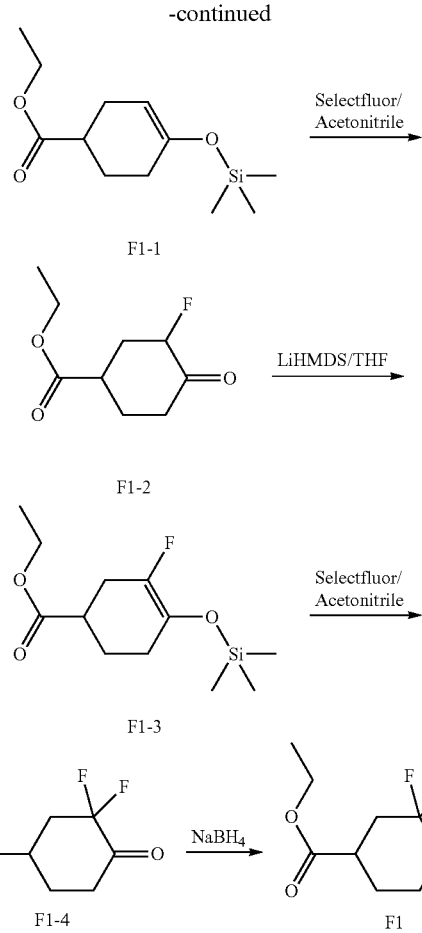

Synthesis of F1-1

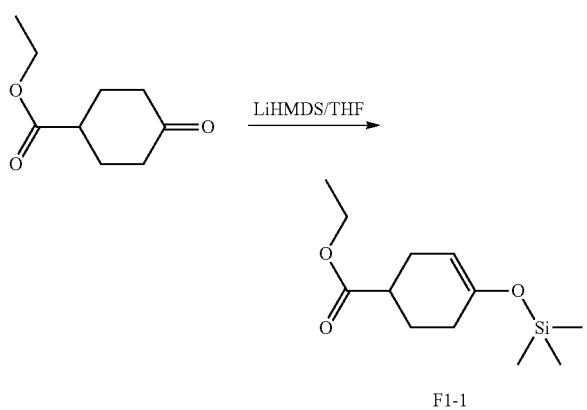

| Chemicals/Reagents & Solvents | Wt. | Mol | Eq. |
|---|---|---|---|
| Ethyl-4-oxocyclohexane carboxylate | 25 g | 0.146 | 1 |
| LiHMDS | 29.73 g | 0.177 | 1.21 |
| TMS-Cl | 24.1 g | 0.22 | 1.51 |
| THF | 567 + 567 mL | — | — |

Ethyl-4-oxocyclohexane carboxylate in THF was added dropwise at −78° C. to a stirred solution of lithium hexamethyldisilazide in THF. The reaction mixture was stirred for 1 h at same temperature and TMS-Cl was added. It was stirred for 10 minutes at same temperature and then for 1 hour at room temperature. The reaction was monitored by TLC. The reaction mixture was concentrated under reduced pressure, added hexane and filtered off. Filtrate was concentrated under reduced pressure to get crude product. The crude product was purified by column chromatography over silica gel using diethyl ether in hexane.

TLC system: 30% Ethyl acetate in petroleum ether, Rf value: 0.8

Nature of the compound: Yellow liquid, Yield: 19.5 g

Synthesis of F1-2

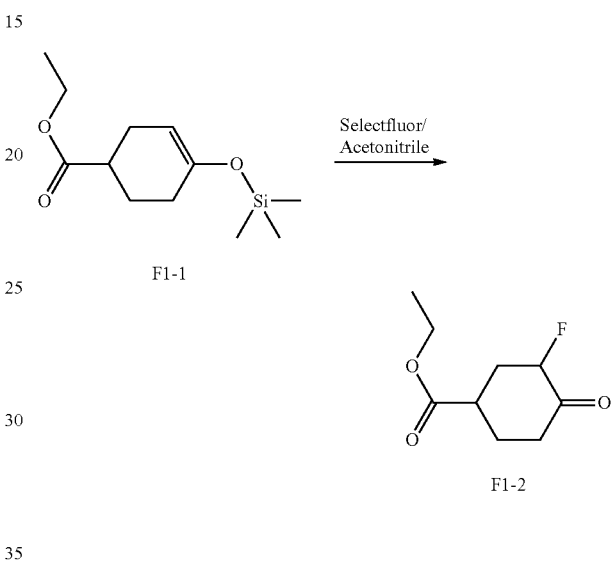

| Chemicals/Reagents & Solvents | Wt. | Mol | Eq. |
|---|---|---|---|
| F1-1 | 19 g | 0.0785 | 1 |
| Selectfluor | 40.4 g | 0.0942 | 1.19 |
| Acetonitrile | 337.5 mL | — | — |

Selectfluor was added to a solution of F1-1 in acetonitrile at 0° C. under nitrogen atmosphere and stirred for 1.5 hours. The reaction mixture was partitioned between water and ethyl acetate. Organic layer separated, washed with NaHCO₃ followed by brine and dried over sodium sulfate. Solvent was removed under reduced pressure to get crude product. The crude product was purified by column chromatography over silica gel using diethyl ether in hexane.

TLC system: 30% Ethyl acetate in petroleum ether, Rf value: 0.3

Nature of the compound: Light Yellow Liquid, Yield: 6.7 g

Synthesis of F1-3

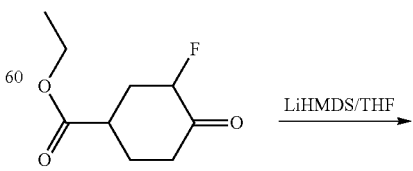

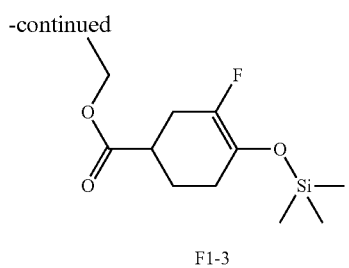

F1-3

| Chemicals/Reagents & Solvents | Wt. | Mol | Eq. |
| --- | --- | --- | --- |
| F1-2 | 6.02 g | 0.0320 | 1 |
| LiHMDS | 6.48 g | 0.038 | 1.21 |
| TMS-Cl | 5.25 g | 0.483 | 1.51 |
| THF | 136.6 + 136.6 mL | — | — |

F1-2 in THF was added dropwise at −78° C. to a stirred solution of lithium hexamethyldisilazide in THF. The reaction mixture was stirred for 1 hour at same temperature and TMS-Cl was added. It was stirred for 10 min at same temperature and 1 h at room temperature.

Work up: The reaction mixture was concentrated under reduced pressure, added hexane and filtered off. Filtrated was concentrated under reduced pressure to get crude desired product.

Purification: The crude product was purified by column chromatography over silica gel using diethyl ether in hexane.

TLC system: 30% Ethyl acetate in petroleum ether, Rf value: 0.8

Nature of the compound: Yellow liquid, Yield: 2.8 g

Synthesis of F1-4

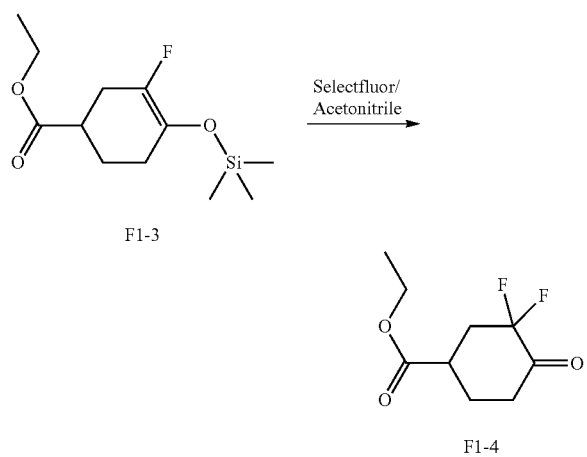

F1-3

Selectfluor/Acetonitrile

F1-4

| Chemicals/Reagents & Solvents | Wt. | Mol | Eq. |
| --- | --- | --- | --- |
| F1-3 | 2.5 g | 0.00962 | 1 |
| Selectfluor | 4.05 g | 11.442 | 1.19 |
| Acetonitrile | 30 mL | — | — |

Selectfluor was added to a solution of F1-3 in acetonitrile at 0° C. under nitrogen atmosphere and stirred for 1.5 h.

Work up: The reaction mixture was partitioned between water and ethyl acetate. Organic layer separated, washed with NaHCO$_3$ followed by brine and dried over sodium sulfate. Solvent was removed under reduced pressure to get crude desired product.

Purification: The crude product was purified by column chromatography over silica gel using diethyl ether in hexane.

TLC system: 30% Ethyl acetate in petroleum ether, Rf value: 0.3

Nature of the compound: Light Yellow Liquid, Yield: 0.0.5 g

Synthesis of F1

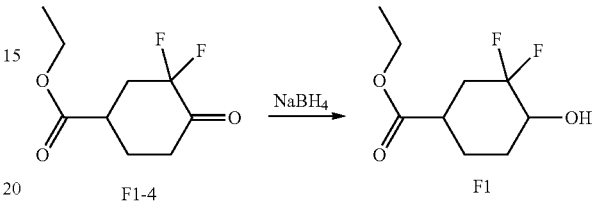

F1-4    NaBH$_4$    F1

| Chemicals/Reagents & Solvents | Wt. | Mol | Eq. |
| --- | --- | --- | --- |
| F1-4 | 0.45 g | 0.00218 | 1.0 |
| Sodium Borohydride | 0.0908 g | 0.0024 | 1.1 |
| Ethanol | 4.5 mL | — | — |

F1-4 was dissolved in EtOH and sodium borohydride was added at 0° C. The mixture was stirred for 30 min at same temperature.

Work up: The reaction was quenched with water, extracted with dichloromethane, dried over sodium sulfate and solvent evaporated under reduced pressure to get crude product.

Purification: The crude product was purified by column chromatography over silica gel using diethyl ether in petroleum ether as eluent TLC system: 30% Ethyl acetate in petroleum ether, Rf value: 0.5

Nature of the compound: Light Yellow Liquid, Yield: 0.170 g (1S*,3R*)-3-hydroxycyclohexanecarboxylic acid—feed G1

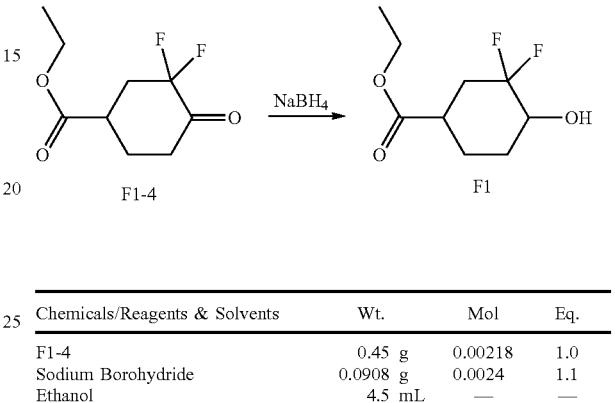

G1

| Chemicals/Reagents & Solvents | Wt./Vol. | Mol | Eq. |
| --- | --- | --- | --- |
| 3-Hydroxybenzoic acid | 10 g | 0.072 | 1 |
| Platinum oxide | 1 g | 0.004 | 0.6 |
| Diethyl ether | 250 mL | — | 25 V |

Brief procedure: A solution of 3-hydroxybenzoic acid in diethyl ether was hydrogenated with platinum oxide at 60 psi for 10 days.

Work up: After completion of the reaction, the catalyst was removed by filtration and washed with methanol under nitrogen; the organic layer was distilled under reduced pressure.

Purification: The residue was washed with petroleum ether (3×100 mL), the mixture was recrystallized four times with ethyl acetate to afford pure compound.

TLC system: 10% MeOH/DCM, $R_f$ value: 0.25

Nature of the compound: Off white solid, Yield: 2.6 g (25%)

Methods

Analytical Biotransformations

Production of rapamycin analogues and contracted rapamycins was carried out by fermentation of *Streptomyces rapamycinicus*. Typically strains were grown on ISP3 agar at 28° C. for 10-14 days to achieve good sporulation and used to inoculate 7 ml seed medium RapV7 (50 mL polypropylene centrifuge tubes (falcon tubes) (cat no.227261, purchased from Greiner Bio-One Ltd, Stonehouse, Gloucestershire, UK)) closed with foam plugs by transferring an agar plug (5 mm diameter). Alternatively 35 µL of a thawed spore stock was used for the inoculation. The inoculated seed medium was incubated with shaking at 300 rpm, 2.5 cm throw at 28° C. for 48 hours. For production the fermentation medium MD6 (7 mL in falcon tube as before) was inoculated with 0.5 mL of the seed culture using a wide bore tip and incubated with shaking at 300 rpm, 2.5 cm throw at 26° C. for six days. The culture was then harvested for extraction. A selected starter unit feed (corresponding to the desired starting unit for biosynthesis of the target compound) was fed to the production medium 24 hours post inoculation. Typically feed was dissolved in methanol (0.05 mL) and added to culture to give final concentration of 2 mM. The broth was extracted by aliquoting 0.9 ml into an eppendorf tube (2 ml) and adding methanol (0.9 ml). The eppendorf was then shaken on a vibrax bed for 30 minutes before the cell debris was removed by centrifugation (13, 200 rpm, 10 minutes). An aliquot of the supernatant was then transferred to an LC-vial for analysis by the methods described below.

Preparative Biotransformations

Spore stocks of the strains for fermentation were prepared after growth on ISP3 agar medium and preserved in 20% w/v glycerol in distilled water and stored at −80° C. Spore stocks were recovered onto plates of MAM or ISP3 medium and incubated for 10-11 days at 28° C.

Vegetative cultures (seed cultures) were prepared using working spore stocks of at 0.05% inoculum and inoculating into 400 ml medium RapV7 in 2 liter Erlenmeyer flasks with foam plugs. Cultivation was carried out for 48 hours at 28° C., 250 rpm (2.5 cm throw). The entire seed culture in one flask was transferred into 15 liters of medium MD6/5-1 pre-adjusted at pH 6.0-7.0 in a V7 Braun 22 L fermenter. The fermentation was carried out for 6 days at 26° C., with starting agitation at 200 rpm, aeration rate at 0.5 VN/M and dissolved oxygen (DO) level controlled with the agitation cascade at 30% air saturation. The starting agitation was set at 200 rpm. For production of compound, the selected precursor to feed (starting unit for biosynthesis of target compound) was fed to the production medium 24 hours post inoculation. Feed was dissolved in 3 mL to 5 mL methanol and added to the culture to give final concentration of 2 mM of the feed compound. The amount of methanol does not exceed 1% of the total volume. Fermentation was continued for further five days post-feeding, before harvesting.

Harvested whole broth was centrifuged at 3500 rpm (RCF 3300 g) for 25 mins. The clarified broth was assayed and discarded if less than 5% target compound detected. The cell pellet was removed from the centrifuge pots with acetonitrile and decanted into a 10 L glass duran. Further acetonitrile is added to give a ratio of 2 volumes of solvent to 1 volume of cells. The mixture was then stirred for 1 hour using an overhead electric paddle stirrer at 600 rpm.

After 1 hour the stirring was stopped and the mixture left to settle under gravity for 15 mins. The solvent layer was removed as extract_1 and a further 2 volumes of acetonitrile added to the remaining cells. This was stirred again as above to obtain extract_2. Any remaining rapatractins in the cell pellet can be removed by a third extraction if required.

Any target compound in the clarified broth can be recovered by adding an equal volume of ethyl acetate and stirring for 1 hour in a glass duran using an overhead electric paddle stirrer at 600 rpm. The organic solvent was then separated by centrifugation at 3500 rpm (RCF 3300 g) for 15 mins.

The combined extracts from both the cell pellet and, if required clarified broth, were concentrated in vacuo to a residual aqueous extract which was then extracted into an equal volume of ethyl acetate. A second ethyl acetate extraction can be performed as necessary.

The ethyl acetate extract containing the target rapatractin is then concentrated in vacuo to yield a final often oily crude.

The crude extract was dissolved in methanol, and silica gel added (approximately equal amount to the extract by weight) and the solvent removed in vacuo to a free-flowing powder. The impregnated silica is loaded on to a silica gel column (20×5 cm) and eluted with 100% $CHCl_3$, and gradually increases polarity by adding MeOH (to a maximum 5% MeOH). Approximately 20×250 ml fractions were collected and monitored by TLC and analytical HPLC. The fractions containing the rapatractins were loaded onto a second silica gel column (15×2 cm) and eluted with a mixture of hexane and ethyl acetate (1:1). First 1 L of (1:1) mixture was passed through, then 1 L of (40:60), and continued to 100% of EtOAc. Approximately 20×250 mL fractions were collected and individually checked by tlc and analytical HPLC. Fractions found to contain rapatractins were combined and the solvents were removed in vacuo. This bulk was then dissolved in acetonitrile and multiple injections (about 100 mg crude per injection) made to preparative HPLC using a water acetonitrile gradient mixture for 30 minutes (actual methods depend on compound polarity). The solvent from the resulting pure rapatractin containing fractions was removed in vacuo and the compound analysed by LC-MS and NMR for characterisation.

NMR Structure Elucidation Methods

NMR spectra were recorded on a Bruker Advance 500 spectrometer at 298 K operating at 500 MHz and 125 MHz for $^1H$ and $^{13}C$ respectively. Standard Bruker pulse sequences were used to acquire $^1H$-$^1H$ COSY, APT, HMBC and HMQC spectra. NMR spectra were referenced to the residual proton or standard carbon resonances of the solvents in which they were run.

Assessment of Compound Purity

Purified compounds were analysed using LCMS method 2 described. LCMS method 2: chromatography was achieved over a Phenomenex HyperClone $C_{18}$-BDS column (4.6×150 mm, 3 micron particle size) eluting with a gradient of water+0.1% formic acid:acetonitrile+0.1% formic acid, (90:10) to (0:100), at 1 mL/min over 20 min. Purity was assessed by MS and at multiple wavelengths (210, 254 & 276 nm). All compounds were >95% pure at all wavelengths. Purity was finally confirmed by inspection of the $^1H$ and $^{13}C$ NMR spectra.

HPLC Analysis of Rapamycin Analogues and Contracted or Expanded Rapamycins in Fermentation Broths An aliquot of whole culture broth (0.9 mL) was added to methanol (0.9 mL) in a 2 mL eppendorf, and then shaken for 30 minutes. The sample was centrifuged (10 minutes, 13000 rpm) and the supernatant (0.15 ml) was transferred to a HPLC vial for analysis by HPLC with diode array detection. The HPLC system comprised an Agilent HP1100 equipped with a Hyperclone 3 micron BDS C18 130A column 150 mm×4.6 mm (Phenomenex) heated to 50° C. The gradient elution was from 55% mobile phase B to 95% mobile phase B over 10 minutes followed by an isocratic hold at 95% mobile phase B for 2 minutes with a flow rate of 1 mL/min. Mobile phase A was 10% acetonitrile:90% water, containing 10 mM ammonium acetate and 0.1% trifluoroacetic acid, mobile phase B was 90% acetonitrile:10% water, containing 10 mM ammonium acetate and 0.1% trifluoroacetic acid. Rapamycin analogues were identified by the presence of the characteristic rapamycin triene, centred on λ=278 nm or by LC-MS.

LC-MS—method 1 (fermentation broths)—The HPLC system described above was coupled to a Bruker Daltonics Esquire3000 electrospray mass spectrometer. The gradient elution was from 50% mobile phase B to 100% mobile phase B over 10 minutes followed by an isocratic hold at 100% mobile phase B for 3 minutes with a flow rate of 1 mL/min. Mobile phase A was water containing 0.1% formic acid, mobile phase B was acetonitrile containing 0.1% formic acid. Positive negative switching was used over a scan range of 500 to 1000 Dalton.

LC-MS—method 2 (purified samples)—LC-MS—method 1 (fermentation broths)—The HPLC system described above was coupled to a Bruker Daltonics Esquire3000 electrospray mass spectrometer. Chromatography was achieved over a Phenomenex HyperClone $C_{18}$-BDS column (4.6×150 mm, 3 micron particle size) eluting with a gradient of water+0.1% formic acid:acetonitrile+0.1% formic acid, (90:10) to (0:100), at 1 mL/min over 20 min. Purity was assessed by MS and at multiple wavelengths (210, 254 & 276 nm). All compounds were >95% pure at all wavelengths Example 1

Generation of Constructs Able to Induce Deletion or Expansion of the Rapamycin PKS Modules and Transfer to S. rapamycinicus To construct a downstream region of homology two PCR products were ligated together. The first of these two PCR products was obtained using two oligonucleotides (CGACGAATTCCATCGCGCCCCGGCCCGCCAGG (SEQ ID NO: 1) and TTGTCCGGCCGGGTGTCGTACGTCTTCGG (SEQ ID NO: 2) to amplify a ~1.5 kb region of the rapamycin gene cluster using Cos25 (Schwecke et al., 1995) as the template. The second of the two products was obtained using oligonucleotides (CCAGGGACGAGGAGCACGCCGTGTCCATCG (SEQ ID NO: 3) and GGGGTGTAGAGGCTAGCCGCCCTGGCACCGGCCGAGC (SEQ ID NO: 4)) to amplify a ~0.8 kb region of the rapamycin gene cluster again using Cos25 as the template. Each of these PCR products was treated with T4 polynucleotide kinase and cloned into pUC19 before sequencing to verify the amplified fragment. The first fragment was excised using EcoRI and ApaI and the second fragment excised using ApaI and XbaI (from the pUC19 polylinker) and ligated together with pUC19 that had been digested with EcoRI and XbaI. This plasmid was designated intermediate plasmid 1.

Similarly, to construct the upstream region of homology a further two PCR products were ligated together The first of these two PCR products was obtained using two oligonucleotides (GTATCTAGAAAGATCTAGTACCCGGGTTGTGGCGGTGCCGAGG (SEQ ID NO: 5) and TCAGGCCGCCTCGGGCGTGTCGGTTGTCATCAAGATGG (SEQ ID NO: 6)) to amplify a ~1.5 kb region of the rapamycin gene cluster using Cos25 as the template. The second of the two products was obtained using oligonucleotides (GACGGCTCATCCACGTGCAGGGTGCGGGGAACC (SEQ ID NO: 7) and GTCTAAGCTTTCCCCACCGACCGTGGCTGGGACGTCG (SEQ ID NO: 8)) to amplify a ~1 kb region of the rapamycin gene cluster again using Cos25 as the template. Each of these PCR products was kinased using T4 polynucleotide kinase and cloned into pUC19 before sequencing to verify the amplified fragment. The first fragment was excised using XbaI and PstI and the second fragment excised using PstI and HindIII and ligated together with pUC19 that had been digested with XbaI and HindIII. This plasmid was designated intermediate plasmid 2.

The region of downstream homology from intermediate plasmid 1 was excised using EcoRI and XbaI. The region of upstream homology from intermediate plasmid 2 was excised using XbaI and HindIII. These two fragments were ligated together with pUC19 that had been digested with EcoRI and HindIII. The resulting vector was then digested with NheI and Bg/II to insert the desired reductive loop. Two loops were used, the reductive loop from module 13 of the rapamycin cluster and the reductive loop from module 11 of the rapamycin cluster. NheI/Bg/II sites were utilised. The reductive loop of module 13 of the rapamycin cluster was excised from plasmid pPF137 (Gaisser et al., 2003) using NheI and Bg/II. The reductive loop of module 11 of the rapamycin cluster was excised from plasmid pWV165 (a plasmid containing the rapamycin PKS module 11 reductive loop engineered to have NheI and Bg/II sites surrounding the reductive loop encoding DNA.

The resulting constructs were transferred to the conjugative vector pKC1139 (Bierman et al 1992) by digesting with EcoRI and HindIII and ligating with pKC1139 that had been digested with the same enzymes. The resulting plasmids were named pSGK210 (containing rapamycin PKS module 13 loop) and pSGK212 (containing rapamycin PKS module 11 loop).

Plasmids pSGK210 and pSGK212 were transferred to S. rapamycinicus BIOT-4010 (Kendrew et al., 2013) by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 ml 2TY liquid medium containing apramycin (50 µg/mL), kanamycin (25 µg/mL) and chloramphenicol (25 µg/ml). 0.7 ml of this culture was used to inoculate 10 ml liquid medium containing apramycin (50 µg/ml), kanamycin (25 µg/ml) and chloramphenicol (25 µg/mL) and grown at 37 C to reach an OD of approximately 0.5. Cells were pelleted at 4000 rpm for 10 minutes and washed twice with 10 ml 2×TY before resuspending in 0.25 mL 2 TY. Spores of S. rapamycinicus BIOT-4010 grown on ISP3 for 2-3 weeks were harvested using 20% glycerol and stored at −80° C. (1 plate gives about 1 mL spore stock). For the conjugation approximately 0.3-0.5 mL of these spores are needed for each conjugation. Spores were unfrozen and pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 mL of washed *E. coli* cells to the heat shocked spores, mixing and spreading the mixture onto a R6 plate and transferring to 37° C. The plate was overlaid with 2 mL water containing 15 μL naladixic acid (stock 50 mg/mL) after 2-3 hours and with 2 mL water containing 15 μL apramycin (stock 100 mg/mL) after an overnight incubation.

Plates were incubated at 37° C. until single exconjugant colonies were visible. Colonies (approximately 15-20) were patched to MAM containing apramycin and naladixic acid and reincubated at 37° C. Usually this colony was then repatched to the same media (containing apramycin and nalidixic acid) to ensure there was no *E. coli* contamination. Once stabilised approximately 10-15 of the strains were patched to solid ISP3 media lacking antibiotics and incubated at 37° C. for approximately 3 days before repatching to ISP3 media and growing for a further 3 or 4 days. A final round of subculture at 37° C. on ISP3 was performed before plating to ISP3 and leaving at 28° C. for to allow the strain to sporulate (~10-14 days). Spores were harvested in 20% glycerol and a dilution series prepared in water and spread onto ISP3 media before incubating at 28° C. Once individual sporulating colonies were visible they were patched to ISP3 media plus and minus apramycin to assess for loss of plasmid. The vast majority of strains had lost the apramycin marker. Strains that had lost the marker were tested by growing in production media to assess whether they still produced 39-desmethoxy rapamycin (i.e. had reverted to original strain). Among the strains that no longer produced the original compound 39-desmethoxy rapamycin strains that produced novel compounds were identified (see Example 3).

Example 2

Generation of an Alternative Construct Able to Induce Deletion of the Rapamycin PKS Modules and Transfer to *S. rapamycinicus*

A series of alternative constructs were prepared to assess the effect of smaller regions (~1 kb) of homology for recombination.

Two oligonucleotides CGCGAATTCGGAGAAACCGGCACCGTCCGCACT-GTCCGC (SEQ ID NO: 9) and GGGGTGTAGAG-GCTAGCCGCCCTGGCACCGGCCGAGC (SEQ ID NO: 4) were used to amplify a ~1 kb region of homology using intermediate plasmid 1 as a template. The resulting PCR product was kinased using T4 polynucleotide kinase and cloned into pUC19 before sequencing to verify the amplified fragment. The fragment was then excised using EcoR1 and XbaI. CGTAAAGCTTGGAGACGACACCGTCACCGGCAC-CGCTGTG (SEQ ID NO: 10) and GTATCTA-GAAAGATCTAGTACCCGGGTTGTGGCGGTGC-CGAGG (SEQ ID NO: 5) were used to amplify a ~1 kb region of homology using intermediate plasmid 2 as a template. The resulting PCR product was kinased using T4 polynucleotide kinase and cloned into pUC19 before sequencing to verify the amplified fragment. The fragment was then excised using HindIII and XbaI.

The excised fragments were ligated together with pUC19 that had been digested with EcoRI and HindIII. The resulting vector was then digested with NheI and Bg/II to insert the desired rapamycin PKS module 11 reductive loop as outlined previously (see Example 1).

The resulting construct was transferred to the conjugative replacement vector pKC1139 (Bierman et al., 1992) by digesting with EcoRI and HindIII and ligating with pKC1139 that had been digested with the same enzymes.

Plasmid pSGK234 was transferred to *S. rapamycinicus* BIOT-4010 by conjugation using standard methods. Briefly, plasmid was electroporated into ET12567:pUZ8002 and selected on 2TY agar medium containing apramycin (50 μg/mL), kanamycin (25 μg/mL), and chloramphenicol (25 μg/mL). Single colonies were grown overnight in 3 mL 2×TY liquid medium containing apramycin (50 μg/mL), kanamycin (25 μg/mL) and chloramphenicol (25 μg/mL). 0.7 mL of this culture was used to inoculate 10 mL liquid medium containing apramycin (50 μg/mL), kanamycin (25 μg/mL) and chloramphenicol (25 μg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. rapamycinicus* BIOT-4010 grown on ISP3 for 2-3 weeks were harvested using 20% glycerol and stored at −80° C. (1 plate gives about 1 mL spore stock). For the conjugation approximately 0.3-0.5 mL of these spores are needed for each conjugation. Spores were unfrozen and pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 ml of washed *E. coli* cells to the heat shocked spores, mixing and spreading the mixture onto a R6 plate and transferring to 37 C. The plate was overlaid with 2 ml water containing 15 μL naladixic acid (stock 50 mg/ml) after 2-3 hours and with 2 mL water containing 15 μL apramycin (stock 100 mg/mL) after an overnight incubation.

Plates were incubated at 37° C. until single exconjugant colonies were visible. Colonies (approximately 10-20) were patched to MAM containing apramycin and naladixic acid and reincubated at 37° C. Usually this colony was then repatched to the same media (containing apramycin and nalidixic acid) to ensure there was no *E. coli* contamination. Once stabilised approximately 10-15 of the strains were patched to solid ISP3 media lacking antibiotics and incubated at 37° C. for approximately 3 days before repatching to ISP3 media and growing for a further 3 or 4 days. A final round of subculture at 37° C. on ISP3 was performed before plating to ISP3 and leaving at 28° C. for to allow the strain to sporulate (~10-14 days). Spores were harvested in 20% glycerol and a dilution series prepared in water and spread onto ISP3 media before incubating at 28° C. Once individual sporulating colonies were visible they were patched to ISP3 media plus and minus apramycin to assess for loss of plasmid. The vast majority of strains had lost the apramycin marker. Strains that had lost the marker were tested by growing in production media to assess whether they still produced 39-desmethoxy rapamycin (i.e. had reverted to original strain). Among the strains that no longer produced the original compound 39-desmethoxy rapamycin strains that produced novel compounds were identified (see Example 3).

Example 3

Testing the Genetically Engineered Strains for Production of Novel Contracted Compounds Typically 10-15 colonies displaying apramycin sensitivity and derived from each of the primaries were taken forward.

Patches were typically grown for around 10-14 days to allow significant mycelial growth and sporulation. An agar plug (about 5 mM in diameter) from each patch was used to inoculate a seed falcon tube containing 7 ml RapV7 media (in a falcon tube) and incubated at 28° C., 300 rpm (1 inch throw) for 48 hours. 0.5 mL of this seed culture was used to inoculate 7 mL MD6 media and incubated at 26° C. and 300 rpm for 6 days; 24 hours into this time each culture was supplemented with 50 µl of 0.32M cyclohexane carboxylic acid (CHCA) in methanol (final concentration in media 2 mM).

For harvest and product analysis 0.9 ml of culture was aliquoted into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS.

Example 4

Diversifying Compounds Produced from Module Deleted Strains by Mutasynthetic Experiments As the strains were constructed in a *S. rapamycinicus* strain that had previously had the rapK gene deleted to interrupt starter unit provision we were able to use a mutasynthetic-feeding approach to further diversify the range of compounds from these strains and produce compounds that possessed the expected contracted polyketide skeleton but bore an altered starter unit. We could also often observe compounds with masses corresponding to different levels of post PKS processing.

Example 5.1

Diversifying Compounds from the −1 PKS Module Strain (Phenotype B) by Mutasynthetic Experiments The isolated strain with phenotype B was grown on ISP3 media for approximately 2-3 weeks to allow significant mycelial growth and sporulation. Spores were harvested in 20% glycerol and aliquoted to produce a working stock of spores that was frozen at 80 C. 0.25 ml of the spore stock was used to inoculate 50 mL RapV7 in a 250 mL flask and incubated at 28° C. at 250 rpm? for 48 hours. 0.5 mL of this seed culture was used to inoculate 7 mL MD6 media in a falcon tube and incubated at 26° C. and 300 rpm for 6 days, 24 hours into this time each culture was supplemented with 50 µl of 0.32M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 2 illustrates the amounts produced (mg/L using 39-desmethoxy rapamycin callibration curve) and range of compounds and masses observed in these mutasynthetic experiments. Where a mass was not recorded, NR replaces the number.

Example 5.2

Diversifying Compounds from the −2 PKS Module Strain (Phenotype C) by Mutasynthetic Experiments The isolated strain with phenotype C was grown on ISP3 media for approximately 2-3 weeks to allow significant mycelial growth and sporulation. Spores were harvested in 20% glycerol and aliquoted to produce a working stock of spores that was frozen at 80 C. 0.25 ml of the spore stock was used to inoculate 50 mL RapV7 in a 250 mL flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 µL of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 3 illustrates the amounts produced (mg/L using 39-desmethoxy rapamycin callibration curve) and range of compounds and masses observed in these mutasynthetic experiments. Where a mass was not recorded, NR replaces the number.

Example 5.3

Diversifying Compounds from the −3 PKS Module Strain (Phenotype D) by Mutasynthetic Experiments The isolated strain with phenotype D was grown on ISP3 media for approximately 2-3 weeks to allow significant mycelial growth and sporulation. Spores were harvested in 20% glycerol and aliquoted to produce a working stock of spores that was frozen at 80° C. 0.25 mL of the spore stock was used to inoculate 50 mL RapV7 in a 250 ml flask and incubated at 28° C. at 250 rpm for 48 hours. 0.5 ml of this seed culture was used to inoculate 7 mL MD6 media in a falcon tube and incubated at 26° C. and 300 rpm for 6 days, 24 hours into this time each culture was supplemented with 50 µl of 0.32M novel starter unit (see Table 1) dissolved in methanol (final concentration in media 2 mM). Each starter acid was tested in duplicate for each strain. After the 6 days of production 0.9 mL of culture was transferred into a 2 ml eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 4 illustrates the amounts produced (mg/L using 39-desmethoxy rapamycin callibration curve) and range of compounds and masses observed in these mutasynthetic experiments. Where a mass was not recorded, NR replaces the number.

Example 5.4

Diversifying Compounds from the −4 PKS Module Strain (Phenotype E) by Mutasynthetic Experiments The isolated strain with phenotype E was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 mL flask and incubated at 28° C. at 250 rpm for 48 hours. 0.5 ml of this seed culture was used to inoculate 7 mL MD6 media in a falcon tube and incubated at 26° C. and 300 rpm for 6 days, 24 hours into this time each culture was supplemented with 50 µl of 0.32M novel starter unit (see Table 1) dissolved in methanol (final concentration in media 2 mM). Each starter acid was tested in duplicate for each strain. After the 6 days of production 0.9 ml of culture was aliquoted into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 5 illustrates the amounts produced (mg/L using 39-desmethoxy rapamycin callibration curve) and range of compounds and masses observed in these mutasynthetic experiments. Where a mass was not recorded, NR replaces the number.

Example 5.5

Diversifying Compounds from the −6 PKS Module Strain (Phenotype F) by Mutasynthetic Experiments The isolated strain with phenotype F was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 ml flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 µl of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 6 illustrates the amounts produced (mg/L using 39-desmethoxy rapamycin callibration curve) and range of compounds and masses observed in these mutasynthetic experiments. Where a mass was not recorded, NR replaces the number.

Example 6

Diversifying Compounds from the +1 PKS Module Strain (Phenotype A) by Mutasynthetic Experiments The isolated strain with phenotype A was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 ml flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 µl of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS.

Example 7

Isolation of Compounds 2 and 3

Strain: Phenotype G from BIOT-4827
Feed: 4-trans-hydroxylcyclohexanecarboxylic acid (final concentration 2 mM)
1×15 liter fermentation The fermentation was as described above except that the vegetative cultures (seed cultures) were prepared using 12×5 mm plugs from an agar plate and inoculating into 400 ml medium RapV7 in 2 liter Erlenmeyer flasks with foam plugs. Cultivation was carried out for 48 hours at 28° C., 250 rpm (2.5 cm throw).

DSP was as described in the general section, both the cell mass and clarified broth were extracted and the crude extracts combined.

The crude extract (13.8 g) was dissolved in 1:1 methanol/acetonitrile and C18 reverse-phase silica added (26 g). The solvent was removed in vacuo and the silica added to a C18 reverse-phase silica open column (70 mm×50 mm diameter) and the column eluted with 3:2 water/acetonitrile (600 ml), 1:1 water/acetonitrile (400 ml), 2:3 water/acetonitrile (1000 ml). Fractions combining compound 2 were pooled and taken to dryness (6.0 g) and fractions containing compound 3 were combined and taken to dryness (9.4 g).

Compound 2 was then purified by dissolving the 6.0 g enriched extract in methanol (5 ml) and separating the mixture by size-exclusion chromatography over sephadex LH-20 (column dimensions 1000 mm×30 mm diameter) eluted with methanol. Fractions containing compound 2 were combined and taken to dryness (210 mg), before the being adsorbed onto C18 reverse-phase silica (dissolved in 20 ml methanol, add 2 g C18 silica and remove the solvent in vacuo). This was then added to a C18 silica column (100 mm×30 mm diameter) and eluted with 3:2 acetonitrile/water. The fractions containing compound 2 were combined and taken to dryness to yield compound 2 as a white, amorphous solid.

QC data. RT=10.7 minutes, m/z=584.2 ([M+Na]$^+$) and 560.2 ([M−H]$^-$)

NMR was shown to be consistent with the structure shown:

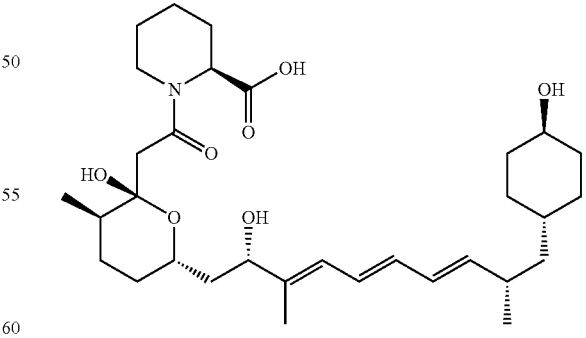

Compound 3 was then purified by dissolving the 9.4 g enriched extract in methanol (5 ml) and separating the mixture by size-exclusion chromatography over sephadex LH-20 (column dimensions 1000 mm×30 mm diameter) eluted with methanol. Fractions containing compound 3 were combined and taken to dryness.

QC data. RT 13.5 minutes, m/z=598.2 ([M+Na]⁺) and 574.1 ([M–H]⁻)

NMR was shown to be consistent with the structure shown:

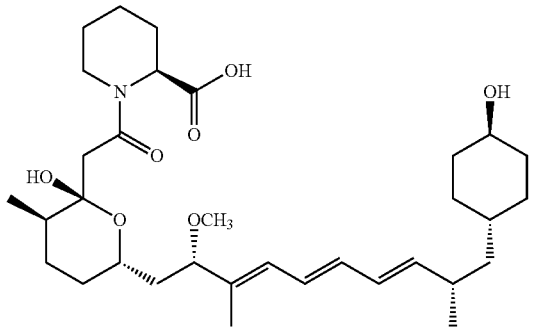 [SMILES: CO[C@@H](C[C@@H]1CC[C@@H](C)[C@](O)(CC(=O)N2CCCC[C@H]2C(=O)O)O1)/C(C)=C/C=C/C=C/[C@@H](C)C[C@H]1CC[C@H](O)CC1]

Example 8

Isolation of Compound 4

Strain: Phenotype C from BIOT-4827
Feed: 4-trans-hydroxylcyclohexanecarboxylic acid (final concentration 2 mM)
80×7 ml fermentation (in falcon tubes)

The broths from the individual falcons were combined and the cell mass separated by centrifugation. The DSP was carried out as described above, with only the cell mass extracted. The crude extract (1.2 g) was dissolved in ethyl acetate and silica gel added (10 g). the solvent was removed in vacuo and the adsorbed silica was applied to a flash silica column (180 mm×55 mm diameter). The column was eluted with 4:5 ethyl acetate/hexanes (1.3 liters) then 1:1 ethyl acetate/hexanes (3.4 liters). The fractions containing compound 4 were combined and reduced in vacuo (65 mg). This material was further purified by reverse-phase HPLC (Phenomenex Xterra C18 column, 10 micron, 19 mm diameter× 250 mm, mobile phase at 20 ml/min, A=water, B=acetonitrile, t=0 min, B=50%; t=22 mins, B=80%). Fractions containing compound 4 were combined and taken to dryness to yield the target compound as a white amorphous solid (47 mg).

QC data. RT=15.5 minutes, m/z=780.3 ([M+Na]⁺) and 756.2 ([M–H]⁻)

NMR was shown to be consistent with the structure shown:

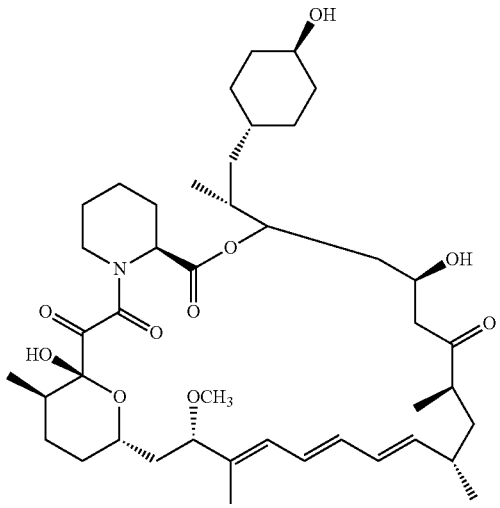 [SMILES: CO[C@H]1C[C@@H]2CC[C@@H](C)[C@@](O)(O2)C(=O)C(=O)N2CCCC[C@H]2C(=O)OC([C@H](C)C[C@H]2CC[C@H](O)CC2)C[C@@H](O)CC(=O)[C@H](C)C[C@H](C)/C=C/C=C/C=C/1C]

Example 9

Isolation of Compound 5

Strain: Phenotype B from BIOT-4827
Feed: 4-trans-hydroxylcyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract was dissolved in ethyl acetate and silica gel added (7.5 g). The solvent was removed in vacuo and the adsorbed silica was applied to a flash silica column (200 mm×55 mm diameter). The column was eluted with 4:5 ethyl acetate/hexanes (1.8 liters), 1:1 ethyl acetate/hexanes (3.0 liters), 3:2 ethyl acetate/hexanes (1.5 liters) and then 2:1 ethyl acetate/hexanes (0.9 liters). The fractions containing compound 5 were combined and reduced in vacuo (44 mg). This material was further purified by reverse-phase HPLC (Phenomenex Xterra C18 column, 10 micron, 19 mm diameter×250 mm, mobile phase at 20 ml/min, A=water, B=acetonitrile, t=0 min, B=50%; t=22 mins, B=80%). Fractions containing compound 5 were combined and taken to dryness to yield the target compound as a white amorphous solid (32.6 mg).

QC data. RT=14.8 minutes, m/z=820.7 ([M+Na]⁺) and 796.4 ([M–H]⁻)

NMR was shown to be consistent with the structure shown:

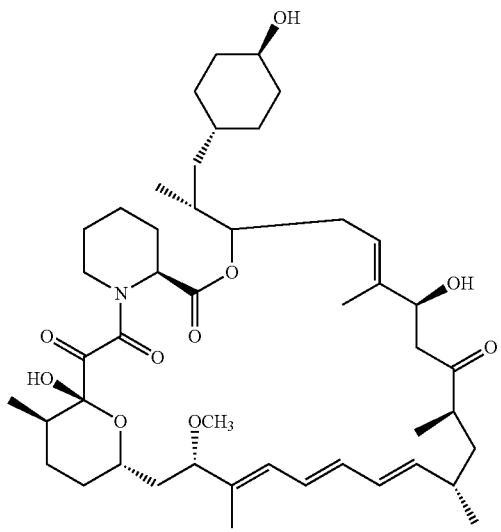 [SMILES: CO[C@H]1C[C@@H]2CC[C@@H](C)[C@@](O)(O2)C(=O)C(=O)N2CCCC[C@H]2C(=O)OC([C@H](C)C[C@H]2CC[C@H](O)CC2)C/C=C(\C)[C@@H](O)CC(=O)[C@H](C)C[C@H](C)/C=C/C=C/C=C/1C]

Example 10

Isolation of Compound 6

Strain: Phenotype D from BIOT-4827
Feed: 4-trans-hydroxylcyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract (8 g) was dissolved in ethyl acetate and silica gel added (15 g). The solvent was removed in vacuo and the adsorbed silica was applied to a flash silica column (200 mm×55 mm diameter). The column was eluted with 1:2 ethyl acetate/hexanes (0.9 liters), 4:5 ethyl acetate/hexanes (1.8 liters), 1:1 ethyl acetate/hexanes (3.0 liters), 3:2 ethyl acetate/hexanes (1.0 liters), 2:1 ethyl acetate/hexanes (1.8 liters) and then 100% ethyl acetate (0.4 liters). The fractions containing compound 6 were combined and reduced in vacuo. This material was dissolved in 2:3 acetonitrile/water and applied to a C18 SPE cartridge (20 g). This was eluted with 100 ml of each of 2:3, 1:1, 3:2, 7:3, 4:1 acetonitrile/water. The fractions containing compound 6 were combined and reduced in vacuo (150 mg). This material was further purified by reverse-phase HPLC (Phenomenex Xterra C18 column, 10 micron, 19 mm diameter×250 mm, mobile phase at 20 ml/min, A=water, B=acetonitrile, t=0 min, B=50%; t=22 mins, B=80%). Fractions containing compound 6 were combined and taken to dryness to yield the target compound as a white amorphous solid (93 mg).

QC data. RT=14.3 minutes, m/z=722.6 ([M+Na]$^+$) and 698.5 ([M–H]$^-$)

NMR was shown to be consistent with the structure shown:

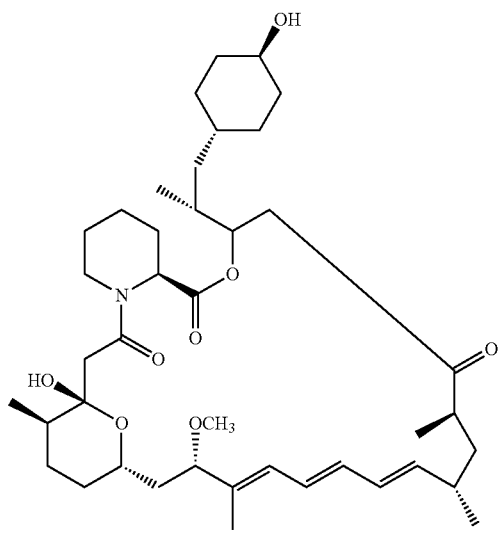 [SMILES: CO[C@H]1C[C@@H]2CC[C@@H](C)[C@](O)(CC(=O)N3CCCC[C@H]3C(=O)OC([C@H](C)C[C@H]3CC[C@H](O)CC3)CC(=O)[C@H](C)C[C@H](C)/C=C/C=C/C=C/1C)O2]

Example 11

Isolation of Compound 7

Strain: Phenotype E from BIOT-4827
Feed: 4-trans-hydroxylcyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract (9.8 g) was dissolved in 1:1 methanol/acetonitrile and C18 reverse-phase silica gel added. The solvent was removed in vacuo and the adsorbed silica was applied to a flash reverse-phase C18 silica column (70 mm×55 mm diameter). The column was eluted with 6:4 water/acetonitrile (0.8 liters), 1:1 water/acetonitrile (0.2 liters), 4:6 water/acetonitrile (0.8 liters), and then 3:7 water/acetonitrile (0.2 liters). The fractions containing compound 7 were combined and reduced in vacuo (404 mg). This material was further purified by reverse-phase HPLC (Phenomenex Xterra C18 column, 10 micron, 19 mm diameter× 250 mm, mobile phase at 20 ml/min, A=water, B=acetonitrile, t=0 min, B=30%; t=30 mins, B=80%). Fractions containing compound 7 were combined and taken to dryness in vacuo. This material was by size-exclusion chromatography over sephadex LH-20 (column dimensions 1000 mm×30 mm diameter) eluted with methanol. Fractions containing compound 7 were combined and taken to dryness to yield the target compound as a white amorphous solid (47 mg).

QC data. RT=12.7 minutes, m/z=652.6 ([M+Na]$^+$) and 628.5 ([M–H]$^-$)

NMR was shown to be consistent with the structure shown:

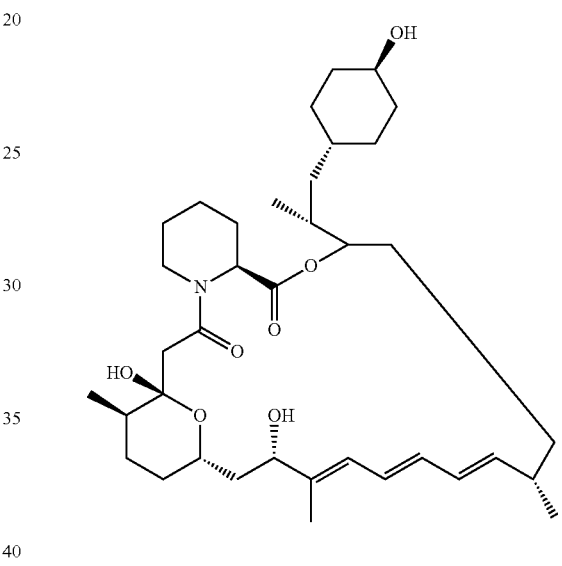

Example 12

Isolation of Compounds 8, 9, 10 and 11

Strain: Phenotype B from BIOT-4827
Feed: 3,4-trans-dihydroxylcyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract (8.5 g) was dissolved in 80% aqueous methanol (250 ml) and washed with hexanes (2×250 ml). The aqueous methanol was reduced in vacuo to yield an enriched extract (6.8 g). The crude extract was dissolved in methanol and silica added. The solvent was removed in vacuo and the adsorbed silica added added to a flash silica column (20 cm×5 cm diameter) and eluted with 100% chloroform, and the polarity gradually increased by adding MeOH (to a maximum 5% MeOH). Fractions contain compound 8 were combined and taken to dryness (3.1 g). Fractions contain compound 9 were combined and taken to dryness (196 mg). Fractions contain compound 10 were combined and taken to dryness (480 mg). Fractions contain compound 11 were combined and taken to dryness (304 mg).

The extract containing compound 8 was then purified further by flash silica column chromatography eluted with ethyl acetate/hexane. Fractions contain compound 8 were combined and taken to dryness to yield the target compound as a white amorphous solid (65 mg).

QC data. RT=15.9 minutes, m/z=850.8 ([M+Na]$^+$) and 826.5 ([M−H]$^−$)

NMR was shown to be consistent with the structure shown:

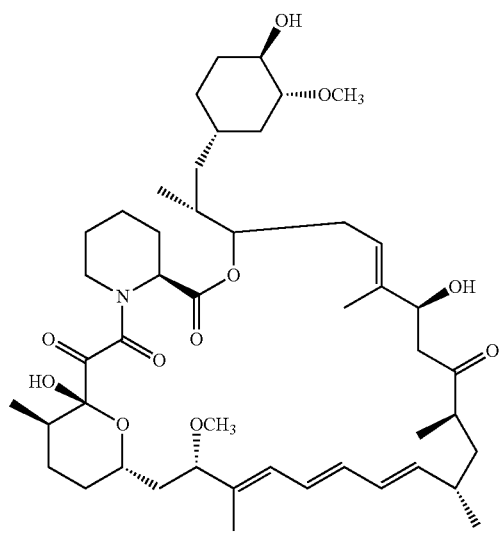 [SMILES: CO[C@H]1C[C@@H]2CC[C@@H](C)[C@@](O)(O2)C(=O)C(=O)N2CCCC[C@H]2C(=O)OC([C@H](C)C[C@@H]2CC[C@@H](O)[C@H](OC)C2)C/C=C(\C)[C@@H](O)CC(=O)[C@H](C)C[C@H](C)/C=C/C=C/C=C/1C]

The extract containing compound 9 was then purified further by reverse-phase HPLC (Phenomenex Xterra C18 column, 10 micron, 19 mm diameter×250 mm, mobile phase at 20 ml/min, A=water, B=acetonitrile) to yield the target compound as a white amorphous solid (55 mg).

QC data. RT=14.7 minutes, m/z=822.8 ([M+Na]$^+$) and 798.6 ([M−H]$^−$)

NMR was shown to be consistent with the structure shown:

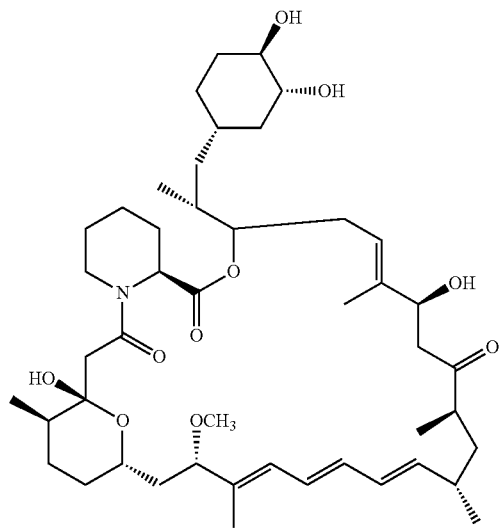 [SMILES: CO[C@H]1C[C@@H]2CC[C@@H](C)[C@](O)(CC(=O)N3CCCC[C@H]3C(=O)OC([C@H](C)C[C@@H]3CC[C@@H](O)[C@H](O)C3)C/C=C(\C)[C@@H](O)CC(=O)[C@H](C)C[C@H](C)/C=C/C=C/C=C/1C)O2]

The extract containing compound 10 was then purified further by reverse-phase HPLC (Phenomenex Xterra C18 column, 10 micron, 19 mm diameter×250 mm, mobile phase at 20 ml/min, A=water, B=acetonitrile) to yield the target compound as a white amorphous solid (211 mg).

QC data. RT=14.2 minutes, m/z=836.8 ([M+Na]$^+$) and 812.5 ([M−H]$^−$)

NMR was shown to be consistent with the structure shown:

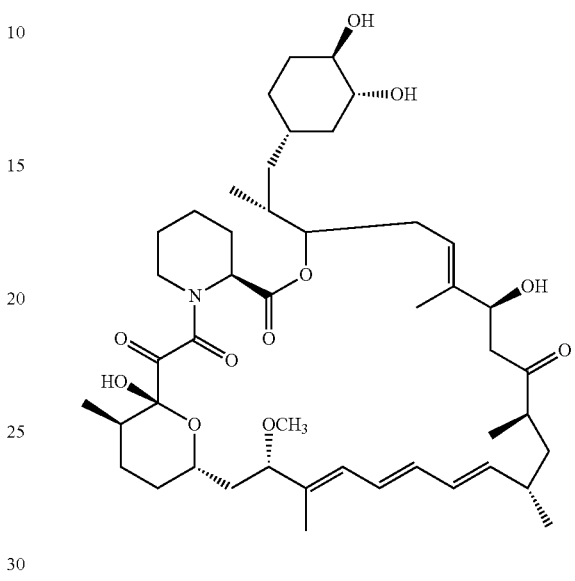

The extract containing compound 11 was then purified further by reverse-phase HPLC (Phenomenex Xterra C18 column, 10 micron, 19 mm diameter×250 mm, mobile phase at 20 ml/min, A=water, B=acetonitrile) to yield the compound 11 as a white amorphous solid (55 mg).

QC data. RT=13.0 minutes and 14.2 minutes, m/z=822.6 ([M+Na]$^+$) and 798.5 ([M−H]$^−$)

NMR was shown to be consistent with the structure shown:

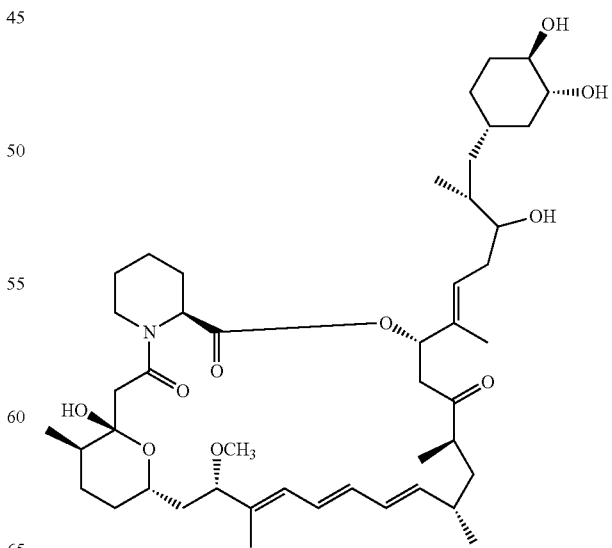

Example 13

Isolation of Compound 12

Strain: Phenotype B from BIOT-4827
Feed: 5-methylthiophene-2-carboxylic acid (final concentration 2 mM)
1×15 liter fermentation
The fermentation was as described above.
The fermentation broth at the end of the fermentation was separated by centrifugation and the cell paste processed as described above.
The crude extract (6.7 g) was dissolved in methanol and silica added. The solvent was removed in vacuo and the adsorbed silica added added to a flash silica column (20 cm×5 cm diameter) and eluted with 100% chloroform. Fractions containing the target compound were combined and dried in vacuo (2.14 g). This enriched extract was loaded onto a second silica column, pre-conditioned in 1:1 ethyl acetate/hexanes. The column was eluted with the same solvent mixture and fractions containing the target compound were combined and dried in vacuo (0.42 g). The extract containing compound 12 was then purified further by reverse-phase HPLC (Phenomenex Xterra C18 column, 10 micron, 19 mm diameter×250 mm, mobile phase at 20 ml/min, A=water, B=acetonitrile, t=0 minutes, B=50%, t=30 minutes, B=100%) to yield the compound 12 as a white amorphous solid (256 mg).

QC data. RT=12.7 minutes, m/z=834.4 ([M+Na]$^+$) and 810.2 ([M−H]$^−$)

NMR was shown to be consistent with the structure shown:

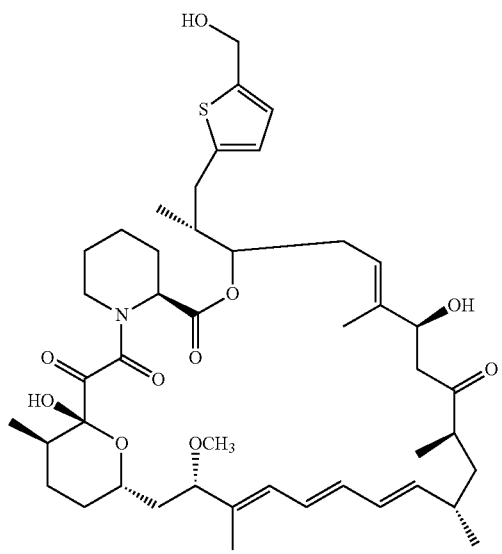 [SMILES: CO[C@H]1C[C@@H]2CC[C@@H](C)[C@@](O)(O2)C(=O)C(=O)N2CCCC[C@H]2C(=O)OC([C@H](C)Cc2ccc(CO)s2)C/C=C(\C)[C@@H](O)CC(=O)[C@H](C)C[C@H](C)/C=C/C=C/C=C/1C]

Example 14

Isolation of Compound 13

Strain: Phenotype B from BIOT-4827
Feed: isonicotinic acid (final concentration 2 mM)
1×15 liter fermentation
The fermentation was as described above.
The fermentation broth at the end of the fermentation was separated by centrifugation and the cell paste processed as described above.

The crude extract (5.3 g) was dissolved in methanol and silica added. The solvent was removed in vacuo and the adsorbed silica added added to a flash silica column (20 cm×5 cm diameter) and eluted with 100% chloroform, 1% methanol/chloroform, 2% methanol/chloroform, 3% methanol/chloroform, 4% methanol/chloroform and 5% methanol/chloroform. Fractions containing the target compound were combined and dried in vacuo (1.99 g). This enriched extract was loaded onto a second silica column, pre-conditioned in 1:1 ethyl acetate/hexanes. The column was eluted with the same solvent mixture and then 60:40, 70:30, 80:20, 90:10 mixtures followed by 100% ethyl acetate. Fractions containing the target compound were combined and dried in vacuo to yield the compound 13 as an amorphous solid (0.124 g).

All analytics for compound 13 were performed using an Agilent Zorbax, Eclipse XDB-C8 column (150×4.6 mm, 5 micron). All of the LC-timetables were the same as in the other Examples.

QC data. RT=11.6 minutes, m/z=777.7 ([M+H]$^+$) and 775.4 ([M−H]$^−$)

NMR was shown to be consistent with the structure shown:

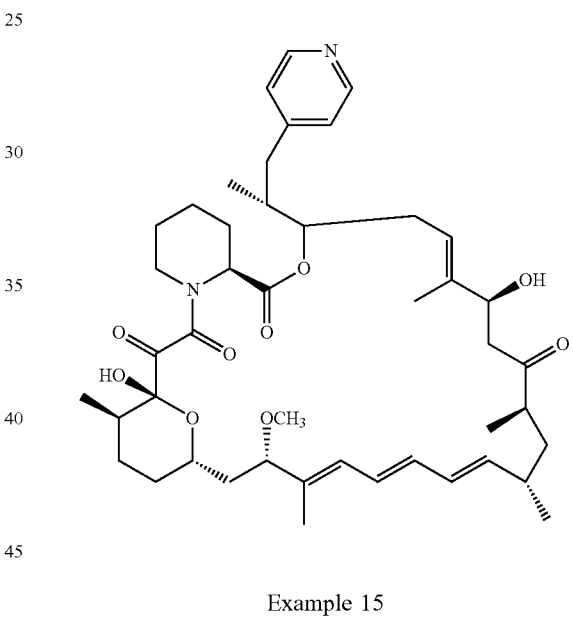

Example 15

Isolation of Compound 14

Strain: Phenotype A from BIOT-4827
Feed: 4-trans-hydroxycyclohexanecarboxylic acid (final concentration 2 mM)
1×15 liter fermentation
The fermentation was as described above.
The fermentation broth at the end of the fermentation was separated by centrifugation and the cell paste processed as described above.
The crude extract (5.3 g) was dissolved in methanol and silica added. The solvent was removed in vacuo and the adsorbed silica added added to a flash silica column (20 cm×5 cm diameter) and eluted with the 50:50 ethyl acetate/hexanes and then 60:40, 70:30, 80:20, 90:10 mixtures followed by 100% ethyl acetate. Fractions containing the target compound were combined and dried in vacuo to yield an enriched extract of 0.05 g. This material was loaded onto a second silica column (10 cm×2 cm) and eluted with 45% ethyl acetate/55% hexanes. Fractions containing the target compound were combined and dried in vacuo (32 mg). This was then purified further by reverse-phase HPLC (Phenomenex Xterra C18 column, 10 micron, 19 mm diameter×250 mm, mobile phase at 20 ml/min, A=water, B=acetonitrile, t=0 minutes, B=50%, t=30 minutes, B=100%) and then by further reverse-phase HPLC (Phenomenex Gemini NX C18 column, 10 micron, 21 mm diameter×150 mm, mobile phase at 20 ml/min, A=water, B=acetonitrile, t=0 minutes, B=50%, t=30 minutes, B=100%) to yield compound 14 as a white amorphous solid (14.5 mg).

QC data. RT=15.2 minutes, m/z=920.6 ([M+Na]$^+$) and 896.5 ([M−H]$^-$)

NMR was shown to be consistent with the structure shown:

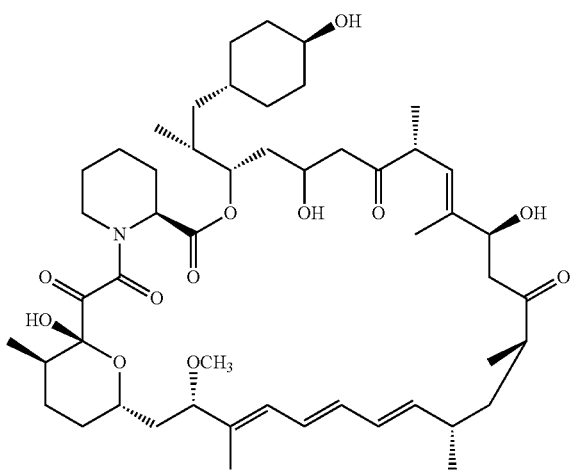 [SMILES: CO[C@H]1C[C@@H]2CC[C@@H](C)[C@@](O)(O2)C(=O)C(=O)N2CCCC[C@H]2C(=O)O[C@H]([C@H](C)C[C@H]2CC[C@H](O)CC2)CC(O)CC(=O)[C@H](C)/C=C(\C)[C@@H](O)CC(=O)[C@@H](C)C[C@H](C)/C=C/C=C/C=C/1C]

Example 16

Isolation of Compounds 15, 16 and 17

Strain: Phenotype F from BIOT-4827
Feed: 4-trans-hydroxycyclohexanecarboxylic acid (final concentration 2 mM)
1×15 liter fermentation
The fermentation was as described above.
The fermentation broth at the end of the fermentation was separated by centrifugation and the cell paste and clarified broth processed as described above.

The crude extract (20.7 g) was dissolved in methanol and silica added. The solvent was removed in vacuo and the adsorbed silica added added to a flash silica column (20 cm×5 cm diameter) and eluted with the 40:60 ethyl acetate/hexanes and then 50:50, 60:40, 70:30, 80:20, 90:10 mixtures followed by 100% ethyl acetate. Fractions containing the target compounds X+14 and X+15 were combined and dried in vacuo to yield an enriched extract of 0.96 g. Fractions containing the target compounds 17 were combined and dried in vacuo to yield an enriched extract of 3.1 g.

Compounds 15 and 16 were then purified by preparative HPLC (Phenomenex Gemini NX C18 column, 10 micron, 21 mm diameter×150 mm, mobile phase at 20 ml/min, A=water, B=acetonitrile, t=0 minutes, B=60%, t=30 minutes, B=100%) to yield compound X+15 as a white amorphous solid (152 mg). Fractions containing compound 16 was defatted (dissolved in 80% aqueous methanol and extracted into hexanes, the solvent was then removed from the aqueous methanol layer to reveal the target compound) to yield a white amorphous solid (164 mg)

Compound 15

QC data. RT=16.3 minutes, m/z=650.3 ([M+Na]') and 626.2 ([M−H]$^-$)

NMR was shown to be consistent with the structure shown:

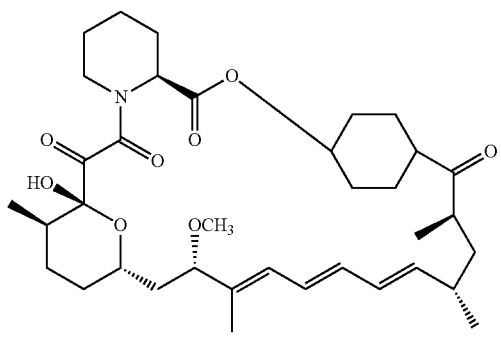 [SMILES: CO[C@H]1C[C@@H]2CC[C@@H](C)[C@@](O)(O2)C(=O)C(=O)N2CCCC[C@H]2C(=O)OC2CCC(CC2)C(=O)[C@H](C)C[C@H](C)/C=C/C=C/C=C/1C]

Compound 16

QC data. RT=14.9 minutes, m/z=636.2 ([M+Na]$^+$) and 612.2 ([M−H]$^-$)

NMR was shown to be consistent with the structure shown:

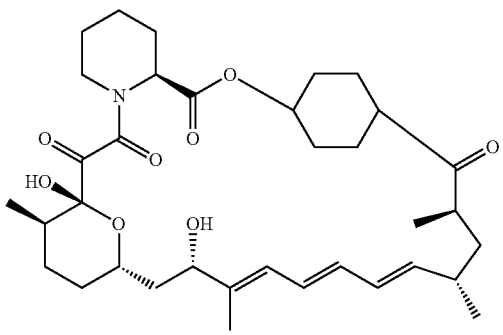 [SMILES: C\C1=C/C=C/C=C/[C@@H](C)C[C@@H](C)C(=O)C2CCC(CC2)OC(=O)[C@@H]2CCCCN2C(=O)C(=O)[C@]2(O)O[C@@H](CC[C@H]2C)C[C@@H]1O]

Compound 17

QC data. RT=13.5 minutes, m/z=654.3 ([M+Na]$^+$) and 630.1 ([M−H]$^-$)

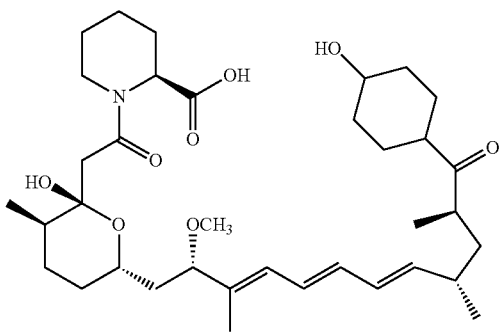 [SMILES: CO[C@@H](C[C@@H]1CC[C@@H](C)[C@](O)(CC(=O)N2CCCC[C@H]2C(=O)O)O1)/C(C)=C/C=C/C=C/[C@@H](C)C[C@@H](C)C(=O)C1CCC(O)CC1]

Example 17

Analytical Biotransformations

See Table 1 for List of Substrate Carboxylic Acids and Carboxylic Acid Analogues Used in the Analytical Biotransformations Analytical biotransformations were conducted as described above in the general methods section and Example 5. In each case the strain being tested was fed each of the compounds above separately. After a total of 6 days growth the broths were extracted as described above and analysed for the production of rapamycin analogues as indicated by observing the rapamycin triplet at 278 nm and/or mass ions that derive from the predicted combination of starter unit and strain. Results are shown in Tables 2 to 6 below.

Results of Mutasynthetic Feeding to −1 PKS Module Strain Phenotype B

TABLE 2

| Feed | major product peaks RT/mins | molecular weight |
|---|---|---|
| unfed | 9.1 | NR |
|  | 10.4 | 791.5 |
| A | 9.4 | NR |
|  | 10.1 | 797.5 |
| B | 8.7 | 813.5 |
|  | 9.6 | 797.5 |
|  | 10.6 | 781.5 |
| C | 8.2 | 813.5 |
|  | 9.8 | 795.5 |
|  | 10.1 | 813.5 |
| D | 8.2 | NR |
|  | 8.7 | NR |
|  | 9.6 | NR |
|  | 10.6 | 797.5 |
|  | 10.8 | 813.5 |
|  | 11.3 | 797.5 |
| E | 8.3 | 811.6 |
|  | 10.2 | 795.5 |
| F | 9.7 | 831.6 |
| G | 8.9 | 843.5 |
|  | 9.5 | 827.5 |
|  | 10.1 | 811.5 |
|  | 10.7 | 811.5 |
| H | 10.1 | 783.5 |
|  | 10.4 | 791.6 |
| I | 7.7 | NR |
|  | 10.1 | 827.2 |
|  | 10.4 | 827.2 |
|  | 10.9 | 811.6 |
| J | 7.1 | NR |
|  | 9.2 | NR |
|  | 9.3 | 825.6 |
|  | 9.8 | 825.6 |
|  | 10.5 | 809.5 |
| K | 7.6 | NR |
|  | 8.2 | NR |
|  | 8.9 | 839.5 |
|  | 9.9 | 839.5 |
|  | 10.4 | 839.5 |
|  | 11.1 | 823.5 |
| L | 9.9 | 769.5 |
|  | 11.7 | 783.4 |
| M | 7.5 | NR |
|  | 8.2 | NR |
|  | 10.4 | 815.5 |
|  | 12.9 | NR |
|  | 13.8 | NR |
| N | 10.4 | 791.5 |
| O | 9.9 | 811.5 |
| P | 5.2 | NR |
|  | 6.2 | NR |
|  | 6.8 | NR |
|  | 7.1 | NR |

TABLE 2-continued

| Feed | major product peaks RT/mins | molecular weight |
|---|---|---|
| Q | 10.4 | 827.5 |
|  | 10.9 | 811.5 |
|  | 11.6 | 825.5 |
| R | 10.5 | 827.5 |
|  | 11.2 | 825.5 |
|  | 11.7 | 809.5 |
| S | 8.5 | NR |
|  | 10.4 | 825.7 |
|  | 10.7 | 809.5 |
| T | 8.9 | 827.6 |
|  | 9.5 | 843.5 |
|  | 10.1 | 827.6 |
|  | 10.7 | 811.5 |
| A1 | 8.3 | NR |
|  | 9.4 | NR |
|  | 10.1 | 797.9 |
|  | 11.5 | 784.1 |
| B1 | 8.7 | NR |
|  | 9.7 | NR |
|  | 10.4 | NR |
|  | 11.9 | 796.2 |
| C1 | 8.2 | NR |
|  | 10.7 | 814.9 |
|  | 11.3 | 726 |
|  | 12.6 | NR |
| D1 | 7.9 | NR |
|  | 9.7 | 816.9 |
|  | 10.8 | 802 |
| F1 | 8.2 | NR |
|  | 9.9 | 833.9 |
|  | 10.9 | 819.9 |
| G1 | 8.7 | 784.1 |
|  | 9.6 | NR |
|  | 10.5 | NR |
|  | 11.7 | 772.1 |

Results of Mutasynthetic Feeding to −2 PKS Module Strain Phenotype C

TABLE 3

| Feed | major product peaks RT/mins | molecular weight |
|---|---|---|
| unfed | 9.7 | NR |
|  | 9.9 | NR |
| A | 7.5 | NR |
|  | 9.6 | 757.5 |
|  | 11.2 | NR |
| B | 7.8 | 743.6 |
|  | 9.6 | 757.5 |
|  | 9.9 | 781.6 |
|  | 11.2 | NR |
| C | 5.4 | 773.6 |
|  | 7.5 | 757.6 |
|  | 10.5 | NR |
|  | 11.2 | NR |
| D | 7.9 | 743.5 |
|  | 9.9 | 756.7 |
|  | 11.2 | NR |
|  | 11.5 | NR |
| E | 7.5 | 741.6 |
|  | 9.5 | 755.6 |
|  | 9.9 | NR |
|  | 11.2 | NR |
| F | 7.0 | NR |
|  | 9.2 | 775.6 |
|  | 10.3 | NR |
| G | 6.6 | 787.8 |
|  | 8.9 | 757.8 |
|  | 9.2 | NR |
|  | 10.2 | 771.6 |
|  | 11.3 | 771.6 |
| H | 9.8 | 751.5 |
|  | 9.9 | NR |

TABLE 3-continued

| Feed | major product peaks RT/mins | molecular weight |
|---|---|---|
| I | 7.9 | 751.6 |
|  | 9.8 | NR |
|  | 10.6 | 771.7 |
| J | 7.8 | 769.6 |
|  | 9.9 | 755.8 |
| K | 8.5 | 769.8 |
|  | 9.1 | 783.5 |
|  | 10.6 | 783.5 |
|  | 11.1 | NR |
| L | 8.9 | NR |
|  | 10.1 | 685.7 |
| M | 7.5 | 751.6 |
|  | 2.9 | NR |
|  | 9.8 | NR |
|  | 9.9 | NR |
| N | 7.3 | NR |
|  | 9.8 | 751.6 |
| O | 9.3 | 771.6 |
| P | 5.7 | NR |
| Q | 9.7 | 757.4 |
|  | 10 | 751.6 |
|  | 10.5 | 771.7 |
|  | 11.4 | NR |
| R | 9.7 | NR |
|  | 10.8 | NR |
|  | 11.6 | 769.6 |
| S | 5.8 | NR |
|  | 10.6 | 769.6 |
| T | 6.6 | 787.6 |
|  | 8.1 | NR |
|  | 8.9 | NR |
|  | 10.3 | 771.7 |
| U | 5.4 | NR |
|  | 7.2 | 759.7 |
|  | 7.5 | 773.7 |
|  | 9.2 | NR |
| V | 5.7 | NR |
|  | 6.7 | 787.6 |
|  | 8.5 | 787.6 |
|  | 9 | NR |
|  | 10.6 | 771.7 |
| W | 4.7 | NR |
|  | 6.1 | NR |
| X | 9.3 | 771.6 |
| A1 | 6.7 | NR |
|  | 7.3 | 757.6 |
|  | 9.3 | NR |
|  | 10.3 | NR |
|  | 10.6 | NR |
| B1 | 6.3 | NR |
|  | 7.7 | NR |
|  | 8.1 | NR |
|  | 9.6 | 769.9 |
| C1 | 7.7 | NR |
|  | 8.3 | NR |
|  | 10.9 | 757.9 |
|  | 11.2 | 757.9 |
|  | 11.8 | NR |
| D1 | 5.86 | NR |
|  | 6.8 | NR |
|  | 8.9 | NR |
|  | 8.9 | 776.1 |
|  | 9.4 | NR |
|  | 9.8 | NR |
|  | 10 | NR |
| F1 | 6.1 | NR |
|  | 7.3 | NR |
|  | 9.2 | 793.9 |
|  | 9.9 | NR |
|  | 10.1 | NR |
| G1 | 6.6 | NR |
|  | 7.1 | NR |
|  | 7.3 | NR |
|  | 7.7 | NR |
|  | 9.7 | 775.9 and 759.0 |

Results of Mutasynthetic Feeding to −3 PKS Module Strain Phenotype D

TABLE 4

| Feed | major product peaks RT/mins | molecular weight |
|---|---|---|
| unfed | 8.7 | NR |
| A | 6 | NR |
|  | 7.4 | NR |
|  | 8.4 | 699.5 |
|  | 10.8 | 713.6 |
| B | 8.4 | NR |
|  | 8.8 | 699.6 |
| C | 5.4 | NR |
|  | 6.1 | NR |
|  | 7.7 | NR |
|  | 8.3 | 697.6 |
|  | 8.7 | NR |
| D | 6.1 | NR |
|  | 8.4 | NR |
|  | 8.8 | 699.7 |
|  | 9.4 | 699.7 |
| E | 6.1 | NR |
|  | 8.3 | 697.6 |
|  | 8.8 | NR |
|  | 11.6 | NR |
|  | 11.9 | NR |
| F | 6.1 | NR |
|  | 6.9 | 717.6 |
|  | 7.8 | 731.6 |
|  | 10.2 | NR |
| G | 7.5 | 729.6 |
|  | 9.2 | 713.7 |
|  | 10.1 | 713.7 |
| H | 8.3 | 709.5 |
|  | 8.7 | 693.5 |
| I | 8.2 | NR |
|  | 8.5 | NR |
|  | 8.6 | 713.6 |
|  | 9.3 | NR |
|  | 9.7 | NR |
| J | 8.9 | 711.6 |
| K | 7 | 741.6 |
|  | 9.6 | 725.5 |
|  | 10.2 | 725.5 |
| L | 7.3 | NR |
|  | 8.7 | 743.6 |
|  | 9.6 | 711.5 |
|  | 11.2 | 713.5 |
|  | 12 | NR |
|  | 12.4 | NR |
| M | 6.1 | 717.6 |
|  | 7.2 | 693.6 |
|  | 8.7 | NR |
| N | 8.6 | 693.6 |
|  | 11.8 | 693.6 |
| O | 6.5 | 713.5 |
|  | 8.1 | NR |
|  | 8.6 | NR |
| P | 4.5 | NR |
|  | 4.8 | NR |
|  | 6 | NR |
|  | 8.7 | NR |
| Q | 8.7 | 723.6 |
|  | 9.4 | 713.6 |
| R | 8.4 | 723.6 |
|  | 8.7 | 693.6 |
|  | 9.8 | 711.7 |
| S | 6.6 | NR |
|  | 8.7 | NR |
|  | 9.3 | NR |
|  | 9.5 | 711.5 |
|  | 12.2 | 725.5 |
| T | 6.6 | NR |
|  | 7.4 | 729.6 |
|  | 9.2 | 713.6 |
|  | 9.8 | NR |
|  | 11.5 | NR |
| U | 5.4 | 731.9 |
|  | 6.1 | 717.5 |

TABLE 4-continued

| Feed | major product peaks RT/mins | molecular weight |
|---|---|---|
|    | 7.1 | 729.7 |
|    | 7.7 | NR |
|    | 8.7 | NR |
| V  | 7   | NR |
|    | 8.4 | 729.5 |
|    | 9.5 | 713.7 |
|    | 9.9 | 743.6 |
| W  | 4.8 | 693.5 |
|    | 8.7 | NR |
| X  | 6.4 | NR |
|    | 8.1 | 713.5 |
| A1 | 7.4 | NR |
|    | 7.7 | NR |
|    | 8.4 | 699.8 |
|    | 10.8 | 713.7 |
|    | 12.1 | NR |
| B1 | 7.4 | NR |
|    | 8.8 | 711.9 |
|    | 12.5 | NR |
| C1 | 6.1 | NR |
|    | 8.2 | NR |
|    | 8.8 | NR |
|    | 9.4 | 699.9 |
|    | 12.9 | NR |
| D1 | 6.9 | 717.9 |
|    | 7.9 | 717.9 |
|    | 8.4 | NR |
|    | 8.9 | NR |
|    | 10.1 | NR |
|    | 11.5 | NR |
| E1 | 8.4 | NR |
|    | 10.4 | NR |
|    | 13.2 | NR |
| F1 | 7.33 | 735.8 |
|    | 7.7 | NR |
|    | 8.2 | 749.9 |
|    | 8.7 | NR |
|    | 10.3 | 735.8 |
|    | 10.8 | NR |
| G1 | 6.1 | NR |
|    | 8.8 | 699.9 |
|    | 9.3 | 699.9 |
|    | 12.3 | NR |

Results of Mutasynthetic Feeding to −4 PKS Module Strain Phenotype E

TABLE 5

| Feed | major product peaks RT/mins | molecular weight |
|---|---|---|
| Unfed | 5.1 | NR |
| A | 4.6 | 629.7 |
|   | 8.8 | 671.9 |
| B | 5.3 | 629.7 |
| C | 8.4 | 655.8 |
| D | 5.4 | NR |
| E | 4.8 | NR |
|   | 12  | NR |
| F | 4.1 | 647.7 |
|   | 7.2 | 689.9 |
| G | 5.2 | 643.5 |
| H | 5.1 | NR |
| I | 5.5 | 643.8 |
| J | 5.2 | NR |
|   | 9   | NR |
| K | 6.02 | 655.5 |
|   | 9.9 | NR |
| L | 6.3 | NR |
| M | 5.1 | NR |
| N | 5.1 | 623.5 |
| O | 11.2 | NR |
| Q | 5.1 | NR |
| R | 5.1 | NR |
| S | 5.1 | NR |
| T | 5.2 | NR |

TABLE 5-continued

| Feed | major product peaks RT/mins | molecular weight |
|---|---|---|
| U | 4.1 | NR |
|   | 4.8 | NR |
|   | 8.4 | 673.6 |
| V | 5.7 | NR |
|   | 9.8 | 687.7 |
|   | 10.1 | 703.7 |
|   | 10.5 | 703.7 |
| W | 3.8 | 608.8 |
| X | 3.2 | NR |
|   | 6.7 | 689.3 |
|   | 11.1 | 671.8 |
|   | 11.6 | 686.7 |
| A1 | 4.6 | NR |
|    | 5.5 | NR |
|    | 7.6 | NR |
|    | 8.7 | NR |
|    | 9.3 | NR |
|    | 9.5 | NR |
| B1 | 5.1 | NR |
|    | 8.3 | NR |
|    | 8.8 | NR |
|    | 9.8 | NR |
| C1 | 5.4 | NR |
|    | 10  | NR |
| D1 | 4.1 | NR |
|    | 4.6 | NR |
|    | 5.7 | NR |
|    | 6.9 | NR |
|    | 7.1 | NR |
|    | 8.1 | NR |
|    | 8.5 | NR |
| E1 | 4.6 | NR |
|    | 7.7 | 647.7 |
|    | 10.7 | NR |
|    | 13.4 | NR |
| F1 | 4.3 | 697.6 |
|    | 4.4 | NR |
|    | 7.3 | NR |
|    | 8.7 | NR |
| G1 | 5.3 | NR |
|    | 6.7 | NR |
|    | 9.7 | NR |
|    | 12.5 | NR |

Results of Mutasynthetic Feeding to −6 PKS Module Strain Phenotype G

TABLE 6

| Feed | major product peaks RT/mins | MW (difference from truncated pre-rap) |
|---|---|---|
| Unfed | nd | NR |
| A | 5.1 | 561.5 |
|   | 6.7 | 575.5 |
|   | 8.1 | 557.9 |
|   | 9.2 | NR |
| B | 5.07 | 561.5 |
|   | 6.7 | 575.5 |
|   | 8.1 | 557.9 |
|   | 9.3 | NR |
| C | 5.1 | 561.4 |
|   | 6.1 | 573.7 |
|   | 8.6 | NR |
| D | 5   | 561.4 |
|   | 6   | NR |
|   | 6.7 | 575.5 |
|   | 7.8 | NR |
|   | 9.2 | NR |
|   | 10.3 | NR |
| E | 4.5 | NR |
|   | 6.1 | 574 |
|   | 7.5 | NR |
|   | 8.6 | NR |
| F | 4.4 | NR |
|   | 5.9 | NR |

TABLE 6-continued

| Feed | major product peaks RT/mins | MW (difference from truncated pre-rap) |
|---|---|---|
| | 7.2 | NR |
| | 8.2 | NR |
| G | 6.3 | NR |
| | 7.6 | NR |
| | 8.1 | NR |
| | 10.2 | NR |
| | 10.7 | NR |
| I | 6.1 | NR |
| | 7.8 | 590 |
| | 9.3 | NR |
| | 10.3 | 604.5 |
| J | 5.4 | 573.4 |
| | 7.1 | 587.9 |
| | 8.5 | NR |
| | 9.7 | 602 |
| K | 6.1 | NR |
| | 6.3 | NR |
| | 7.8 | 601.8 |
| | 8.2 | NR |
| L | 6.2 | 547.4 |
| | 8.1 | 561.9 |
| | 9.7 | NR |
| | 10.8 | NR |
| M | 9 | NR |
| | 10.9 | NR |
| N | 4.8 | 622.7 |
| | 6.4 | 569.9 |
| O | nd | NR |
| Q | 7.6 | 612.9 |
| | 8.01 | NR |
| | 8.9 | 603.8 |
| R | 8.4 | NR |
| | 7.6 | NR |
| S | 12.2 | 557 |
| T | 7.6 | 589.9 |
| U | 3.9 | 591.9 |
| | 4.2 | NR |
| | 6.05 | 605.7 |
| V | 6.3 | 575.6 |
| | 8.02 | 589.9 |
| | 10.6 | NR |
| X | 6.8 | NR |
| | 9.05 | NR |
| | 10.8 | NR |
| A1 | 4.4 | NR |
| | 5.1 | 561.7 |
| | 6.7 | 575.8 |
| | 7.1 | NR |
| | 7.5 | 557.8 |
| | 7.7 | NR |
| B1 | 5.4 | 575.9 |
| | 7.1 | 587.9 |
| | 7.6 | NR |
| | 9.6 | 569.8 |
| C1 | 3.3 | NR |
| | 4.7 | NR |
| | 5 | NR |
| | 5 | NR |
| | 6 | NR |
| | 6.7 | NR |
| | 7.8 | 575.6 |
| | 8.6 | 577.8 |
| | 9 | NR |
| | 10.2 | 589.1 |
| | 10.8 | NR |
| D1 | 3.7 | NR |
| | 4.5 | 579.8 |
| | 5.1 | NR |
| | 5.9 | 593.7 |
| | 6.6 | NR |
| | 7.1 | NR |
| | 7.7 | NR |
| | 8.2 | 575.6 |
| | 8.8 | NR |
| E1 | 5.1 | NR |
| | 6.7 | NR |
| | 7.3 | NR |
| | 8.6 | 603.7 |
| F1 | 3.9 | NR |
| | 4.7 | 597.6 |
| | 5.5 | NR |
| | 6.1 | 611.8 |
| | 6.8 | NR |
| | 7.3 | NR |
| | 7.6 | NR |
| | 8.4 | 593.8 |
| | 8.9 | NR |
| G1 | 4.1 | NR |
| | 5 | 561.7 |
| | 5.9 | NR |
| | 6.7 | 575.8 |
| | 7.5 | NR |
| | 7.7 | NR |
| | 8.2 | NR |
| | 8.4 | NR |
| | 9.3 | NR |

Example 18

Isolation of Compounds 18, 19, 20, 21 & 22

Strain: Phenotype B from BIOT-4827

Feed: 4-trans-hydroxylcyclohexanecarboxylic acid (final concentration 2 mM)

2×60 liter fermentation

The fermentation was as described above.

The fermentation broth at the end of the fermentation was collected and standard techniques were used to isolate the following compounds:

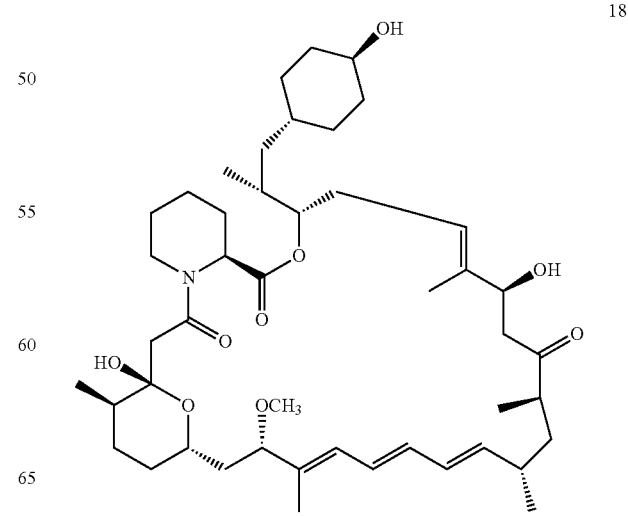

19

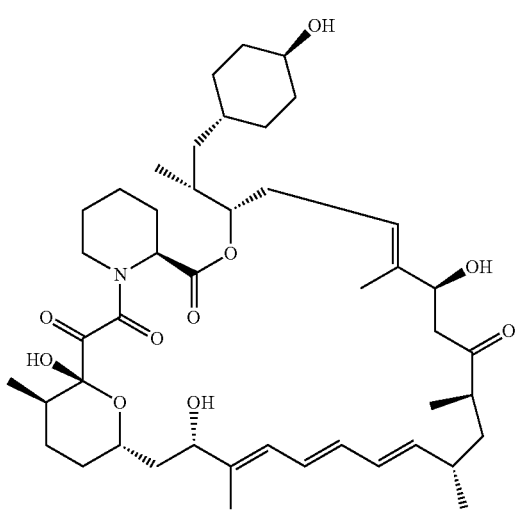

20

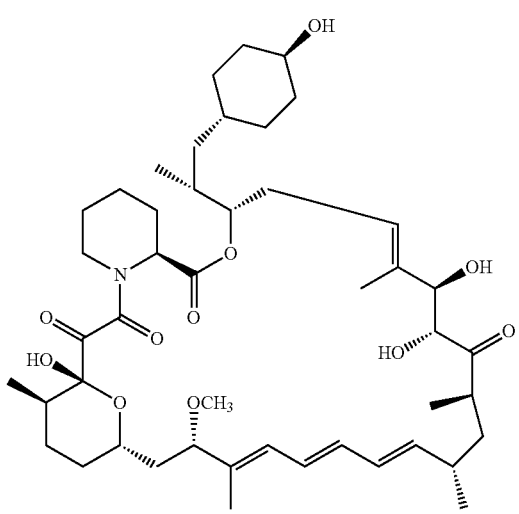

21

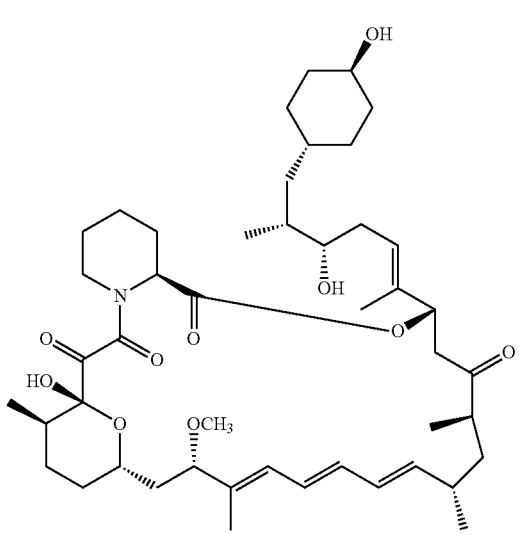

22

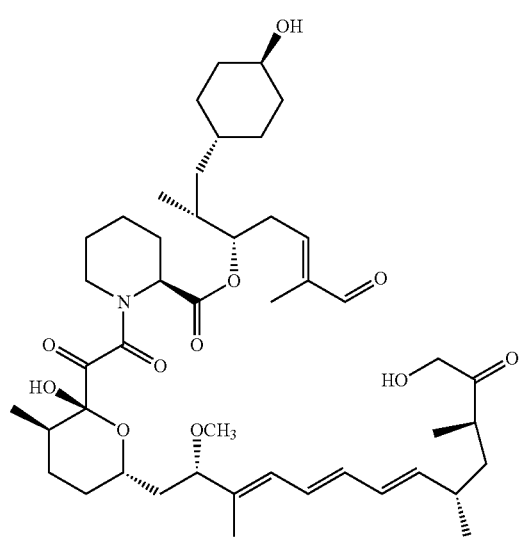

Example 19

Biological Data: Inhibition of FKBP12 PPIase Activity

The rapamycin analogues were tested for their ability to inhibit FKBP12, using a peptidyl-prolyl isomerase (PPlase) assay. All compounds were assayed at 6 concentrations in duplicate and the data fitted to a Ki curve to afford a Ki value with standard error (SE).

| Compound no. | MW | Ki (nM) | SE (nM) |
| --- | --- | --- | --- |
| Rapamycin | 914.17 | 5.4 | 0.35 |
| FK506 | 804.02 | 10 | 1.1 |
| Meridamycin | 870.1193 | 10 | 1.1 |
| 2 | 561.7498 | 19% at 1 uM | |
| 5 | 798.06 | 7.9 | 0.69 |
| 6 | 699.96 | 370 | 43 |
| 3 | 575.78 | 25% at 1 uM | |
| 8 | 828.08 | 5.9 | 0.66 |
| 9 | 800.0725 | 180 | 11 |
| 10 | 814.06 | 4.2 | 0.28 |
| 11 | 800.0725 | 430 | 32 |
| 12 | 812.06 | 9.5 | 0.73 |
| 13 | 777 | 13 | 1.4 |
| 14 | 898.17 | 6.5 | 0.66 |
| 15 | 627.81 | 31% at 1 uM | |
| 16 | 613.78 | 460 | 34 |
| 18 | 784.07 | 45 | 4.1 |
| 19 | 784.03 | 7.7 | 0.74 |
| 20 | 814.06 | 18 | 1.3 |
| 21 | 798.06 | 95 | 7.2 |
| 22 | 814.06 | 12 | 0.97 |

As can be seen, the majority of the rapamycin analogues tested show potent inhibition of FKBP12 (Ki<1 μM) in this assay.

Example 20

Biological Data: Inhibition of the PLP T-Cell Proliferation Assay (PLP Assay)

The immunosuppressive potency of rapamycin analogues can be tested using a PLP T-cell proliferation assay. mTOR is known to regulate the expression of Proteo Lipo Protein (Tyler et al. 2009), and activity of rapamycin analogues in this assay is driven by mTOR inhibition, so for rapamycin analogues where the aim is to inhibit FKBPs, this is an off-target activity. Therefore we also calculated the ratio of the FKBP12 $IC_{50}$ to the PLP assay $IC_{50}$, with a comparison to rapamycin. Larger ratios therefore relate to compounds with an improved window of activity.

| Compound number | PLP IC50 (nM) | Ratio (PLP/FKBP*) |
|---|---|---|
| Rapamycin | 0.024 | 0.004444 |
| 2 | 113.4 | N/A |
| 4 | 4464 | N/A |
| 6 | 2625 | 7.094595 |
| 3 | 1453 | N/A |
| 8 | 490 | 83.05085 |
| 10 | 14021 | 3338.333 |
| 11 | 4180 | 9.72093 |
| 12 | 2865 | 301.5789 |
| 13 | 6586 | 506.6154 |

*data from Example 19 (Ki values)

As can be seen, all of the rapamycin analogues tested show higher (and therefore improved) ratios of PLP $IC_{50}$ to FKBP12 Ki as compared to rapamycin.

Example 21

Cytotoxicity Reduction Assay

Several compounds of the invention were tested in this assay and showed a reduction in cytotoxicity.

REFERENCES

Marshall, J. A., and Shiping, X. (1995) *J. Org. Chem.*, 60, 7230-7237

Strässler, C., Linden, A., and Heimgartner, H. (1997). *Helv. Chim. Acta.* 80: 1528-1554

Becker and Rickards, *Aust. J. Chem.*, 1984, 37, 2104

Tyler W A, Gangoli N, Gokina P, Kim H A, Covey M, Levison S W, Wood T L. *J Neurosci.* 2009 May 13; 29(19):6367-78. doi: 10.1523/JNEUROSCI.0234-09.2009.

Reeves C D, Rodriguez E *Methods Enzymol.* 2009; 459: 295-318. doi: 10.1016/S0076-6879(09)04613-8.

Staunton J, Weissman K J. *Nat Prod Rep.* 2001 August; 18(4):380-416.

Koehn F E. *Prog Drug Res.* 2008; 65:175, 177-210.

Koehn F E, Carter G T. *Discov Med.* 2005 April; 5(26):159-64.

Giessen T W, Marahiel M A. *FEBS Lett.* 2012 Jul. 16; 586(15):2065-75. doi: 10.1016/j.febslet.2012.01.017. Epub 2012 Jan. 21.

Pfeifer B A, Khosla C. *Microbiol Mol Biol Rev.* 2001 March; 65(1):106-18.

Bierman M, Logan R, O'Brien K, Seno E T, Rao R N, Schoner B E. *Gene.* 1992 Jul. 1; 116(1):43-9. Kendrew S G, Petkovic H, Gaisser S, Ready S J, Gregory M A, Coates N J, Nur-E-Alam M, Warneck T, Suthar D, Foster T A, McDonald L, Schlingman G, Koehn F E, Skotnicki J S, Carter G T, Moss S J, Zhang M Q, Martin C J, Sheridan R M, Wilkinson B. *Metab Eng.* 2013 January; 15:167-73. doi: 10.1016/j.ymben.2012.11.001. Epub 2012 Nov. 17.

Schwecke T, Aparicio J F, Molnár I, König A, Khaw L E, Haydock S F, Oliynyk M, Caffrey P, Cortés J, Lester J B, et al. *Proc Natl Acad Sci USA.* 1995 Aug. 15; 92(17): 7839-43.

Gaisser S, Kellenberger L, Kaja A L, Weston A J, Lill R E, Wirtz G, Kendrew S G, Low L, Sheridan R M, Wilkinson B, Galloway I S, Stutzman-Engwall K, McArthur H A, Staunton J, Leadlay P F. *Org Biomol Chem.* 2003 Aug. 21; 1(16):2840-7.

Li J W-H, Vederas J C. *Science* 2009 325(161) DOI: 10.1126/science.1168243

Cao W, Konsolaki M. *J Biosci.* 2011 August; 36(3):493-8.

Gerard M, Deleersnijder A, Demeulemeester J, Debyser Z, Baekelandt V. *Mol Neurobiol.* 2011 August; 44(1):13-27. doi: 10.1007/s12035-011-8184-2. Epub 2011 May 7.

Norville I H, Harmer N J, Harding S V, Fischer G, Keith K E, Brown K A, Sarkar-Tyson M, Titball R W. *Infect Immun.* 2011 November; 79(11):4299-307. doi: 10.1128/IAI.00134-11. Epub 2011 Aug. 22.

Leuzzi R, Serino L, Scarselli M, Savino S, Fontana M R, Monaci E, Taddei A, Fischer G, Rappuoli R, Pizza M. *Mol Microbiol.* 2005 November; 58(3):669-81.

Moro A, Ruiz-Cabello F, Fernández-Cano A, Stock R P, González A. *EMBO J.* 1995 Jun. 1; 14(11):2483-90.

Hoerauf A, Rascher C, Bang R, Pahl A, Solbach W, Brune K, Röllinghoff M, Bang H. *Mol Microbiol.* 1997 April; 24(2):421-9.

Zang N, Tang D J, Wei M L, He Y Q, Chen B, Feng J X, Xu J, Can Y Q, Jiang B L, Tang J L. *Mol Plant Microbe Interact.* 2007 January; 20(1):21-30.

Kang C B, Hong Y, Dhe-Paganon S, Yoon H S. *Neurosignals.* 2008; 16(4):318-25. doi: 10.1159/000123041. Epub 2008 Jul. 18.

Bové J, Martinez-Vicente M, Vila M. *Nat Rev Neurosci.* 2011 Jul. 20; 12(8):437-52. doi: 10.1038/nrn3068.

Ruan B, Pong K, Jow F, Bowlby M, Crozier R A, Liu D, Liang S, Chen Y, Mercado M L, Feng X, Bennett F, von Schack D, McDonald L, Zaleska M M, Wood A, Reinhart P H, Magolda R L, Skotnicki J, Pangalos M N, Koehn F E, Carter G T, Abou-Gharbia M, Graziani El. *Proc Natl Acad Sci USA.* 2008 Jan. 8; 105(1):33-8. Epub 2007 Dec. 27.

Chambraud B, Sardin E, Giustiniani J, Dounane O, Schumacher M, Goedert M, Baulieu E E. *Proc Natl Acad Sci USA.* 2010 Feb. 9; 107(6):2658-63. doi: 10.1073/pnas.0914957107. Epub 2010 Jan. 25.

Shim S, Yuan J P, Kim J Y, Zeng W, Huang G, Milshteyn A, Kern D, Muallem S, Ming G L, Worley P F. *Neuron.* 2009 Nov. 25; 64(4):471-83. doi: 10.1016/j.neuron.2009.09.025.

Labrande C, Velly L, Canolle B, Guillet B, Masmejean F, Nieoullon A, Pisano P. *Neuroscience.* 2006; 137(1):231-9. Epub 2005 Nov. 10.

Avramut M, Achim C L. *Physiol Behav.* 2002 December; 77(4-5):463-8.

Deleersnijder A, Van Rompuy A S, Desender L, Pottel H, Buée L, Debyser Z, Baekelandt V, Gerard M. *J Biol Chem.* 2011 Jul. 29; 286(30):26687-701. doi: 10.1074/jbc.M110.182303. Epub 2011 Jun. 7.

Norville I et al., 2013 Poster presentation Cyclophilins and other foldases: Cell Signalling catalysts and drug targets, Halle, Germany, Sep. 19-21, 2013.

Norville et al., 2011, *Burkholderia pseudomallei* Mip-like Protein has Rapamycin Inhibitable Peptidyl-Prolyl Isomerase Activity and has Pleiotrophic Effects on Virulence. *Infection and Immunity.* 2011; 79(11):4299-307

Norville et al., 2011, The structure of a *Burkholderia pseudomallei* immunophilin-inhibitor complex reveals new approaches to antimicrobial development. *Biochem J.* 2011; 437(3):413-22.

Andrews J M, 2001 J. Antimicrob. Chemother. (2001) 48 (suppl 1): 5-16. doi: 10.1093/jac/48.suppl_1.5

Travis J., Potempa J. 2000. Bacterial proteinases as targets for the development of second-generation antibiotics. Biochim. Biophys. Acta 1477:35-50.

Crunkhorn S. 2008. Antibacterial drugs: new paths to beating bacteria. Nat. Rev. Drug Discov. 7:891

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A rapamycin analogue of formula (I) or a pharmaceutically acceptable salt thereof

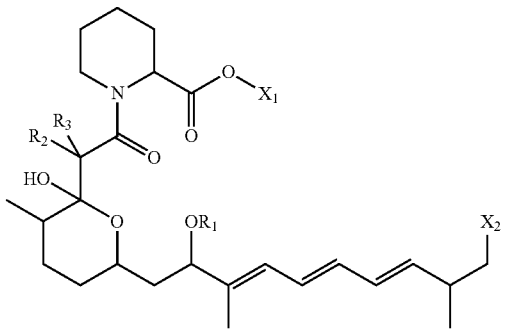

wherein:
$R_1$ represents Me or H;
$R_2$ and $R_3$ represent H or $R_2$ and $R_3$ taken together represent keto;
$X_1$ and $X_2$ are connected by a moiety selected from the group consisting of:

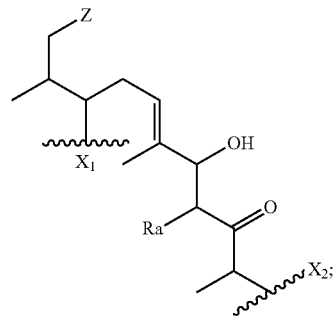

-continued

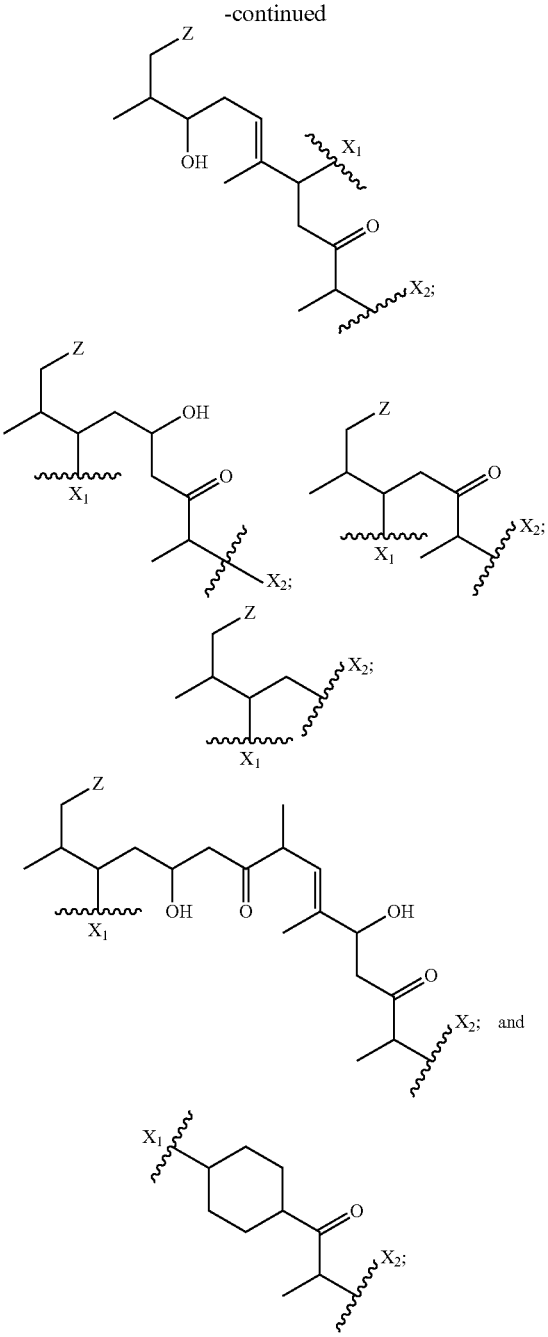

or $X_2$ is connected as follows:

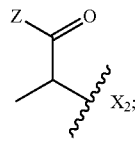

and $X_1$ is H;
or $X_1$ represents H and $X_2$ represents Z;
$R_a$ is selected from the group consisting of H, OH and OMe;

Z represents

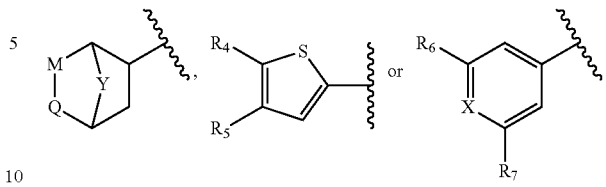

Y represents methylene or is absent;
M is selected from the group consisting of bond, $CH_2$, CHMe, CHF, CHOH, $CH_2CH_2$ CH(OMe), $CMe_2$, CHEt and $CF_2$;
Q is selected from the group consisting of bond, $CH_2$, CHMe, CHF, CHOH, $CH_2CH_2$, O, S, $CHCH_2OH$, C(OH)Me and CH(OMe);
provided that:
(i) when Q is not O or S then one of M or Q must represent CHOH $CHCH_2OH$ or C(OH)Me; and
(ii) if Q is O or S, then M does not represent CHF, $CF_2$, CHOMe, CHOH; and
(iii) M and Q do not both represent bond;
either $R_4$ represents $CH_2OH$ and $R_5$ represents H or $R_4$ represents H and $R_5$ represents $CH_2OH$; and
either $R_6$ represents OH, $R_7$ represents $NH_2$ or H and X represents CH; or
$R_6$ represents H, $R_7$ represents H and X represents N.

2. The compound according to claim 1 or a pharmaceutically acceptable salt thereof wherein $X_1$ and $X_2$ are connected as follows:

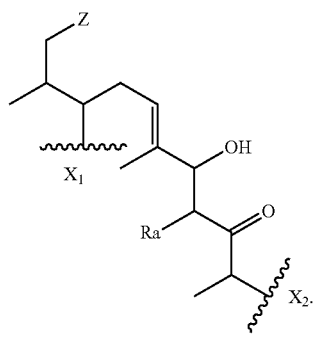

3. The compound according to claim 1 or a pharmaceutically acceptable salt thereof wherein $X_1$ and $X_2$ are connected as follows:

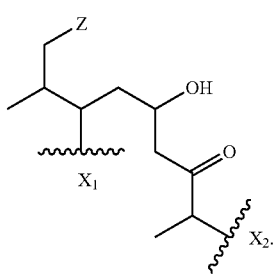

4. The compound according to claim 1 or a pharmaceutically acceptable salt thereof wherein $X_1$ and $X_2$ are connected as follows:

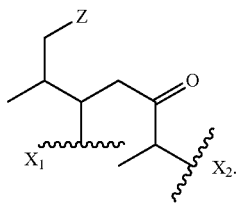

5. The compound according to claim 1 or a pharmaceutically acceptable salt thereof wherein Z represents

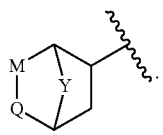

6. The compound according to claim 5 or a pharmaceutically acceptable salt thereof wherein Y represents methylene or is absent, M represents $CH_2$ and Q represents CHOH; or Y is absent; M represents CHOMe and Q represents CHOH; or Y is absent, M represents CHF and Q represents CHOH; or Y is absent, M represents CHOH and Q represents $CH_2$; or Y is absent, M represents $CH_2$ and Q represents C(OH)Me; or Y is absent, M=bond; Q=CHOH; or Y is absent, M=$CH_2CH_2$; Q=CHOH; or Y represents methylene, M represents $CH_2CH_2$, Q represents CHOH; or Y is absent, M represents $CH_2$, Q represents O; or Y is absent, M represents $CH_2$, Q represents S; or Y represents methylene, M represents $CMe_2$, Q represents CHOH; or Y is absent, M represents CHOH; Q represents CHOH; or Y is absent, M represents CHMe; Q represents CHOH; or Y is absent, M represents $CF_2$; Q represents CHOH; or Y is absent, M represents CHEt; Q represents CHOH.

7. The compound according to claim 5 or a pharmaceutically acceptable salt thereof wherein Z is selected from the group consisting of 4-hydroxycyclohexane, 3-methoxy-4-hydroxy-cyclohexane and 3,4-dihydroxycyclohexane.

8. The compound according to claim 1 or a pharmaceutically acceptable salt thereof wherein Z represents

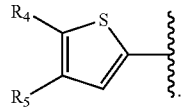

9. The compound according to claim 8 or a pharmaceutically acceptable salt thereof wherein $R_4$ represents $CH_2OH$ and $R_5$ represents H.

10. The compound according to claim 1 or a pharmaceutically acceptable salt thereof wherein Z represents

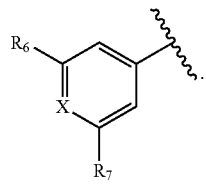

11. The compound according to claim 10 or a pharmaceutically acceptable salt thereof wherein Z represents pyridin-4-yl.

12. The compound according to claim 1 wherein $R_1$ represents H.

13. The compound according to claim 1 wherein $R_1$ represents Me.

14. The compound according to claim 1 wherein $R_2$ and $R_3$ each represent H.

15. The compound according to claim 1 wherein $R_2$ and $R_3$ together represent keto.

16. The compound of formula (I) according to claim 1 or a pharmaceutically acceptable salt thereof, wherein the compound of formula (I) is selected from the group consisting of:

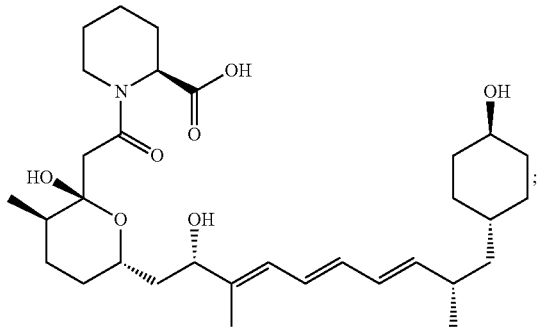

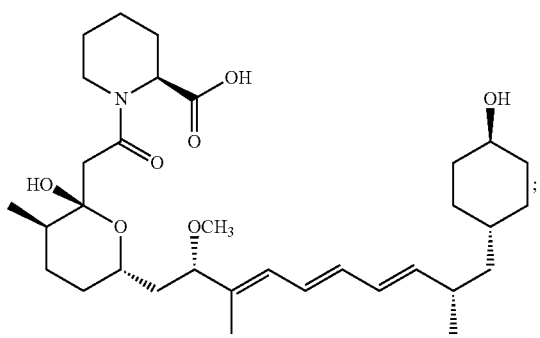

87
-continued
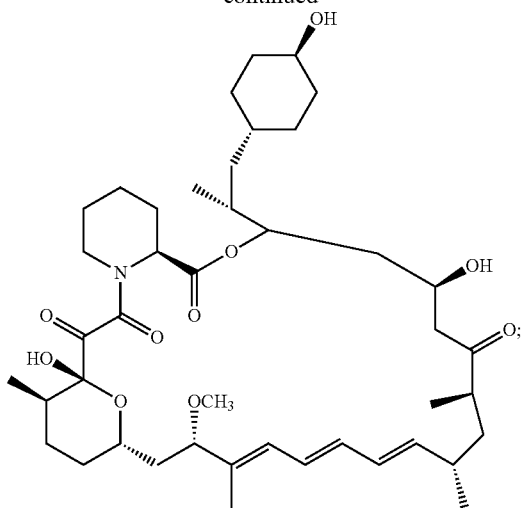
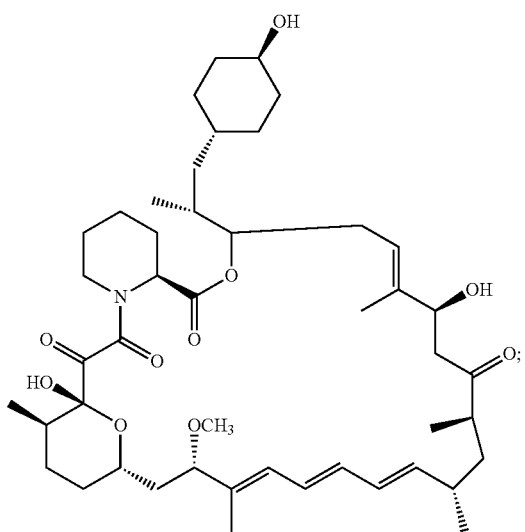
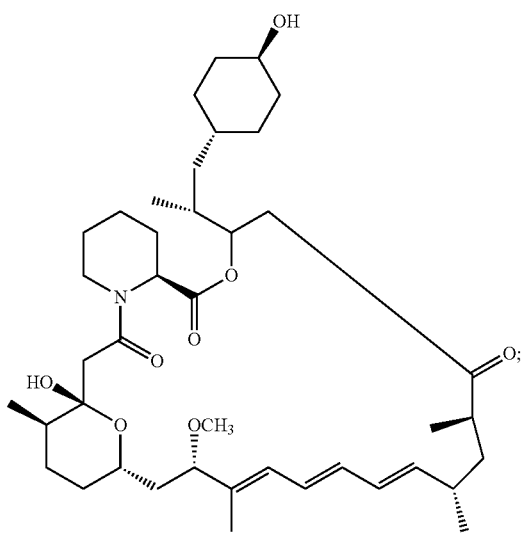
88
-continued
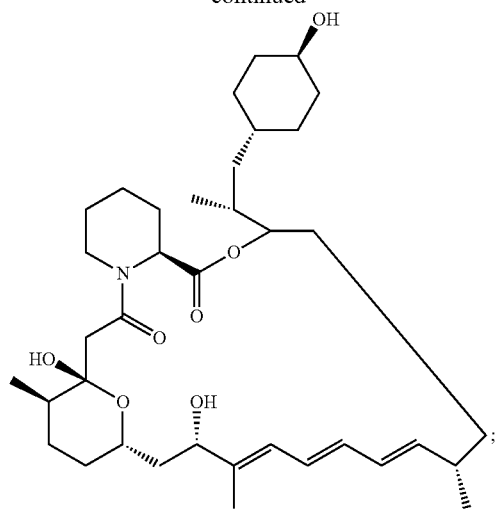
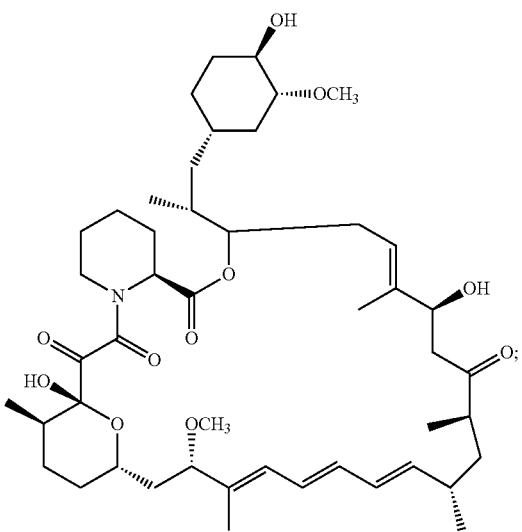
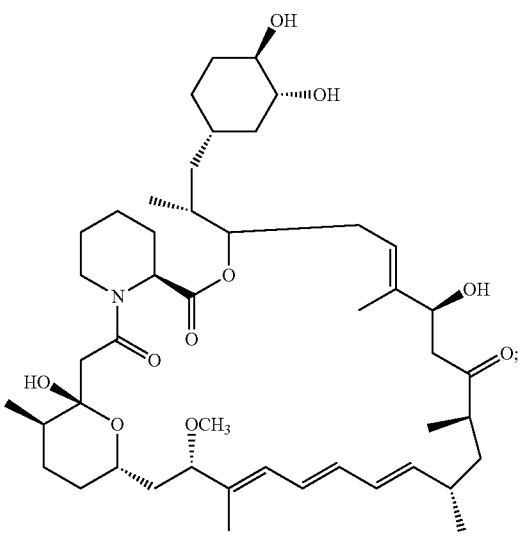

-continued
89
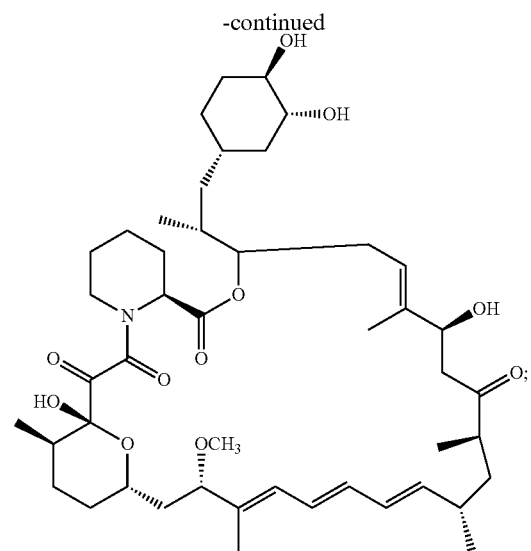
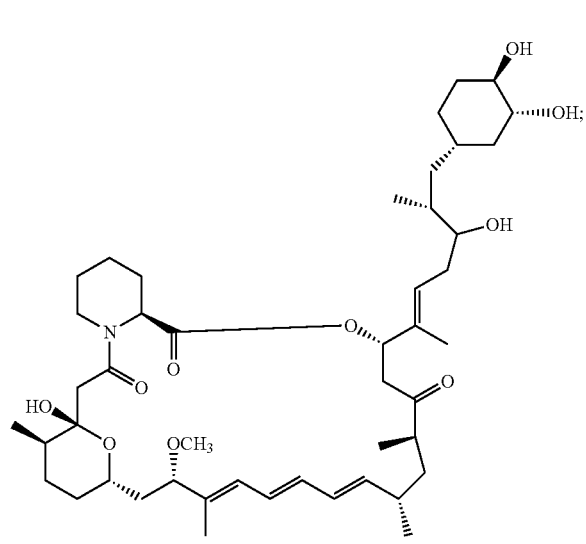
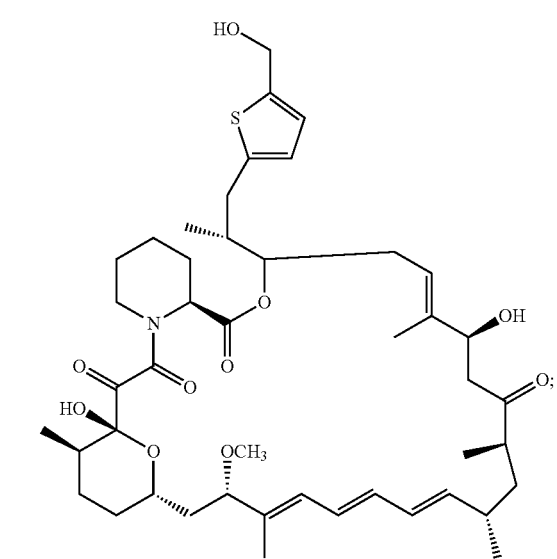
90
-continued
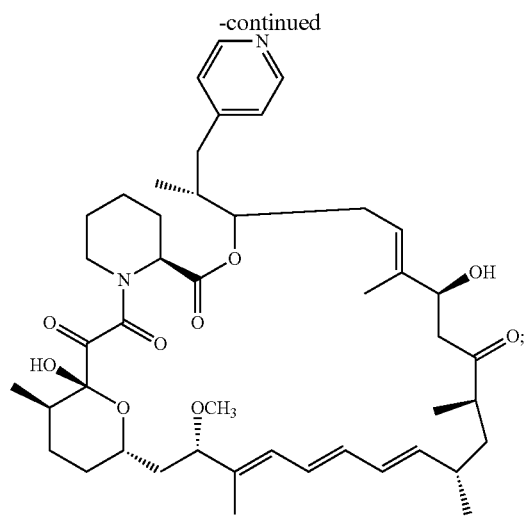
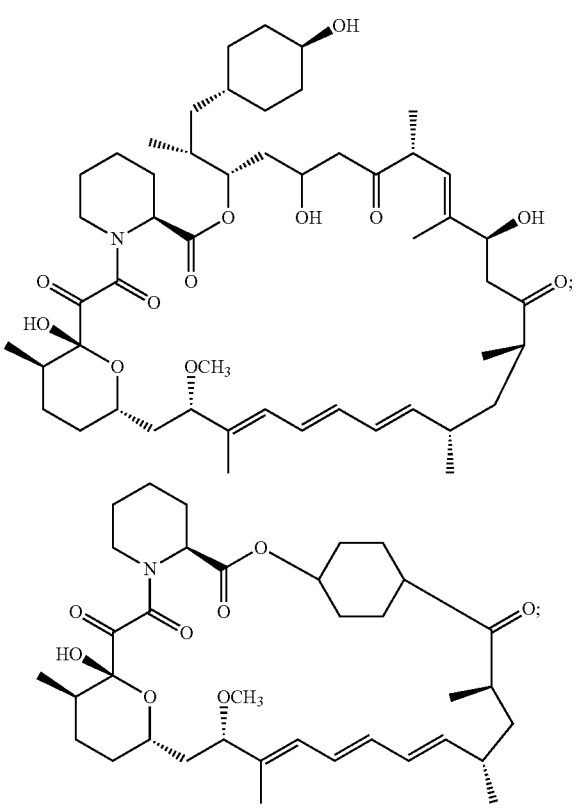

91
-continued

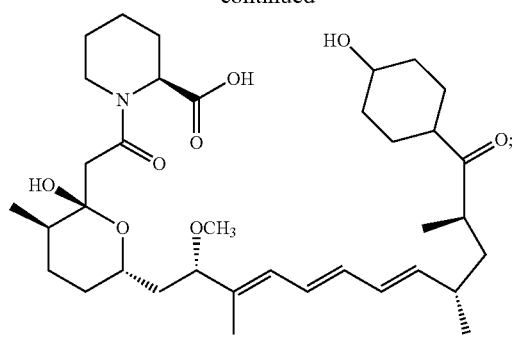

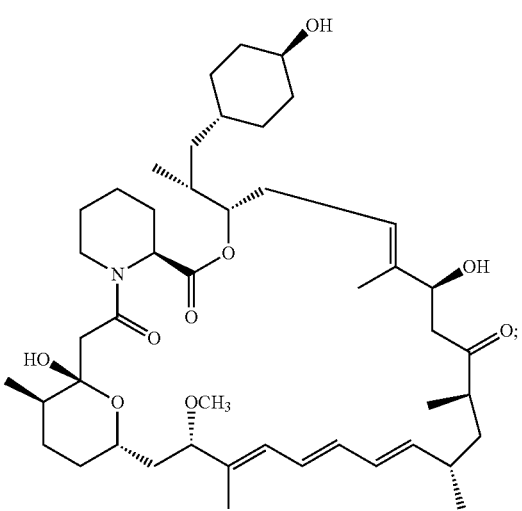

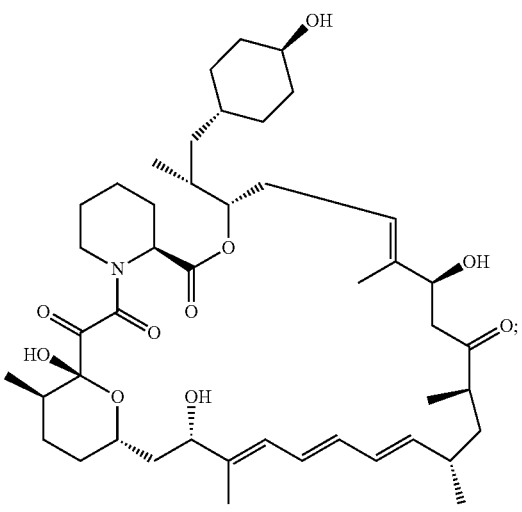

92
-continued

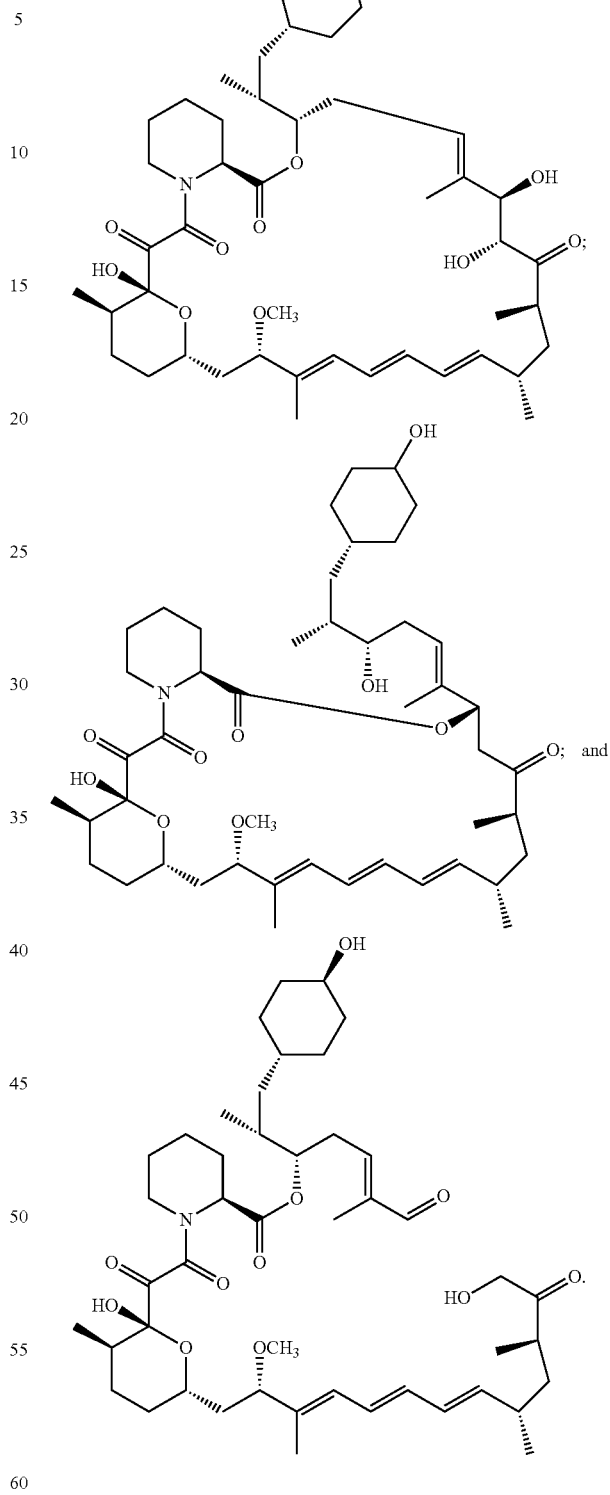

17. A pharmaceutical composition comprising the compound according to claim 1 and one or more pharmaceutically acceptable diluents or carriers.

18. The composition according to claim 17 which comprises a second or further active ingredient for the treatment of a microbial infection selected from the group consisting of *Burkholderia* sp., *Legionella* sp., *Chlamydia* sp.,

*Pseudomonas* sp., *Klebsiella* sp., *Neisseria* sp., *Actinobacter* sp., *Coxiella* sp., and *Trypanosoma* sp.

19. The composition according to claim 17 which comprises a second or further active ingredient for the treatment of a microbial infection selected from the group consisting of *Burkholderia pseudomallei, Pseudomonas aeruginosa,